(12) United States Patent
Davis et al.

(10) Patent No.: US 11,630,316 B1
(45) Date of Patent: Apr. 18, 2023

(54) MINIATURIZED COLLIMATORS

(71) Applicant: Brigham Young University, Provo, UT (US)

(72) Inventors: Robert Davis, Provo, UT (US); Richard Vanfleet, Provo, UT (US); Nick Morrill, Provo, UT (US); David Miller, Morgan, UT (US)

(73) Assignee: Brigham Young University, Provo, UT (US)

( * ) Notice: Subject to any disclaimer, the term of this patent is extended or adjusted under 35 U.S.C. 154(b) by 684 days.

(21) Appl. No.: 16/669,386

(22) Filed: Oct. 30, 2019

(51) Int. Cl.
*G02B 27/30* (2006.01)
*G06V 40/13* (2022.01)
*A61B 5/00* (2006.01)

(52) U.S. Cl.
CPC ............ *G02B 27/30* (2013.01); *A61B 5/0075* (2013.01); *A61B 5/681* (2013.01); *A61B 2562/028* (2013.01); *A61B 2562/0285* (2013.01); *A61B 2562/04* (2013.01); *G02B 2207/101* (2013.01)

(58) Field of Classification Search
CPC . G02B 27/30; G02B 5/20; G02B 5/22; G06V 40/1324
See application file for complete search history.

(56) References Cited

U.S. PATENT DOCUMENTS

| | | |
|---|---|---|
| 5,009,230 A | 4/1991 | Hutchinson |
| 6,006,119 A | 12/1999 | Soller et al. |
| 6,200,737 B1 | 3/2001 | Walt et al. |
| 6,203,814 B1 | 3/2001 | Fisher et al. |
| 6,283,812 B1 | 9/2001 | Jin et al. |
| 6,361,861 B2 | 3/2002 | Gao et al. |
| 6,426,134 B1 | 7/2002 | Lavin et al. |
| 6,505,775 B1 | 1/2003 | Gu et al. |
| 6,766,188 B2 | 7/2004 | Soller |
| 6,863,857 B2 | 3/2005 | Luzzi et al. |
| 7,011,771 B2 | 3/2006 | Gao et al. |
| 7,047,054 B2 | 5/2006 | Benni |
| 7,126,682 B2 | 10/2006 | Rowe et al. |

(Continued)

FOREIGN PATENT DOCUMENTS

| | | |
|---|---|---|
| CN | 103087682 A | 5/2013 |
| CN | 103698010 A | 4/2014 |

(Continued)

*Primary Examiner* — Ryan D Howard
(74) *Attorney, Agent, or Firm* — Miller IP LLC

(57) ABSTRACT

A method, system, apparatus, and/or device to determine a condition of a user using a miniaturized collimator. The method, system, apparatus, and/or device may include: a carbon nanotube structure comprising a microtube that includes a set of aligned carbon nanotubes infiltrated by carbon and a through-channel, the carbon nanotube structure having a defined height to through-channel width aspect ratio, where: the defined height to through-channel width aspect ratio is based on a defined collimation to diffraction ratio; the set of aligned carbon nanotubes infiltrated by carbon is configured to absorb a first portion of light that travels through the through-channel at a first angle and impinges a side of a first through-channel portion; and the set of aligned carbon nanotubes infiltrated by the carbon is configured to allow a second portion of the light that enters the through-channel at a second angle to pass through the through-channel.

19 Claims, 22 Drawing Sheets

(56) References Cited

U.S. PATENT DOCUMENTS

| | | |
|---|---|---|
| 7,151,598 B2 | 12/2006 | Poponin |
| 7,483,112 B2 | 1/2009 | Kim et al. |
| 7,532,919 B2 | 5/2009 | Soyemi et al. |
| 7,750,297 B1 | 7/2010 | Chow et al. |
| 7,756,251 B2 | 7/2010 | Davis |
| 7,837,905 B2 | 11/2010 | Barker et al. |
| 7,897,248 B2 | 3/2011 | Barrera et al. |
| 7,972,536 B2 | 7/2011 | Connell et al. |
| 7,972,875 B2 | 7/2011 | Rogers et al. |
| 8,055,321 B2 | 11/2011 | Bemreuter |
| 8,488,743 B2 | 7/2013 | Verman |
| 8,784,937 B2 | 7/2014 | Malet et al. |
| 8,859,667 B2 | 10/2014 | Grabowski et al. |
| 8,956,289 B2 | 2/2015 | Kitajima et al. |
| 9,057,689 B2 | 6/2015 | Soller et al. |
| 9,095,291 B2 | 8/2015 | Soller et al. |
| 9,105,782 B2 | 8/2015 | Rogers et al. |
| 9,414,782 B2 | 8/2016 | Braig et al. |
| 2002/0091324 A1 | 7/2002 | Kollias et al. |
| 2003/0032064 A1 | 2/2003 | Soller et al. |
| 2004/0005717 A1 | 1/2004 | Soller |
| 2007/0035226 A1 | 2/2007 | Ganapathiraman et al. |
| 2007/0139765 A1 | 6/2007 | Daniel et al. |
| 2009/0186214 A1 | 7/2009 | Lafdi et al. |
| 2010/0002324 A1 | 1/2010 | Rozhin et al. |
| 2012/0121683 A1 | 5/2012 | Gogotsi et al. |

FOREIGN PATENT DOCUMENTS

| | | | | |
|---|---|---|---|---|
| CN | 104726844 A | 6/2015 | | |
| CN | 106654823 A | 5/2017 | | |
| EP | 3537189 A1 * | 9/2019 | ............ | G02B 27/30 |
| JP | 5119407 B2 | 1/2013 | | |

\* cited by examiner

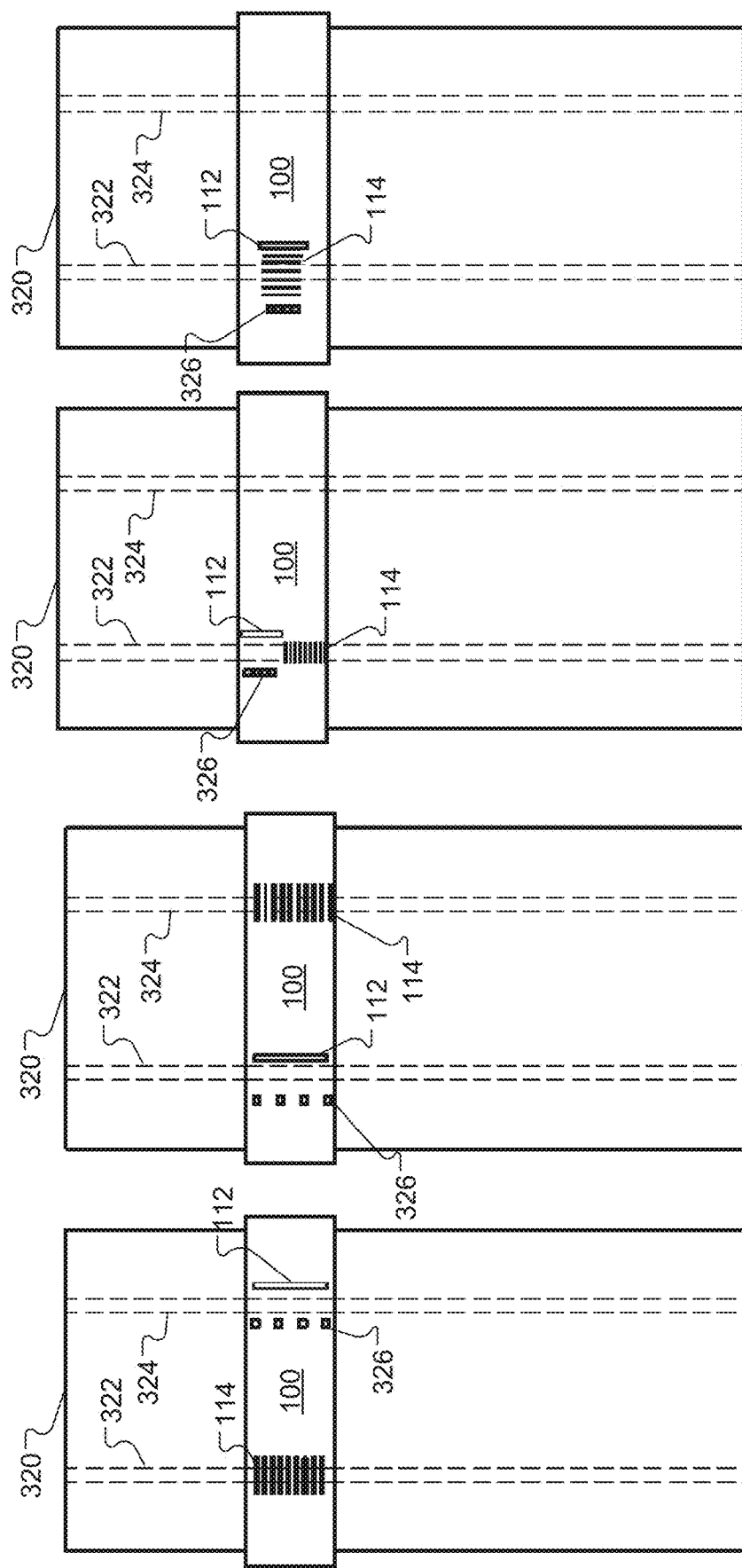

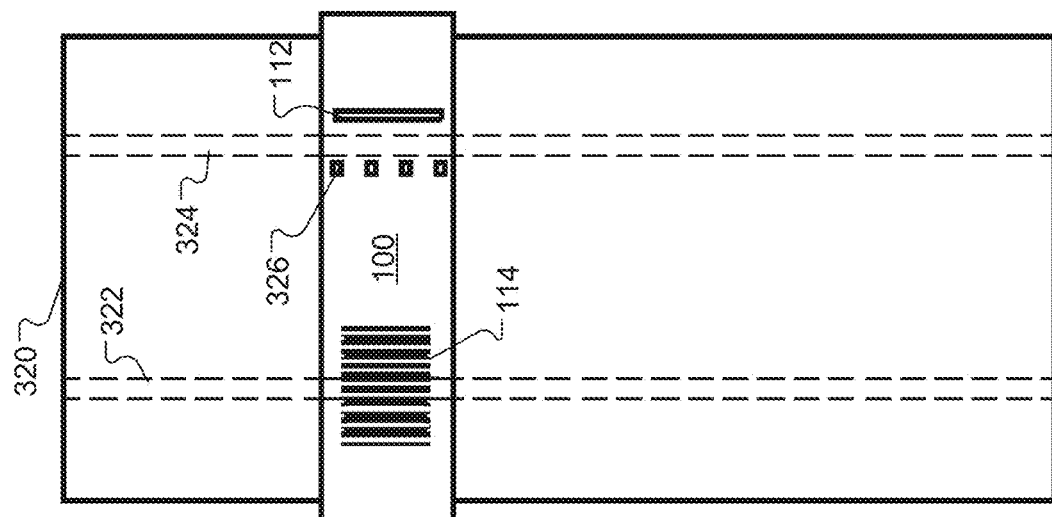
FIG. 3H
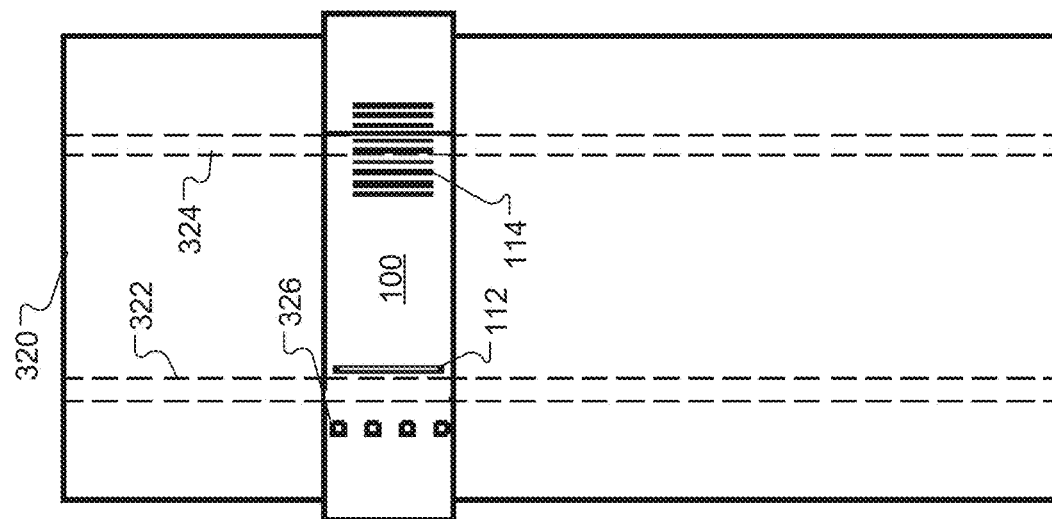
FIG. 3G
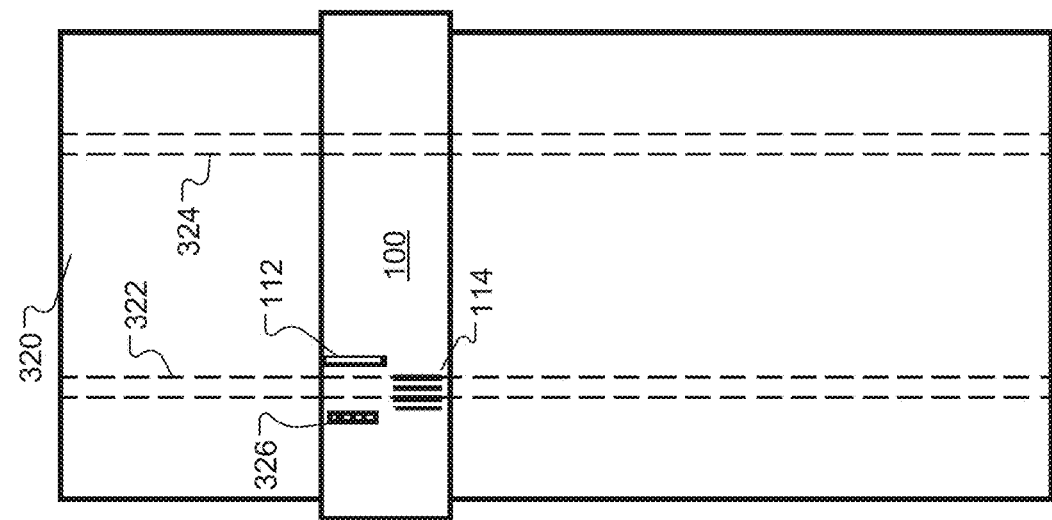
FIG. 3F
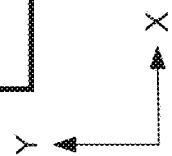

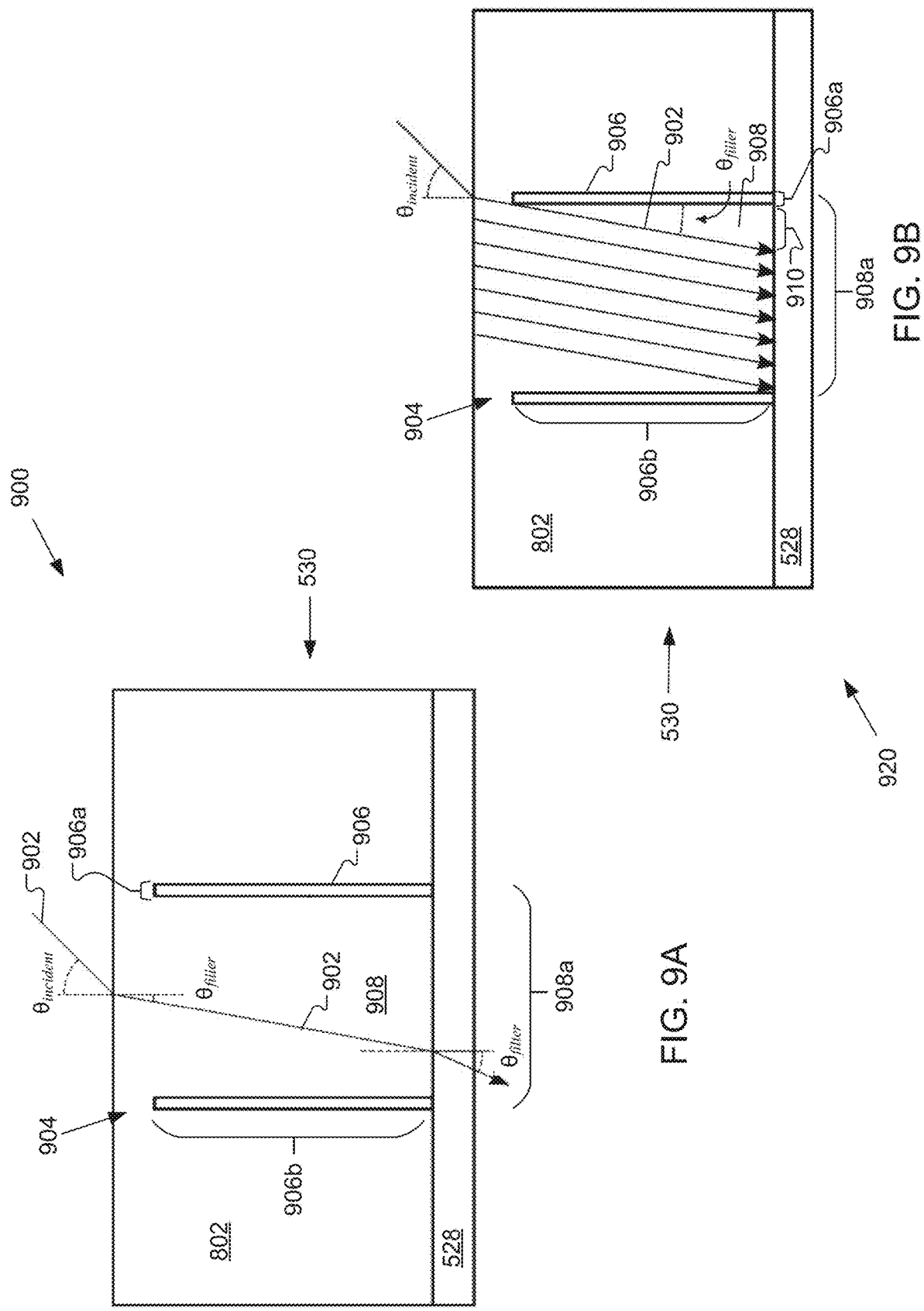

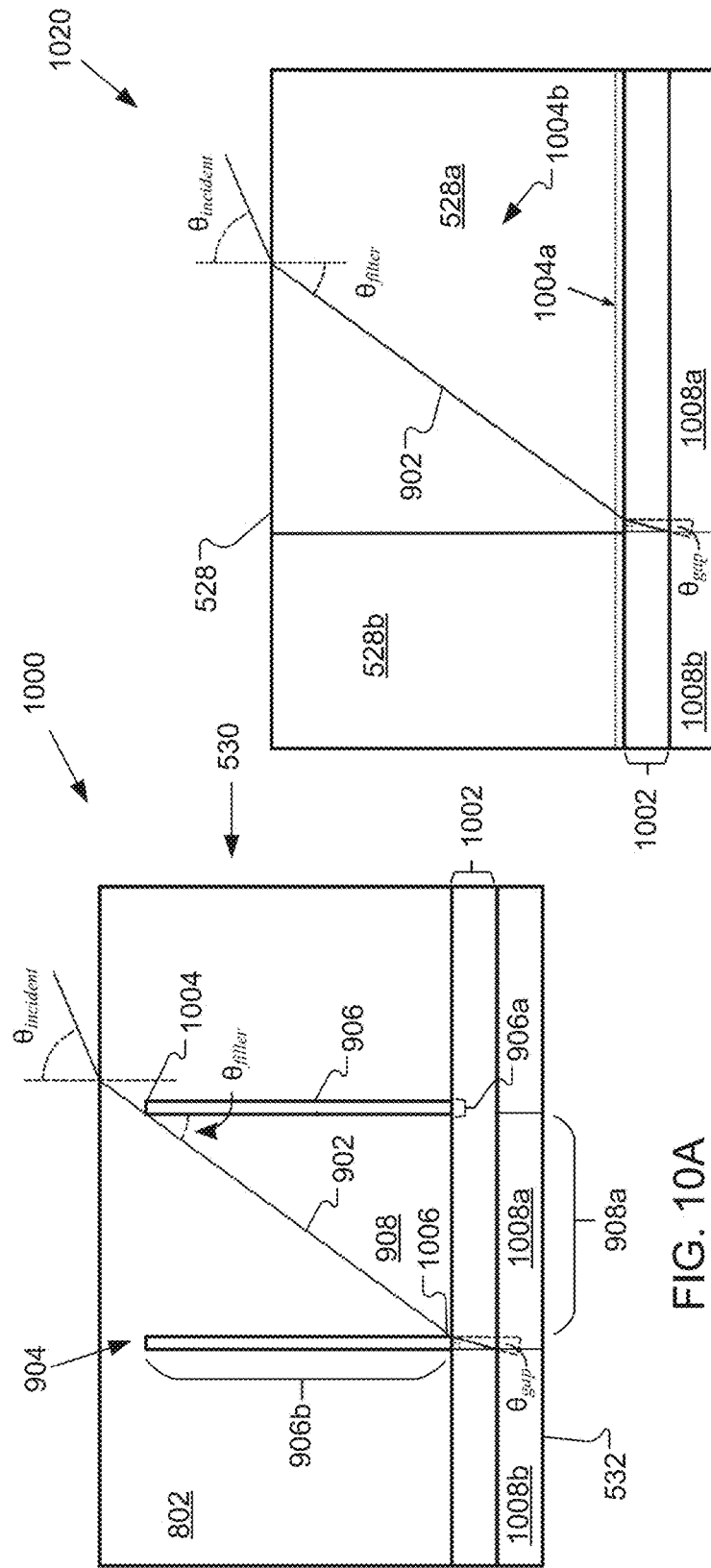
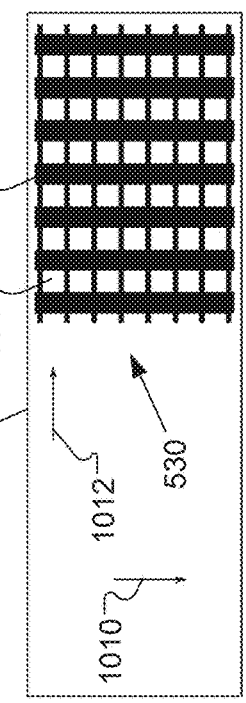
FIG. 10A
FIG. 10B
FIG. 10C

MINIATURIZED COLLIMATORS

BACKGROUND

Spectral or optical spectroscopy is the analysis of the emission, absorption, and reflection of light by matter. Different types of matter absorb and reflect light differently. For example, a spectral analysis of living tissue can be used to detect various forms of cancer and other types of diseases. In this example, spectral analysis includes illuminating a tissue region under examination with light and using a light detector to detect and analyze the optical properties of the illuminated tissue region by measuring light energy modified by its interaction with the tissue region. In this example, the diseased tissue may be identified by comparing the optical properties of normal tissue with the optical properties of disease tissue.

BRIEF DESCRIPTION OF THE DRAWINGS

The present description will be understood more fully from the detailed description given below and from the accompanying drawings of various embodiments of the present embodiment, which description is not to be taken to limit the present embodiment to the specific embodiments but are for explanation and understanding. Throughout the description the drawings may be referred to as drawings, figures, and/or FIGs.

FIG. 3B illustrates the wearable device with the second sensor being located approximate the first muscular-walled tube and the light source and the first sensor being located approximate the second muscular-walled tube, according to an embodiment.

FIG. 3C illustrates the wearable device with the second sensor being located approximate the second muscular-walled tube and the light source and the first sensor being located approximate the first muscular-walled tube, according to an embodiment.

FIG. 3D illustrates the wearable device with the light source, the first sensor, and the second sensor being located longitudinally and approximate the first muscular-walled tube, according to an embodiment.

FIG. 3E illustrates the wearable device with the light source, the first sensor, and the second sensor being located laterally and approximate the first muscular-walled tube, according to an embodiment.

FIG. 3F illustrates the wearable device with the light source, the first sensor, and the second sensor being located in parallel and approximate the first muscular-walled tube, according to an embodiment.

FIG. 3G illustrates the wearable device with the light source and the first sensor being located approximate the first muscular-walled tube and the second sensor being located approximate the second muscular-walled tube, according to an embodiment.

FIG. 3H illustrates the wearable device with the light source and the first sensor being located approximate the second muscular-walled tube and the second sensor being located approximate the first muscular-walled tube, according to an embodiment.

FIG. 9A illustrates a ray diagram of light passing through one or more layers of a miniaturized spectrometer, according to an embodiment.

FIG. 9B illustrates a ray diagram showing a shadow effect of the collimator on light passing through the miniaturized spectrometer, according to an embodiment.

FIG. 10A illustrates a ray diagram that correlates a gap between a collimator and an optical sensor of a miniaturized spectrometer with a region on the optical sensor light may impinge, according to an embodiment.

FIG. 10B illustrates a ray diagram that correlates a gap between a filter and an optical sensor of a miniaturized spectrometer with the region on the optical sensor light may impinge, according to an embodiment.

FIG. 10C illustrates an orientation and structure of a collimator relative to a filter that may reduce and/or eliminate crossing of light to a neighboring sensor segment, according to an embodiment.

DETAILED DESCRIPTION

Figure 1:
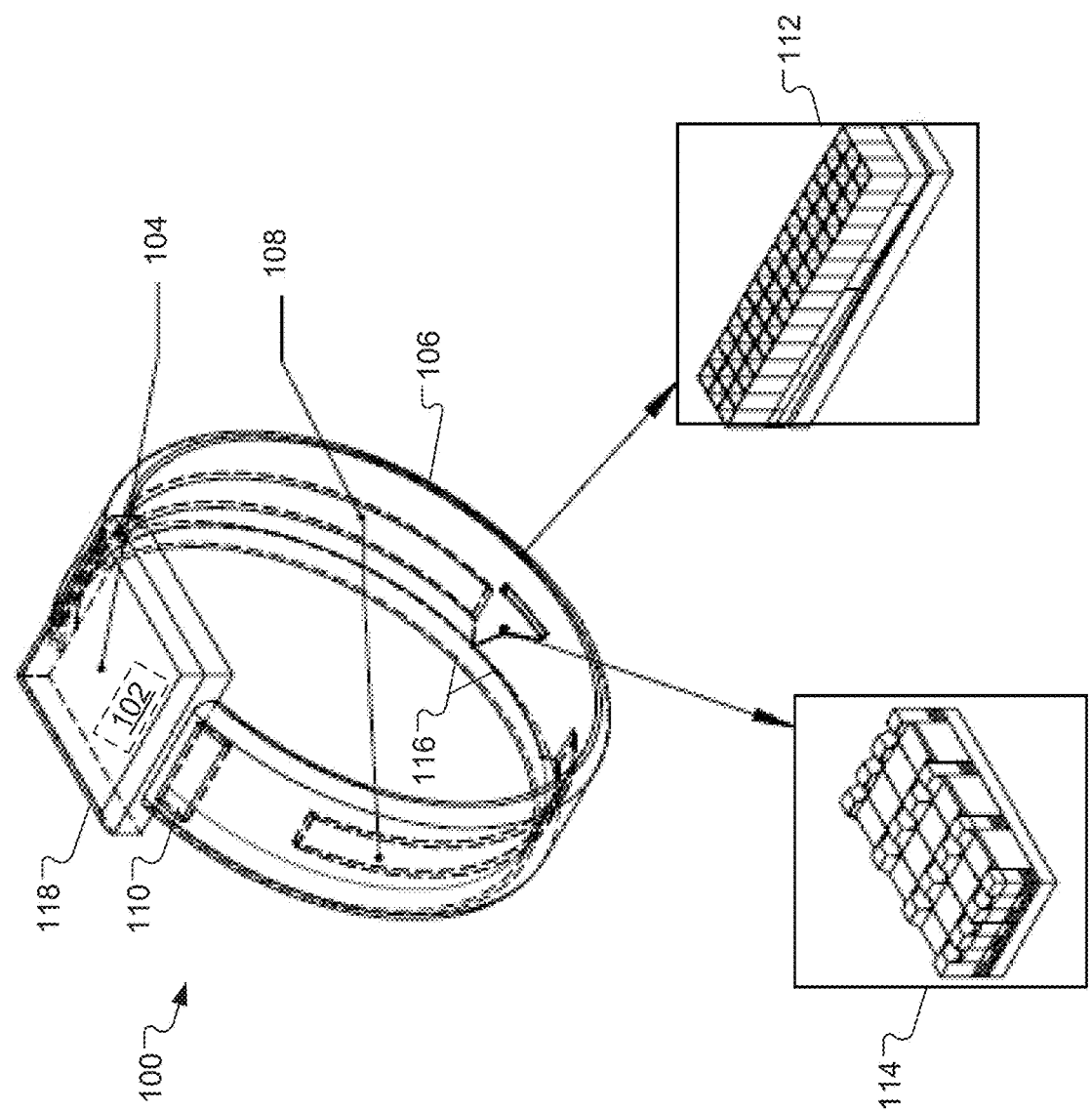
FIG. 1 illustrates a wearable device with integrated sensors, according to an embodiment.

A miniaturized spectrometer as disclosed herein will become better understood through a review of the following detailed description in conjunction with the figures. The detailed description and figures provide merely examples of the various embodiments described herein. Those skilled in the art will understand that the disclosed examples may be varied, modified, and altered and not depart from the scope of the embodiments described herein. Many variations are contemplated for different applications and design considerations; however, for the sake of brevity, the contemplated variations may not be individually described in the following detailed description.

Throughout the following detailed description, examples of various miniaturized spectrometers are provided. Related features in the examples may be identical, similar, or dissimilar in different examples. For the sake of brevity, related features will not be redundantly explained in multiple examples. Instead, the use of a same, similar, and/or related element names and/or reference characters may cue the reader that an element with a given name and/or associated reference character may be similar to another related element with the same, similar, and/or related element name and/or reference character in an example embodiment explained elsewhere herein. Elements specific to a given example may be described regarding that particular example embodiment. A person having ordinary skill in the art will understand that a given element need not be the same or similar to the specific portrayal of a related element in any given figure or example embodiment in order to share features of the related element.

As used herein "same" means sharing all features and "similar" means sharing a substantial number of features or sharing materially important features even if a substantial number of features are not shared. As used herein "may" should be interpreted in the permissive sense and should not be interpreted in the indefinite senses. Additionally, and use of "is" regarding embodiments, elements, and/or features should be interpreted to be definite only regarding a specific embodiment and should not be interpreted as definite regarding the invention as a whole.

Where multiples of a particular element are shown in a FIG., and where it is clear that the element is duplicated throughout the FIG., only one label may be provided for the element, despite multiple instances of the element being present in the FIG. Accordingly, other instances in the FIG. of the element having identical or similar structure and/or function may not have been redundantly labeled. A person having ordinary skill in the art will recognize based on the disclosure herein redundant and/or duplicated elements of the same FIG. Despite this, redundant labeling may be included where helpful in clarifying the structure of the depicted example embodiments.

A spectral or optical spectrometer is an optical instrument for measuring and examining the spectral characteristics of the input light over an electromagnetic spectrum. A conventional optical spectrometer may include a light source, a collimator, a wavelength selector, and a detector. The conventional optical spectrometer may include an entrance slit through which optical beams are fed into the spectrometer. In conventional spectrometers, to maximize the throughput efficiency, the apertures of the optical elements within the spectrometer must be large enough to accept full optical beams without truncation in order to have a three-dimensional propagation path. The detector converts optical signals to electronic signals. However, all the parts of the conventional spectrometer combine into a cumbersome and complex structure that is large in body volume and heavy in weight. The structure of the conventional spectrometer limits the minimum size and weight of the spectrometer because the structure requires a minimum amount of distance between the parts of the spectrometer to allow the light to be properly dispersed into different wavelengths for analysis. A conventional spectrometer may include a lens that may collimate light directed to a photodetector in the spectrometer. The lens may have astigmatism which may limit an intensity of collimated light striking the detector and/or may limit the ability of the spectrometer to separate light into distinct wavelengths. Furthermore, as the structure of the conventional spectrometer is reduced in size and volume, the fidelity and resolution of the spectral analysis decreases exponentially.

Implementations of the disclosure address the above-mentioned deficiencies and other deficiencies by providing methods, systems, devices, or apparatuses to measure and examine the spectral characteristics of the light over an electromagnetic spectrum. In one embodiment, the miniaturized spectrometer may include a light source, a nano-collimator, a miniaturized wavelength selector, and a miniaturized detector. The miniaturized spectrometer may include a carbon nanotube (CNT) collimator that is on a nanoscale. The light source may emit light including one or more wavelengths. The miniaturized spectrometer may be integrated into a wearable device. For example, the miniaturized spectrometer may be integrated into a wristband of a wearable device. The wearable device may include a watch, and the miniaturized spectrometer may be integrated into a band of the watch. The miniaturized spectrometer may be configured to continuously or semi-continuously measure and examine the spectral characteristics of the light over an electromagnetic spectrum. The light may pass directly from the light source to the detector or may pass indirectly through a substance and be reflected towards the detector. An advantage of the miniaturized spectrometer is a simplified optical system that is reduced in body volume and weight while maintaining high fidelity and resolution of the optical characteristics of the detected light. Another advantage of the miniaturized spectrometer is to provide a spectrometer that may be integrated into portable electronic devices to provide ease of use. Another advantage of the miniaturized spectrometer is to provide a portable spectrometer that may be used to continuously or semi-continuously monitor light.

FIG. 1 illustrates a wearable device 100 with integrated sensors 112 and/or 114, according to an embodiment. The elements and/or features described regarding FIG. 1 may be the same as and/or similar to other similarly named elements and/or features described and/or illustrated throughout this disclosure. In one embodiment, the wearable device 100 may be configured to take physiological measurements of a user. The wearable device 100 may include a housing 118 and an attachment mechanism 106, such as a band, that are configured or shaped to attach to a body of the user. In one embodiment, the wearable device 100 may be a wrist worn device that may be configured to attach to a wrist or arm of the user. In one example, the integrated sensors 112 and/or 114 may be positioned against an inside region of the wrist when the user wears the wearable device 100. The inside region of the wrist may face towards the user in a natural resting position. In another example, when the integrated sensors 112 and/or 114 may be positioned against an inside region of the body part, such as the wrist, the integrated sensors 112 and/or 114 may be positioned adjacent to, approximate to, or directly over a muscular-walled tube that is closest to an outer surface of the body part. In another embodiment, the wearable device 100 may be attached to a head of the user using a headband, to a chest of the user using a chest band, to an ankle of the user using an ankle band, or otherwise attached to a body of the user using a sweatband, bandage, band, watch, bracelet, ring, adherent, or other attachments and connections.

In various embodiments, the housing 118 may be moveably coupled to the band 106. In one example, the band 106 may be a flexible band designed to flex into a curvilinear shape. The flexible band with a shape, size, and/or flexibility designed for attaching the band 106 to a wrist of a user. The wrist may include a dermal layer along an underside of the wrist and a muscular-walled tube within the wrist adjacent to the dermal layer along the underside of the wrist. The housing 118 may be configured with external electrical contacts. The band 106 may be configured with multiple contact points or a continuous contact strip. The housing 118 may be coupled to the band 106 such that the external electrical contacts of the housing 118 form electrical contact with the one or more of the multiple contact points or the continuous contact strip of the band 106. The housing 118 may be moved on the band 106 to a different position and still maintain electrical communication with electrical components embedded in the band 106 such as the electrical trace or circuit 116, the first sensor 112, or the second sensor 114.

The wearable device 100 may include a processing device 102, a user interface or display device 104, the band 106, a power source 108, a processing unit 110, the first sensor 112, and/or the second sensor 114. In one embodiment, the processing device 102, the user interface or display device 104, the power source 108, the processing unit 110, the first sensor 112, and/or the second sensor 114 may be electronically coupled and/or communicatively coupled. In another embodiment, the processing device 102 and the display device 104 may be integrated into the housing 118 of the wearable device 100. In another embodiment, the power source 108, the processing unit 110, the first sensor 112, and/or the second sensor 114 may be integrated into the band 106 of the wearable device 100. In one embodiment, the first sensor 112 and/or the second sensor 114 may be integrated or positioned along an inside surface or interior surface of the band 106, such that the first sensor 112 and/or the second sensor 114 may be flush with the surface of the band 106 to contact a body part of a user when worn or protrude from a surface of the band 106 to extend toward a surface of the body part of the user when worn. In another embodiment, the band 106 may include a cavity that the power source 108, the processing unit 110, the first sensor 112, and/or the second sensor 114 may be stored in. In another embodiment, the band 106 may be formed or molded over the power source 108, the processing unit 110, the first sensor 112, and/or the second sensor 114. In another embodiment, the power source 108, the first sensor 112, and/or the second sensor 114 may be connected to the processing unit 110 and/or the processing device 102 by one or more electrical trace(s) or circuit(s) 116 (such as flexible circuit boards).

In one embodiment, the first sensor 112 may be a miniaturized spectrometer. The miniaturized spectrometer may include a carbon-nanotube structure forming a collimator, an optical filter, and a photodetector stacked together and embedded in the band 106. The photodetector may be positioned in the band 106 to face the user's body part 320 when the user wears the band 106. In another embodiment, the second sensor 114 may be a miniaturized impedance sensor. In another embodiment, the first sensor 112 and/or the second sensor may be a temperature sensor, a viscosity sensor, an ultrasonic sensor, a humidity sensor, a heart rate sensor, a dietary intake sensor, an electrocardiogram (EKG) sensor, an ECG sensor, a galvanic skin response sensor, a pulse oximeter, an optical sensor, and so forth. In another embodiment, the wearable device 100 may include other sensors integrated or attached to the band 106 or the housing 118. In another embodiment, the wearable device 100 may be communicatively coupled to the wearable device 100, such as sensors of other devices or third-party devices.

The first sensor 112 and/or the second sensor 114 may be coupled to the processing unit 110. The processing unit 110 may be configured to manage or control the first sensor 112, the second sensor 114, and/or the power source 108. In one embodiment, the processing unit 110 may control a frequency or rate over time that the first sensor 112 and/or the second sensor 114 take measurements, a wavelength or optical frequency at which the first sensor 112 and/or the second sensor 114 take measurements, a power consumption level of the first sensor 112 and/or the second sensor 114, a sleep mode of the first sensor 112 and/or the second sensor 114 and so forth. In another embodiment, the processing unit 110 may control or adjust measurements taken by the first sensor 112 and/or the second sensor 114 take measurements to remove noise, increase a signal to noise ratio, dynamically adjust the amount of measurements taken over time, and so forth.

In another embodiment, the power source 108 may be coupled to the processing unit 110. The power source 108 may be a battery, a solar panel, a kinetic energy device, a heat converter power device, a wireless power receiver, and so forth. The processing unit 110 may be configured to transfer power from the power source 108 to the processing device 102, the display device 104, the first sensor 112, the second sensor 114, and/or other devices or units of the wearable device 100. In one embodiment, the processing unit 110 may be configured to regulate an amount of power provided from the power source 108 to the processing device 102, the display device 104, the first sensor 112, the second sensor 114, and/or other devices or units of the wearable device 100. In another embodiment, the wearable device 100 may include a power receiver to receive power to recharge the power source 108. For example, the power receiver may be a wireless power coil, a universal serial bus (USB) connector, a thunderbolt connector, a mini USB connector, a micro USB connector, a USB-C connector, and so forth. The power receiver may be coupled to the processing unit 110, the processing device 102, the power source 108, and so forth. In one embodiment, the processing unit 110 may be configured to regulate an amount of power provided from the power receiver to the power source 108. In another embodiment, the processing unit 110 may be a power management unit configured to control battery management, voltage regulation, charging functions, direct current (DC) to DC conversion, voltage scaling, power conversion, dynamic frequency scaling, pulse-frequency modulation (PFM), pulse-width modulation (PWM), amplification, and so forth. In another embodiment, the processing unit 110 may include a communication device configured to send and/or receive data via a cellular communication channel, a wireless communication channel, a Bluetooth® communication channel, a radio communication channel, a WiFi® communication channel, and so forth.

The processing device 102 may include a processor, a data storage device, a communication device, a graphics processor, and so forth. In one embodiment, the processing device 102 may be coupled to the processing unit 110, the power source 108, the first sensor 112, and/or the second sensor 114. In one embodiment, the processing device 102 may be configured to receive measurement data from the processing unit 110, the first sensor 112, and/or the second sensor 114. In one embodiment, the processing device 102 may be configured to process the measurement data and display information associated with the measurement data at the display device 104. In another embodiment, the processing device 102 may be configured to communicate the measurement data to another device. In one embodiment, the other device may process the measurement data and provide information associated with the measurement data to the user or another individual. In another embodiment, the other device may process the measurement data and provide results, analytic information, instructions, and/or notifications to the processing device 102 to provide to the user. The wearable device 100 may communicate information associated with the measurement data or information related to the measurement data to a user via the display device 104, a buzzer, a vibrator, a speaker, a microphone, and so forth. In one example, the display device 104 may include an input device, such as a button, a touch screen, a touch display, an so forth that may receive an input form the user.

In another embodiment, the wearable device 100 may be part of a system connected to other devices. For example, the wearable device 100 may be configured to send and/or receive data with another device. In one embodiment, the wearable device 100 may be configured to receive data from another measurement device, aggregate the received data with measurement data from the first sensor 112 and/or the second sensor 114, analyze the aggregated data, and provide information or notifications associated with the analyzed data.

Figure 2A:
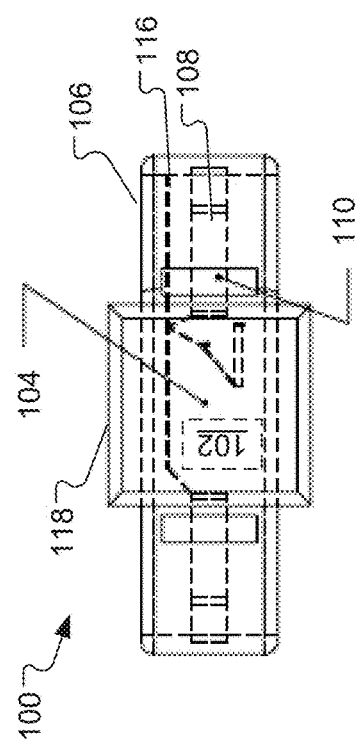
FIG. 2A illustrates a top exposed view of the wearable device described and illustrated regarding FIG. 1, according to an embodiment.
Figure 2B:
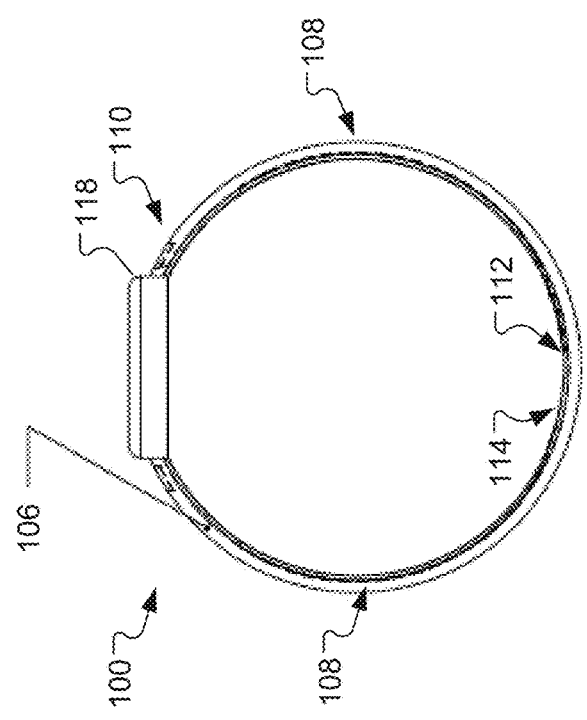
FIG. 2B illustrates a profile view of the wearable device, according to an embodiment.
Figure 2C:
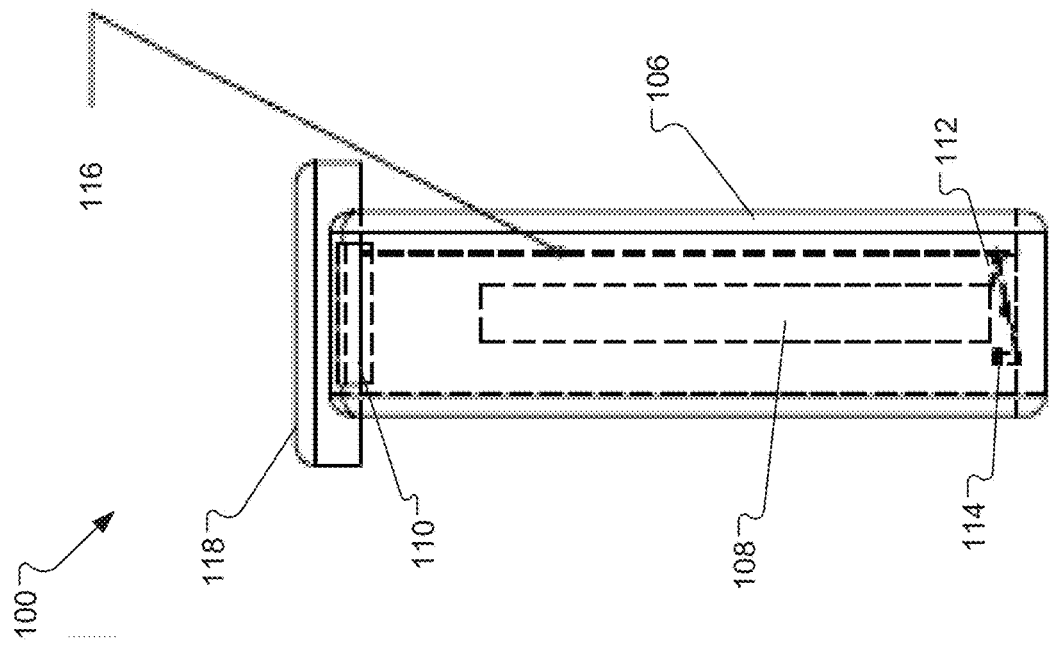
FIG. 2C illustrates a side view of the wearable device, according to an embodiment.

FIGS. 2A-C illustrate side and top views of a wearable device 100, according to an embodiment. FIG. 2A illustrates a top exposed view of the wearable device 100 in FIG. 1, according to an embodiment. Some of the features in FIG. 2A are the same as or similar to some of the features in FIG. 1 as noted by same and/or similar reference characters, unless expressly described otherwise. Furthermore, the elements and/or features described regarding FIG. 2A may be the same as and/or similar to other similarly named elements and/or features described and/or illustrated throughout this disclosure. As discussed above, the wearable device 100 may be a wrist-worn device that may be configured to attach to a wrist of a user. As further discussed above, the processing device 102 and the display device 104 may be integrated into the housing 118 of the wearable device 100 and the power source 108, the processing unit 110, the first sensor 112, and/or the second sensor 114 may be integrated into the band 106 of the wearable device 100. In one embodiment, the band 106 may include a cavity that the power source 108, the processing unit 110, the first sensor 112, and/or the second sensor 114 may be stored in. In another embodiment, the band 106 may be formed or molded over the power source 108, the processing unit 110, the first sensor 112, and/or the second sensor 114. In various embodiments, the band 106 may be formed of silicone and/or canvas material.

FIG. 2B illustrates a profile view of the wearable device 100, according to an embodiment. Some of the features in FIG. 2B are the same as or similar to some of the features in FIGS. 1 and FIG. 2A as noted by same and/or similar reference characters, unless expressly described otherwise. Furthermore, the elements and/or features described regarding FIG. 2B may be the same as and/or similar to other similarly named elements and/or features described and/or illustrated throughout this disclosure. In one embodiment, the housing 118 with the processing device 102 and the display device 104 (as shown in FIGS. 1 and 2A) may be located at a top of the wearable device 100 such that the housing 118 may be located at a top surface of a wrist of a user when the user wears the wearable device 100 on their wrist. In another embodiment, the first sensor 112 and/or the second sensor 114 (as shown in FIGS. 1 and 2A) may be located at a bottom of the wearable device 100 such that the first sensor 112 and/or the second sensor 114 may be located at a bottom surface of a wrist of a user when the user wears the wearable device 100 on their wrist. In another embodiment, the power source 108 and/or the processing unit 110 (as shown in FIGS. 1 and 2A) may be located along a side of the wearable device 100 such that the power source 108 and/or the processing unit 110 may be located at a side surface of a wrist of a user when the user wears the wearable device 100 on their wrist.

FIG. 2C illustrates a side view of the wearable device 100, according to an embodiment. Some of the features in FIG. 2C are the same or similar to some of the features in FIGS. 1-2B as noted by same reference characters, unless expressly described otherwise. As discussed above, the wearable device 100 may include the power source 108, the processing unit 110, the first sensor 112, and/or the second sensor 114. In another embodiment, the power source 108, the first sensor 112, and/or the second sensor 114 may be connected to the processing unit 110 and/or the processing device 102 by one or more electrical trace(s) or circuit(s) 116. In one embodiment, the electrical trace 116 may extend at least partially along a circumference of the band 106. In one embodiment, the power source 108 may be located on one or both sides of the band 106, the first sensor 112 and/or the second sensor 114 may be located at a bottom of the band, and the processing unit 110 may be located at a side or a top of the band 106 (such as approximate the housing 118). In one embodiment, the electrical trace(s) 116 may extend along a circumference of the band 106 along a side or middle circumference of the band 106. The electrical trace(s) 116 may transfer data and/or power between the power source 108, the first sensor 112, the second sensor 114, the processing unit 110, the processing device 102 (as shown in FIG. 1), and/or the display device 104 (as shown in FIG. 1).

Figure 3A:
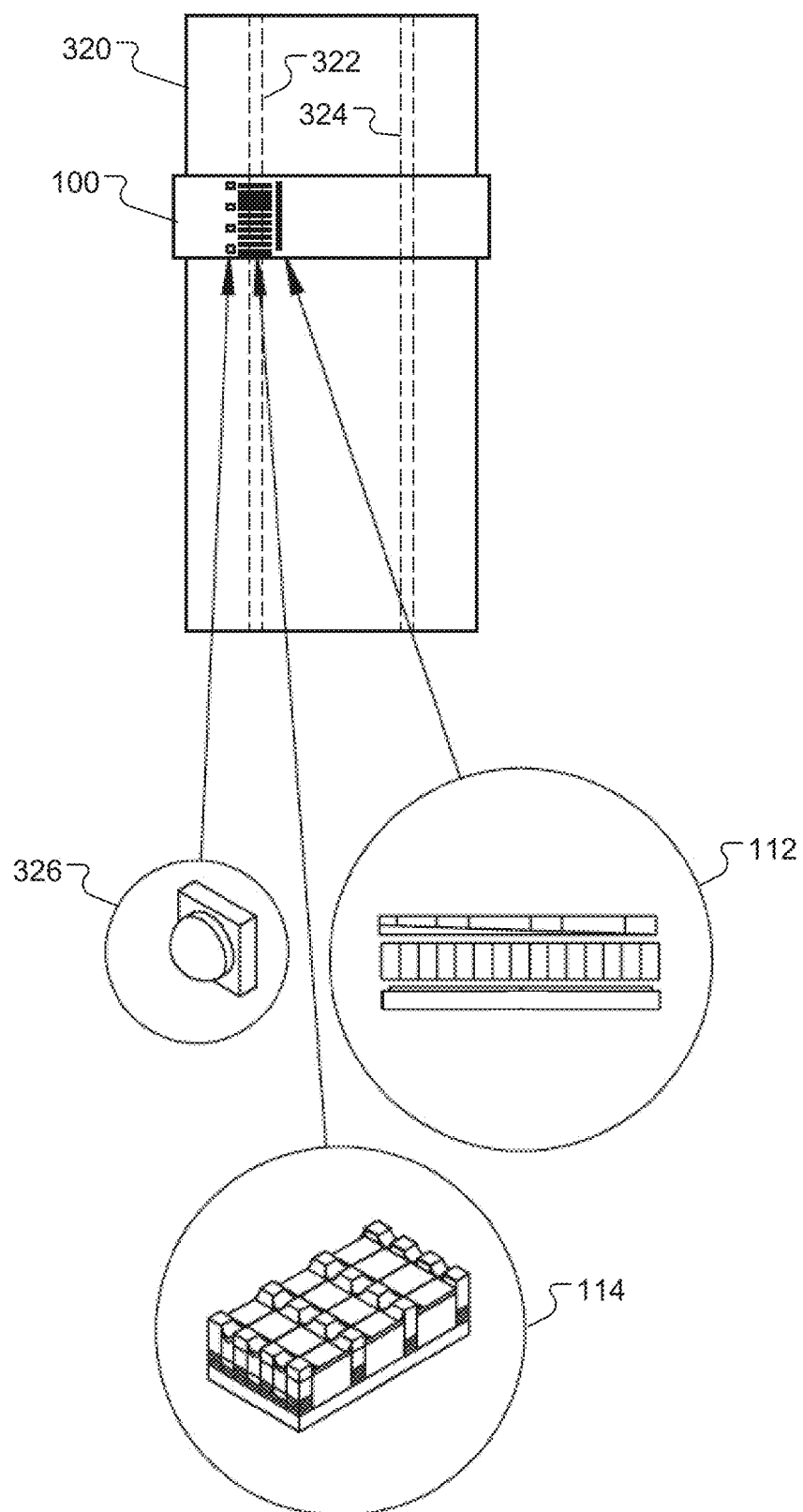
FIG. 3A illustrates the wearable device attached to a part of a body of an individual, according to an embodiment.

FIGS. 3A-H illustrate various embodiments of the wearable device 100 positioned on a user relative to veins and/or arteries of the user, according to various embodiments. FIG. 3A illustrates the wearable device 100 attached to a part of a body 320 of an individual, according to an embodiment. Some of the features in FIG. 3A are the same as or similar to some of the features in FIGS. 1-2B as noted by same and/or similar reference characters, unless expressly described otherwise. Furthermore, the elements and/or features described regarding FIG. 3A may be the same as and/or similar to other similarly named elements and/or features described and/or illustrated throughout this disclosure. In one embodiment, the wearable device 100 may be attached to the part of the body 320 of the individual. The part of the body 320 may be an arm, a leg, a hand, a wrist, a head, an appendage, and so forth of the body 320 of the individual. For example, the wearable device 100 may be attached to a wrist or arm of the body 320 of the individual. As discussed above, the wearable device 100 may include the first sensor 112 and/or the second sensor 114. In another embodiment, the first sensor 112 and or the second sensor 114 may be attached to a band of the wearable device 100 such that the first sensor 112 and/or the second sensor 114 may be aligned over a muscular-walled tube 322 and/or 324 of the body 320 of the individual. The muscular-walled tube 322 and/or 324 may be a vein, an artery, or other tubes or channels to circulate fluids in the body 320, such as blood, water, oxygen, and so forth. For example, the first muscular-walled tube 322 may be an ulnar artery or vein and the second muscular-walled tube 324 may be a radial artery or vein.

In one embodiment, the wearable device 100 may include one or more light sources 326 integrated into the band of the wearable device 100 such that the light sources 326 are offset to a first side of the first muscular-walled tube 322 and extend horizontally along surface of the skin offset to the muscular-walled tube 322. The light source(s) 326 may be light emitting diodes (LEDs), incandescent bulbs, tungsten bulbs, lasers, and so forth. In one embodiment, the wearable device 100 may include the first sensor 112 integrated into the band of the wearable device 100 such that the first sensor 112 may be offset to a second side of the muscular-walled tube 322 and extend horizontally along surface of the skin offset to the muscular-walled tube 322. In one embodiment, the light sources 326 may be located at a first side of the muscular-walled tube 322 and the first sensor 112 may be located opposite to the light sources 326 on the other side of the muscular-walled tube 322. In another embodiment, the second sensor 114 may be a miniaturized impedance sensor that may be positioned over top of the muscular-walled tube 322. The muscular-walled tube may include a blood vessel such as a vein or artery in an arm or wrist of a body 320 of the user, such as a human body. In one embodiment, the second sensor 114 may be integrated into the band of the wearable device 100 such that the second sensor 114 may run parallel to and extend horizontally along surface of the skin above the muscular-walled tube 322.

The first sensor 112 and the second sensor 114 may be compactly arranged in the wearable device 100. The close proximity of the first sensor 112, the second sensor 114, and/or the light source 326 may reduce an amount of wiring disbursed throughout the wearable device 100. The first sensor 112, the second sensor 114, and/or the light source 326 may be integrated into and/or on a single substrate. The substrate may be flexible and/or rigid. Compact arrangement of the sensors may allow for use of a rigid substrate, which may increase the durability of the sensors and/or the wearable device 100 overall. Compact arrangement of the sensor may also allow for consistency of measurement. In various embodiments, such as embodiments discussed regarding FIG. 26, measurements of multiple sensors may be correlated and/or aggregated. Compact arrangement may allow for measurement by multiple sensors of the same muscular-walled tube 322 at the same or roughly the same location on the muscular-walled tube. This may increase the precision of correlations and/or aggregations.

FIG. 3B illustrates the wearable device 100 with the second sensor 114 being located approximate the first muscular-walled tube 322 and the light source 326 and the first sensor 112 being located approximate the second muscular-walled tube 324, according to an embodiment. Some of the features in FIG. 3B are the same as or similar to some of the features in FIGS. 1-3A as noted by same and/or similar reference characters, unless expressly described otherwise. Furthermore, the elements and/or features described regarding FIG. 3B may be the same as and/or similar to other similarly named elements and/or features described and/or illustrated throughout this disclosure. In one embodiment, the second sensor 114 may be located over the first muscular-walled tube 322. In one embodiment, the second sensor 114 may include a miniaturized impedance sensor. In one embodiment, the first muscular-walled tube 322 may extend along a Y-axis of a first plane and the miniaturized impedance sensor may extend perpendicularly relative to the first muscular-walled tube 322 along an X-axis of a second plane, such that the miniaturized impedance sensor extends from a first side of the first muscular-walled tube 322 to a second side of the first muscular-walled tube 322. In another embodiment, the first sensor 112 may be located at a first side of the second muscular-walled tube 324 and the light source(s) 326 may be located on a second side of the second muscular-walled tube 324, such that the first sensor 112 and the light source(s) 326 straddle each side of second muscular-walled tube 324.

FIG. 3C illustrates the wearable device 100 with the second sensor 114 being located approximate the second muscular-walled tube 324 and the light source 326 and the first sensor 112 being located approximate the first muscular-walled tube 322, according to an embodiment. Some of the features in FIG. 3C are the same as or similar to some of the features in FIGS. 1-3B as noted by same and/or similar reference characters, unless expressly described otherwise. Furthermore, the elements and/or features described regarding FIG. 3C may be the same as and/or similar to other similarly named elements and/or features described and/or illustrated throughout this disclosure. In one embodiment, the second sensor 114 may be located over the second muscular-walled tube 324. In one embodiment, the second sensor 114 may include a miniaturized impedance sensor. In one embodiment, the second muscular-walled tube 324 may extend along a Y-axis of a first plane and the miniaturized impedance sensor may extend perpendicularly relative to the second muscular-walled tube 324 along an X-axis of a second plane, such that the miniaturized impedance sensor may extend from a first side of the second muscular-walled tube 324 to a second side of the second muscular-walled tube 324. In another embodiment, the first sensor 112 may be located at a first side of the first muscular-walled tube 322 and the light source(s) 326 may be located on a second side of the first muscular-walled tube 322, such that the first sensor 112 and the light source(s) 326 straddle each side of first muscular-walled tube 322.

The embodiments illustrated in FIGS. 3B-C generally illustrate embodiments where the first sensor 112 is placed to take measurements near and/or from one muscular-walled tube, and the second sensor 114 is placed to take measurements near and/or from another muscular-walled tube. The two muscular-walled tubes may have different features corresponding to different physiological conditions, physiological parameters, and/or physiological constituents. The two muscular-walled tubes may have different features corresponding to a change in a physiological condition, physiological parameter, and/or physiological constituent. For example, one of the muscular-walled tubes may be a vein, and the other muscular-walled tube may be an artery. In general, arteries may carry oxygenated blood, and veins may carry deoxygenated blood. In the embodiments illustrated in FIGS. 3B-C, the arrangements of the sensor may allow for correlation of oxygenated blood to deoxygenated blood. This in turn may inform a determination of a physiological condition, physiological parameter, and/or physiological constituent of a user of the wearable device 100. For example, the wearable device 100 may include the processing unit 110, which may correlate measurements taken by the first sensor 112 and the second sensor 114 placed over the first muscular-walled tube 322 and the second muscular-walled tube 324, respectively, to determine that the blood is not being sufficiently oxygenated.

FIG. 3D illustrates the wearable device 100 with the light source 326, the first sensor 112, and the second sensor 114 being located longitudinally and approximate the first muscular-walled tube 322, according to an embodiment. Some of the features in FIG. 3D are the same as or similar to some of the features in FIGS. 1-3C as noted by same and/or similar reference characters, unless expressly described otherwise. Furthermore, the elements and/or features described regarding FIG. 3D may be the same as and/or similar to other similarly named elements and/or features described and/or illustrated throughout this disclosure. In one embodiment, the first sensor 112 may be located at a first side of a first location along the first muscular-walled tube 322 and the light source(s) 326 may be located on a second side of the first location along the first muscular-walled tube 322, such that the first sensor 112 and the light source(s) 326 straddle each side of the first location along the first muscular-walled tube 322. In another embodiment, the second sensor 114 may be located over a second location along the first muscular-walled tube 322. In another embodiment, the second sensor 114 may include a miniaturized impedance sensor. In one embodiment, the first muscular-walled tube 322 may extend along a Y-axis of a first plane and the miniaturized impedance sensor may extend perpendicularly relative to the first muscular-walled tube 322 along an X-axis of a second plane, such that the miniaturized impedance sensor may extend from a first side of the first muscular-walled tube 322 to a second side of the first muscular-walled tube 322. In one embodiment, the first location along the first muscular-walled tube 322 may be located above or ahead of the second location along the first muscular-walled tube 322 along the Y-axis. In another embodiment, the first location along the first muscular-walled tube 322 may be located below or behind of the second location along the first muscular-walled tube 322 along the Y-axis.

FIGS. 3A-D generally show the second sensor 114 aligned with its length parallel to the length of the muscular-walled tubes. Parallel alignment of the second sensor 114 to the muscular-walled tubes may allow for measurements and/or characterization of features running parallel to the length of the muscular-walled tubes. For example, in embodiments where the second sensor 114 includes the miniaturized impedance sensor, the current passed into the user by the miniaturized impedance sensor may run parallel or roughly parallel to the length of the muscular-walled tube to which the miniaturized impedance sensor corresponds. In an embodiment where the muscular-walled tube includes a vein or artery, parallel alignment of the miniaturized impedance sensor may allow for measurement and/or characterization of the blood in the vein or artery along a path of the blood in the vein or artery. Similarly, parallel alignment of the miniaturized impedance sensor may allow for measurement and/or characterization of the muscular-walled tube along the length of the muscular-walled tube.

FIG. 3E illustrates the wearable device 100 with the light source 326, the first sensor 112, and the second sensor 114 being located laterally and approximate the first muscular-walled tube 322, according to an embodiment. Some of the features in FIG. 3E are the same as or similar to some of the features in FIGS. 1-3D as noted by same and/or similar reference characters, unless expressly described otherwise. Furthermore, the elements and/or features described regarding FIG. 3E may be the same as and/or similar to other similarly named elements and/or features described and/or illustrated throughout this disclosure. In one embodiment, the first sensor 112 may be located at a first side of a location along the first muscular-walled tube 322 and the light source(s) 326 may be located on a second side of the location along the first muscular-walled tube 322, such that the first sensor 112 and the light source(s) 326 may straddle each side of the first location along the first muscular-walled tube 322. In another embodiment, the second sensor 114 may be located over the same location along the first muscular-walled tube 322. In another embodiment, the second sensor 114 may include a miniaturized impedance sensor. In one embodiment, the light source 326, the first sensor 112, and the second sensor 114 may extend laterally along the X-axis and perpendicularly to the muscular-walled tube 322. In one embodiment, the second sensor 114 may be located between the light source 326 and the first sensor 112. In another embodiment, the second sensor 114 may be located at an exterior side of the light source 326 or the first sensor 112. In another embodiment, a first portion of the second sensor 114 may be located at an exterior side of the light source 326 and a second portion of the second sensor 114 may be located at an exterior side of the first sensor 112.

Perpendicular alignment of the second sensor 114 to the muscular-walled tubes may allow for measurements and/or characterization of features running perpendicular to the length of the muscular-walled tubes. For example, in embodiments where the second sensor 114 includes the miniaturized impedance sensor, the current passed into the user by the miniaturized impedance sensor may run perpendicular or roughly perpendicular to the length of the muscular-walled tube to which the miniaturized impedance sensor corresponds. In an embodiment where the muscular-walled tube includes a vein or artery, perpendicular alignment of the miniaturized impedance sensor may allow for measurement and/or characterization of a cross-sectional area of the blood in the vein or artery. Similarly, perpendicular alignment of the miniaturized impedance sensor may allow for measurement and/or characterization of the muscular-walled tube along the circumference and/or diameter of the muscular-walled tube.

FIG. 3F illustrates the wearable device 100 with the light source 326, the first sensor 112, and the second sensor 114 being located in parallel and approximate the first muscular-walled tube 322, according to an embodiment. Some of the features in FIG. 3F are the same as or similar to some of the features in FIGS. 1-3E as noted by same and/or similar reference characters, unless expressly described otherwise. Furthermore, the elements and/or features described regarding FIG. 3F may be the same as and/or similar to other similarly named elements and/or features described and/or illustrated throughout this disclosure. In one embodiment, the first sensor 112 may be located at a first side of a first location along the first muscular-walled tube 322 and the light source(s) 326 may be located on a second side of the first location along the first muscular-walled tube 322, such that the first sensor 112 and the light source(s) 326 may straddle each side of the first location along the first muscular-walled tube 322. In another embodiment, the second sensor 114 may be located over a second location along the first muscular-walled tube 322. In another embodiment, the second sensor 114 may include a miniaturized impedance sensor. In one embodiment, the first muscular-walled tube 322 may extend along a Y-axis of a first plane and the impedance pad(s) may extend parallel to the first muscular-walled tube 322 along a Y-axis of a second plane, such that the impedance pad(s) extend along a portion of the first muscular-walled tube 322. In one embodiment, the first location along the first muscular-walled tube 322 may be located above or ahead of the second location along the first muscular-walled tube 322 along the Y-axis. In another embodiment, the first location along the first muscular-walled tube 322 may be located below or behind of the second location along the first muscular-walled tube 322 along the Y-axis.

FIG. 3G illustrates the wearable device 100 with the light source 326 and the first sensor 112 being located approximate the first muscular-walled tube 322 and the second sensor 114 being located approximate the second muscular-walled tube 324, according to an embodiment. Some of the features in FIG. 3G are the same as or similar to some of the features in FIGS. 1-3F as noted by same and/or similar reference characters, unless expressly described otherwise. Furthermore, the elements and/or features described regarding FIG. 3G may be the same as and/or similar to other similarly named elements and/or features described and/or illustrated throughout this disclosure. In one embodiment, the second sensor 114 may be located over the second muscular-walled tube 324. In one embodiment, the second sensor 114 may include a miniaturized impedance sensor. In one embodiment, the second muscular-walled tube 324 may extend along a Y-axis of a first plane and the miniaturized impedance sensor may extend parallel relative to the second muscular-walled tube 324 along a Y-axis of a second plane, such that the miniaturized impedance sensor may extend along a portion of the second muscular-walled tube 324. In another embodiment, the first sensor 112 may be located at a first side of the first muscular-walled tube 322 and the light source(s) 326 may be located on a second side of the first muscular-walled tube 322, such that the first sensor 112 and the light source(s) 326 may straddle each side of first muscular-walled tube 322.

FIG. 3H illustrates the wearable device 100 with the light source 326 and the first sensor 112 being located approximate the second muscular-walled tube 324 and the second sensor 114 being located approximate the first muscular-walled tube 322, according to an embodiment. Some of the features in FIG. 3H are the same as or similar to some of the features in FIGS. 1-3G as noted by same and/or similar reference characters, unless expressly described otherwise. Furthermore, the elements and/or features described regarding FIG. 3H may be the same as and/or similar to other similarly named elements and/or features described and/or illustrated throughout this disclosure. In one embodiment, the second sensor 114 may be located over the first muscular-walled tube 322. In one embodiment, the second sensor 114 may include a miniaturized impedance sensor. In one embodiment, the second muscular-walled tube 324 may extend along a Y-axis of a first plane and the miniaturized impedance sensor may extend parallel relative to the first muscular-walled tube 322 along a Y-axis of a second plane, such that the miniaturized impedance sensor may extend along a portion of the second muscular-walled tube 324. In another embodiment, the first sensor 112 may be located at a first side of the second muscular-walled tube 324 and the light source(s) 326 may be located on a second side of the second muscular-walled tube 324, such that the first sensor 112 and the light source(s) 326 may straddle each side of second muscular-walled tube 324.

FIGS. 3A-H illustrate the first sensor 112 and the light source 326 straddling the muscular-walled tube 322 and/or the muscular-walled tube 324. Such an arrangement may allow for precise detection by the first sensor 112 of light scattered by the muscular-walled tube 322 and/or the muscular-walled tube 324. The arrangement may also reduce interference by and/or detection of light scattered by other structures within the part of the body 320 to ensure a measurement taken by the first sensor 112 corresponds to light scattered by the muscular-walled tube 322 and/or the muscular-walled tube 324. A separation distance between the first sensor 112 and the light source 326 may also minimize an amount of light scattered by a surface of the part of the body 320 such as skin on the part of the body 320. In an embodiment, a curvature of the part of the body 320 may also allow for light from the light source 326 to pass more directly to the first sensor 112 as the light source 326 and the first sensor 112 straddle the muscular-walled tube 322 and/or the muscular-walled tube 324. In an embodiment, the first sensor 112 may include a miniaturized spectrometer. The miniaturized spectrometer may collimate light that passes into the miniaturized spectrometer, which may result in a decreased intensity of light striking a photosensor within the miniaturized spectrometer as tangential light rays are absorbed, reflected, and/or otherwise deflected away from the photosensor. However, as the light source 326 and the first sensor 112 straddle the muscular-walled tube 322 and/or the muscular-walled tube 324 and the curvature of the part of the body 320 aligns light emitted from the light source 326 more directly with the first sensor 112, an amount and therefore intensity of the light impinging on the first sensor 112 may increase.

Figure 3J:
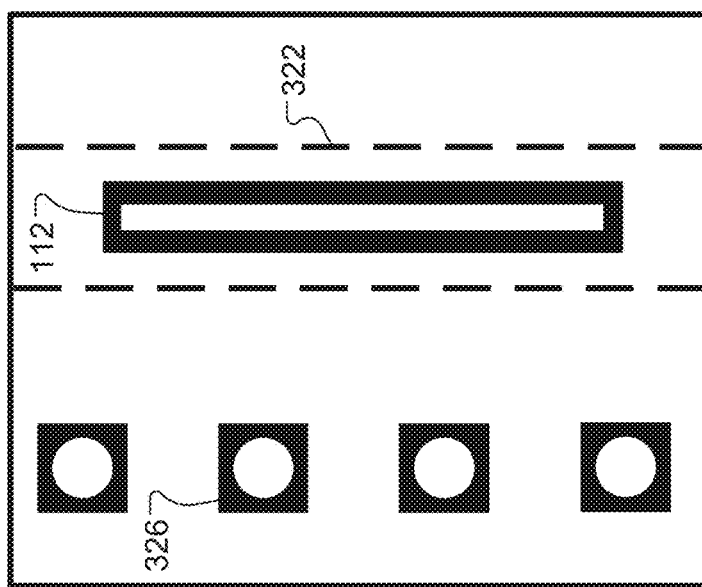
FIG. 3J illustrates a zoomed-in view of the wearable device similar to FIG. 3I, with the first sensor positioned over the first muscular-walled tube, according to an embodiment.
Figure 3I:
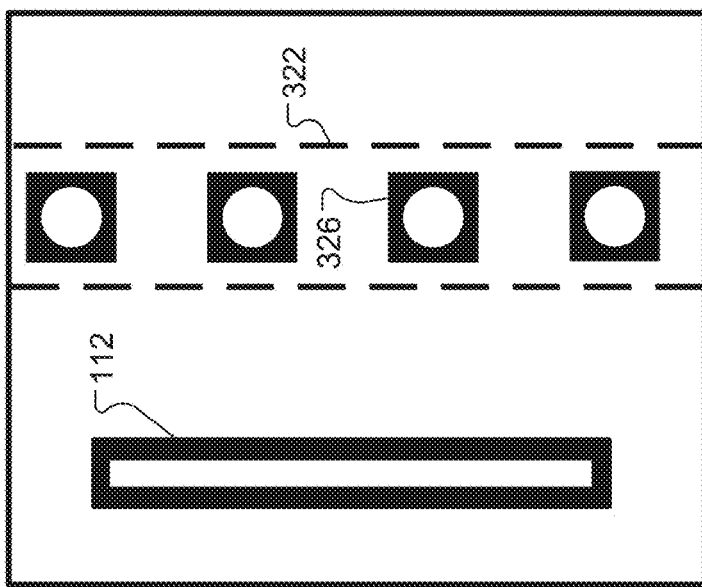
FIG. 3I illustrates a zoomed-in view of the wearable device, focusing in on the first sensor, the light source, and the first muscular-walled tube, with the light source positioned over the first muscular-walled tube, according to an embodiment.

FIG. 3I illustrates a zoomed-in view of the wearable device 100, focusing in on the first sensor 112, the light source 326, and the first muscular-walled tube 322, according to an embodiment. Some of the features in 3I are the same as or similar to some of the features in FIGS. 1-3H as noted by same reference characters, unless expressly described otherwise. The light source 326 may be positioned over the muscular-walled tube. In an embodiment, a plurality of light sources 326 may be positioned over the muscular-walled tube. The first muscular-walled tube 322 may extend along a Y-axis of a first plane and the plurality of light sources 326 may extend over the muscular-walled tube 322 along the Y-axis. The first sensor 112 may be positioned approximate the muscular-walled tube 322. In an embodiment, the first sensor 112 may include a miniaturized spectrometer. The miniaturized spectrometer may have a length along the Y-axis that is greater than a length of the miniaturized spectrometer along an X-axis of the first plane. The arrangement of the light source 326 over the first muscular-walled tube 322 may allow for direct illumination of the first muscular-walled tube 322 by the light source 326. This may increase the amount of light scattered from the first muscular-walled tube 322 and/or received by the first sensor 112 relative to embodiments where the light source 326 is not positioned over the first muscular-walled tube 322.

FIG. 3J illustrates another zoomed-in view of the wearable device 100, focusing in on the first sensor 112, the light source 326, and the first muscular-walled tube 322, according to an embodiment. Some of the features in 3J are the same as or similar to some of the features in FIGS. 1-3I as noted by same reference characters, unless expressly described otherwise. The first sensor 112 may be positioned over the muscular-walled tube. The first muscular-walled tube 322 may extend along a Y-axis of a first. In an embodiment, the first sensor 112 may include a miniaturized spectrometer. The miniaturized spectrometer may have a length along the Y-axis that is greater than a length of the miniaturized spectrometer along an X-axis of the first plane. The miniaturized spectrometer may accordingly be aligned over the first muscular-walled tube 322 parallel or roughly parallel to a length of the first muscular-walled tube 322 along the Y-axis. In an embodiment, the wearable device 100 includes a plurality of light sources 326. The plurality of light sources 326 may be positioned approximate the first muscular-walled tube 322. The plurality of light sources 326 may be arranged in order along the Y-axis. The arrangement of the miniaturized spectrometer over the first muscular-walled tube 322 may allow for greater capture of light reflected by the first muscular-walled tube 322 relative to embodiments where the miniaturized spectrometer is not positioned over and/or aligned along with the first muscular-walled tube 322.

In an embodiment, the wearable device 100 may include a flexible band such as the band 106, the light source 326, an optical sensor, an optical filter, and a collimator. The optical sensor, the optical filter, and/or the collimator may be integrated together to form a miniaturized spectrometer, such as the first sensor 112. The flexible band may be configured to extend at least partially around a wrist of the user, such as the body part 320. The wrist may include a dermal layer along an underside of the wrist and the muscular-walled tube 322 or 324 within the wrist adjacent to the dermal layer along the underside of the wrist. T light source 326 may be embedded in the flexible band and positioned in the flexible band to emit light into the wrist through the dermal layer along the underside of the wrist as the user wears the flexible band. The light source may be positioned in the flexible band to be pressed into the wrist along a first side of the muscular-walled tube 322 or 324 as the user wears the flexible band. The optical sensor may be embedded in the flexible band and positioned in the flexible band to be situated, as the user wears the flexible band, along a second side of the muscular-walled tube 322 or 324 opposite the first side of the muscular-walled tube 322 or 324. The optical filter may be integrated into the flexible band and may be configured to isolate a relevant constituent wavelength of the light. The optical filter may be positioned in the flexible band to filter the light emitted by the light source 326 before the light passes to the optical sensor. The collimator may be integrated into the flexible band and positioned in the flexible band to be situated, as the user wears the flexible band, along the second side of the muscular-walled tube 322 or 324. The collimator may be positioned in the flexible band to collimate the light emitted by the light source 326 before the light passes to the optical sensor. The miniaturized spectrometer, with the optical sensor, the optical filter, and/or the collimator may be embedded in the flexible band to be situated along the second side of the muscular-walled tube opposite the light source such that the light source 326 and the miniaturized spectrometer straddle the muscular-walled tube 322 or 324.

In one example of the embodiment, the flexible band may include a first end and a second end, and a clasp configured to join the first end to the second end, or to join the first end or the second end to the flexible band. The light source 326 and the miniaturized spectrometer may be positioned in the flexible band adjacent to the clasp. The flexible band may be configured to press the light source 326 or the miniaturized spectrometer against the wrist of the user as the user wears the flexible band. The flexible band may prevent the light source 326 from being displaced from the first side of the muscular-walled tube 322 or 324 as the user wears the flexible band. The flexible band may prevent the miniaturized spectrometer from being displaced from the second side of the muscular-walled tube 322 or 324 as the user wears the flexible band.

In another example, the wearable device 100 may include user interface 104 coupled to the flexible band and positioned on the flexible band to be situated along a top side of the wrist opposite the underside of the wrist as the user wears the flexible band. The position of the user interface 104 on the flexible band may correspond to a natural alignment of the user interface 104 on the top side of the wrist for the user to interact with the user interface 104 as the user wears the flexible band. The light source 326 and the miniaturized spectrometer may be positioned in the flexible band to straddle the muscular-walled tube 322 or 324 as the user interface 104 is positioned in the natural alignment as the user wears the flexible band. The muscular-walled tube 322 or 324 may include an ulnar artery or a radial artery of the user. The natural alignment of the user interface on the wrist may align the light source and the miniaturized spectrometer to straddle the ulnar artery or the radial artery as the user wears the flexible band. An axis may extend along a width of the flexible band opposite the user interface 104. The light source 326 may be positioned in the flexible band at a first side of the axis. The miniaturized spectrometer may be positioned in the flexible band at a second side of the axis.

In another example, the relevant constituent wavelength may an indicator of an amount of glucose in blood flowing through the muscular-walled tube 322 or 324 as the user wears the flexible band.

In an example, the miniaturized spectrometer may be positioned in the flexible band to receive reflected light through the dermal layer as the user wears the flexible band. The reflected light may be reflected by the muscular-walled tube 322 or 324 or a material within the muscular-walled tube.

In an example, the light source 326 may be isolated from the miniaturized spectrometer. The flexible band may be configured in flexibility, size, or durability to press the light source 326 and the miniaturized spectrometer against the wrist as the user wears the flexible band. The flexible band and the dermal layer may create a first optical seal around the light source 326 as the user wears the flexible band such that the light emitted from the light source is directed into the wrist. The flexible band and the dermal layer may create a second optical seal around the miniaturized spectrometer as the user wears the flexible band such that the miniaturized spectrometer is isolated from external light external to the wrist of the user.

In an example, the light source 326 may include a length and a width, and the flexible band may include a length and a width. The light source 326 may be oriented in the flexible band such that the light source 326 length is perpendicular to the band 106 length. The orientation of the light source 326 may align the light source 326 approximately parallel to the muscular-walled tube 322 or 324 as the user wears the flexible band to emit light through a plurality of positions along a length of the muscular-walled tube 322 or 324. Similarly, the miniaturized spectrometer may include a length and a width. The miniaturized spectrometer may be oriented in the flexible band such that the spectrometer length is perpendicular to the band 106 length. The orientation of the miniaturized spectrometer may align the miniaturized spectrometer approximately parallel to the muscular-walled tube 322 or 324 as the user wears the flexible band to receive the light emitted by the light source 326 through a plurality of positions along a length of the muscular-walled tube 22 or 324.

In an embodiment, the wearable device 100 may include the band 106, the light source 326, the optical sensor, the optical filter, and the collimator. The optical sensor, the optical filter, and/or the collimator may be integrated together to form a miniaturized spectrometer such as the first sensor 112. The band 106 may be configured to extend at least partially around the body part 320 of the user. The body part 320 may include a dermal layer around the body part 320 and the muscular-walled tube 322 or 324 within the body part 320 adjacent to the dermal layer. The light source 326 may be integrated into the band 106. The light source 326 may be positioned in the band 106 to emit light into the body part 320 through the dermal layer as the user wears the band 106. The light source 326 may be positioned in the band 106 to be pressed against the dermal layer over the muscular-walled tube 322 or 324 as the user wears the band 106 such that the dermal layer is situated directly between the muscular-walled tube 322 or 324 and the light source 106. The light source 326 may be positioned along a first side of the muscular-walled tube 322 or 324 as the user wears the band 106. The optical filter may be integrated into the band 106. The optical filter may be configured to isolate a relevant constituent wavelength of the light. The optical filter may be positioned in the band to filter the light emitted by the light source 326 before the light passes to the optical sensor. The collimator may be positioned relative to the optical sensor to collimate the light emitted by the light source 326 before the light passes to the optical sensor. The miniaturized spectrometer may be integrated into the band 106 to be situated along a first side of the muscular-walled tube 322 or 324 adjacent to the light source. 326

In an example of the embodiment, the light source 326 may include a length and a width, and the band 106 may include a length and a width. The light source 326 may be oriented in the band 106 such that the light source 326 length is perpendicular to the band 106 length. The orientation of the light source 326 may align the light source 326 approximately parallel to the muscular-walled tube 322 or 324 as the user wears the band 106 to emit light along a length of the muscular-walled tube 322 or 324.

In another example, the band 106 may form a shape, the shape being approximately circular or approximately elliptical. The light source 326 may be positioned in the band 106 along a same side of the band 106 as the miniaturized spectrometer. The wearable device 100 may include the user interface 104 coupled to the band 106. The user interface 104 may be positioned on the band 106 along an opposite side of the band 106 from the light source 326 or the miniaturized spectrometer when the user wears the band 106. The light source 326 and the miniaturized spectrometer may face inwards into the band 106 and the user interface 104 may face outwards from the band 106.

In one embodiment, the wearable device 100 may include the band 106, the light source 326, the optical sensor, the optical filter, and the collimator. The optical sensor, the optical filter, and/or the collimator may be integrated together to form the miniaturized spectrometer. The band 106 may be configured to extend at least partially around the body part 320 of the user. The body part 320 may include a dermal layer around the body part 320 and a subdermal feature within the body part adjacent to the dermal layer. The light source 326 may be integrated into the band 106. The light source 326 may be positioned in the band 106 to emit light into the body part through the dermal layer as the user wears the band 106. The optical filter may be integrated into the band. The optical filter may be configured to isolate a relevant constituent wavelength of the light. The optical filter may be positioned in the band 106 to filter the light emitted by the light source 326 before the light passes to the optical sensor. The collimator may be positioned relative to the optical sensor to collimate the light emitted by the light source 326 before the light passes to the optical sensor. The miniaturized spectrometer may be positioned in the band 106 to be situated adjacent to the dermal layer over the subdermal feature as the user wears the band 106 such that the dermal layer is situated directly between the subdermal feature and the miniaturized spectrometer as the user wears the band 106.

In an example of the embodiment, the light source 326 may be positioned in the band 106 adjacent to the miniaturized spectrometer along a length of the band 106 such that, as the user wears the band 106, the light source 326 is positioned along the dermal layer offset from the subdermal feature. The light source 326 may be positioned in the band 106 adjacent to the miniaturized spectrometer along a width of the band 106 such that, as the user wears the band 106, the light source 326 is positioned along the dermal layer over the subdermal feature. The dermal layer may be situated directly between the light source 326 and the subdermal feature.

In another example, the wearable device 100 may include the user interface 104 coupled to the band 106 and an axis extending along a width of the band 106 directly opposite the user interface 104. The light source 326 and the miniaturized spectrometer may be off-centered in the band 106 relative to the user interface 104 such that the light source 326 and the miniaturized spectrometer may be positioned in the band 106 along a first side of the axis closer to a first side of the user interface 104 along the band 106 than to a second side of the user interface 104 along the band 106. The light source 326 and the miniaturized spectrometer may be aligned in the band 106 approximately parallel to each other.

In another embodiment, the wearable device 100 may include a flexible band such as the band 106, the user interface 104, the light source 326, a miniaturized spectrometer such as the first sensor 112, an impedance sensor such as the second sensor 114, and the processing device 102. The flexible band may be designed to flex into a curvilinear shape, and may include a shape, size, and flexibility designed for attaching the flexible band to a wrist of the user, such as the body part 320. The wrist may include a dermal layer along an underside of the wrist and the muscular-walled tube 322 or 324 within the wrist adjacent to the dermal layer along the underside of the wrist. The user interface 104 may be coupled to the flexible band and positioned on the flexible band to be situated, as the user wears the flexible band, adjacent to a top side of the wrist opposite the underside of the wrist. The light source 326 may be embedded in the flexible band. The light source 326 may be positioned in the flexible band to emit light into the wrist through the dermal layer along the underside of the wrist as the user wears the flexible band. The miniaturized spectrometer may be embedded in the flexible band and positioned in the flexible band to press against the underside of the wrist as the user wears the flexible band to receive the light through the dermal layer. The miniaturized spectrometer may include an optical filter, a collimator, and/or an optical sensor. The optical filter may be configured to isolate a relevant constituent wavelength of the light. The relevant constituent wavelength may indicate a feature of the muscular-walled tube 322 or 324 or of blood flowing through the muscular-walled tube 322 or 324. The collimator may be configured to collimate the light received by the miniaturized spectrometer. The optical sensor may be configured to detect an intensity of the relevant constituent wavelength. The impedance sensor may be embedded in the flexible band and positioned in the flexible band to be situated, as the user wears the flexible band, against the underside of the wrist. The impedance sensor may include two or more rows of microelectrodes. The processing device 102 may be coupled to the flexible band and communicatively coupled to the optical sensor and the impedance sensor. The miniaturized spectrometer and the impedance sensor may be positioned in the flexible band to simultaneously measure, as the user wears the flexible band, the feature of the muscular-walled tube 322 or 324 or of the blood flowing through the muscular-walled tube 322 or 324.

In one example of the embodiment, the impedance sensor may be positioned in the flexible band to be aligned approximately radially with the muscular-walled tube 322 or 324 as the user wears the flexible band. The light source 326 and the miniaturized spectrometer may be positioned in the flexible band to straddle the impedance sensor, the light source 326 positioned along a first side of the impedance sensor, and the miniaturized spectrometer positioned along a second side of the impedance sensor opposite the first side of the impedance sensor. The impedance sensor may be positioned in the flexible band such that the two or more rows of microelectrodes are aligned in the flexible band to be approximately parallel to the muscular-walled tube 322 or 324 or approximately perpendicular to the muscular-walled tube 322 or 324 as the user wears the flexible band.

In another example, the light source 326 may be positioned in the flexible band to be situated along a first side of the muscular-walled tube 322 or 324 against the dermal layer as the user wears the flexible band. The miniaturized spectrometer may be positioned in the flexible band to be situated along a second side of the muscular-walled tube against the dermal layer as the user wears the flexible band. The light source 326 and the miniaturized spectrometer may be positioned in the flexible band to straddle the muscular-walled tube 322 or 324 as the user wears the flexible band. The light source 326 may be positioned along a first side of the muscular-walled tube 322 or 324, and the miniaturized spectrometer may be positioned along a second side of the muscular-walled tube 322 or 324 opposite the first side of the muscular-walled tube. The impedance sensor may be positioned in the flexible band to be aligned approximately radially with a second muscular-walled tube 322 or 324 as the user wears the flexible band. The second muscular-walled tube 322 or 324 may be adjacent to the dermal layer along the underside of the wrist.

In another example, the processing device 102 may be configured to measure blood glucose simultaneously by the miniaturized spectrometer and the impedance sensor. The impedance sensor, the miniaturized spectrometer, and/or the light source 326 may be positioned in the flexible band adjacent to each other. The impedance sensor and the miniaturized spectrometer or the light source 326 are positioned in the flexible band to be aligned approximately radially with the muscular-walled tube 322 or 324 as the user wears the flexible band.

In another example, the processing device 102 may be configured to measure, by the impedance sensor, a hydration condition of the user. The processing device 102 may be configured to measure, by the miniaturized spectrometer, a blood glucose level of the user. The processing device 102 may be configured to adjust a measurement of the blood glucose level of the user based on the hydration condition of the user, where a change in the hydration condition of the user skews the measurement of the blood glucose level.

In another example, the miniaturized spectrometer or the light source 326 may be positioned in the flexible band to be aligned approximately radially with the muscular-walled tube 322 or 324 as the user wears the flexible band. The impedance sensor may be positioned in the flexible band to be aligned approximately radially with the muscular-walled tube 322 or 324 as the user wears the flexible band.

In an embodiment, the wearable device 100 may include the band 106, the light source 326, the miniaturized spectrometer, and the impedance sensor. The band 106 may be configured to extend at least partially around the body part 320 of the user, the body part 320 including a dermal layer and a subdermal feature within body part 320. The light source 326 may be integrated into the band 106, where the light source 326 is configured in the band to emit light into the body part 320 through the dermal layer. The miniaturized spectrometer may be integrated into the band 106 and positioned in the band 106 to press against the body part 320 as the user wears the band 106 to receive the light through the dermal layer. The miniaturized spectrometer may include an optical filter, a collimator, and an optical sensor. The optical filter may be configured to isolate a relevant constituent wavelength of the light, the relevant constituent wavelength indicating a condition or a constituent of the body part 320, the dermal layer, or the subdermal feature. The collimator may be configured to collimate the light received by the miniaturized spectrometer. The optical sensor may be configured to detect an intensity of the relevant constituent wavelength. The impedance sensor may be integrated into the band 106 and configured to be positioned, as the user wears the band, against a same side of the body part 320 as the miniaturized spectrometer. The miniaturized spectrometer may be configured in the band 106 to be positioned along a same side of the body part as the impedance sensor when the user wears the band 106.

In one example of the embodiment, the wearable device 100 may include the processing device 102. The processing device 102 may be configured to take, by the optical sensor, an optical measurement, and take, by the impedance sensor, an impedance measurement simultaneously with the optical measurement. The processing device 102 may be configured to: correlate the impedance measurement and the optical measurement; and determine glucose measurement of the body part 320, the dermal layer, or the subdermal structure based on the correlation. The optical measurement may indicate a change in the glucose measurement, where the change in the glucose measurement is a combination of a change in glucose and a change in hydration in the body part 320, the dermal layer, or the subdermal structure. The impedance measurement may indicate the change in the hydration in the body part 320, the dermal layer, or the subdermal structure. The processing device 102 may be configured to filter out the change in the hydration based on the impedance measurement from the glucose measurement to generate a glucose indicator.

In another example, the miniaturized spectrometer or the impedance sensor may positioned in the band 106 to be situated, as the user wears the band 106, against a region of the dermal layer directly adjacent to the subdermal structure. The body part 320 may be approximately circular, approximately oval-shaped, or approximately elliptical. The body part 320 may include a radius, the subdermal structure being aligned in the body part approximately along the radius. The miniaturized spectrometer or the impedance sensor may be positioned in the band 106 to be aligned, as the user wears the band, radially with the subdermal structure.

In an embodiment, a method of using the wearable device 100 to take a measurement may include placing the wearable device 100 at least partially around the body part 320 of the user, where the wearable device 100 may include structure or programming to take simultaneous measurements of a feature of the body part 320 with two different types of sensors. The wearable device 100 may include the band 106, the light source 326, the miniaturized spectrometer, the impedance sensor, and the processing device 102. The band 106 may be shaped to extend at least partially around the body part 320 of the user. The body part 320 may include a dermal layer, a subdermal structure within body part 320, a first side, and a second side facing a different direction than the first side. The light source 326 may be integrated into the band 320. The light source 326 may be configured in the band 106 to emit light into the body part 320 through the dermal layer. The miniaturized spectrometer may be integrated into the band 106 and positioned in the band 106 to press against the body part 320 as the user wears the band 106 to receive the light through the dermal layer. The miniaturized spectrometer may include the optical filter, the collimator, and the optical sensor. The optical filter may be configured to isolate a relevant constituent wavelength of the light, the relevant constituent wavelength indicating a condition or a constituent of the body part 320, the dermal layer, or the subdermal feature. The collimator may be configured to collimate the light received by the miniaturized spectrometer. The optical sensor may be configured to detect an intensity of the relevant constituent wavelength. The impedance sensor may be integrated into the band 106 and positioned in the band 106 to be situated along a same side of the body part 320 as the miniaturized spectrometer as the user wears the band 106. The same side may include either the first side of the body part 320 or the second side of the body part 320. The processing device 102 may be configured to take simultaneous measurements with the miniaturized spectrometer and the impedance sensor, the processing device communicatively coupled to the impedance sensor and the optical sensor. The method may include: emitting, by the light source, the light through the body part; detecting, by the optical sensor, the relevant constituent wavelength; measuring an impedance of the body part by the impedance sensor simultaneously with the light source emitting the light and the optical sensor detecting the relevant constituent wavelength; and communicating to the processing device an impedance measurement from the impedance sensor and an optical measurement from the optical sensor.

In one example of the embodiment, the method may include comparing the impedance measurement and the optical measurement to determine a feature, a condition, or a constituent of the subdermal structure. The method may include determining, based on the impedance measurement or the optical measurement, an alignment of the wearable device on the body part relative to the subdermal structure. The method may include: determining, by the processing device, a first condition of the body part based on the impedance measurement; determining, by the processing device 102, a second condition of the body part based on the optical measurement; comparing, by the processing device 102 the first condition of the body part with the second condition of the body part; and determining whether the first condition and the second condition are independent conditions or dependent conditions based on the comparison. The method may include aligning the wearable device on the body part 320 such that the impedance sensor or the miniaturized spectrometer are aligned radially with the subdermal structure on the body part 320. The body part may be approximately circular, approximately oval-shaped, or approximately elliptical, and the body part 320 may have a radius extending from a center of the body part outward towards the dermal layer and perpendicular with the dermal layer.

Figure 4:
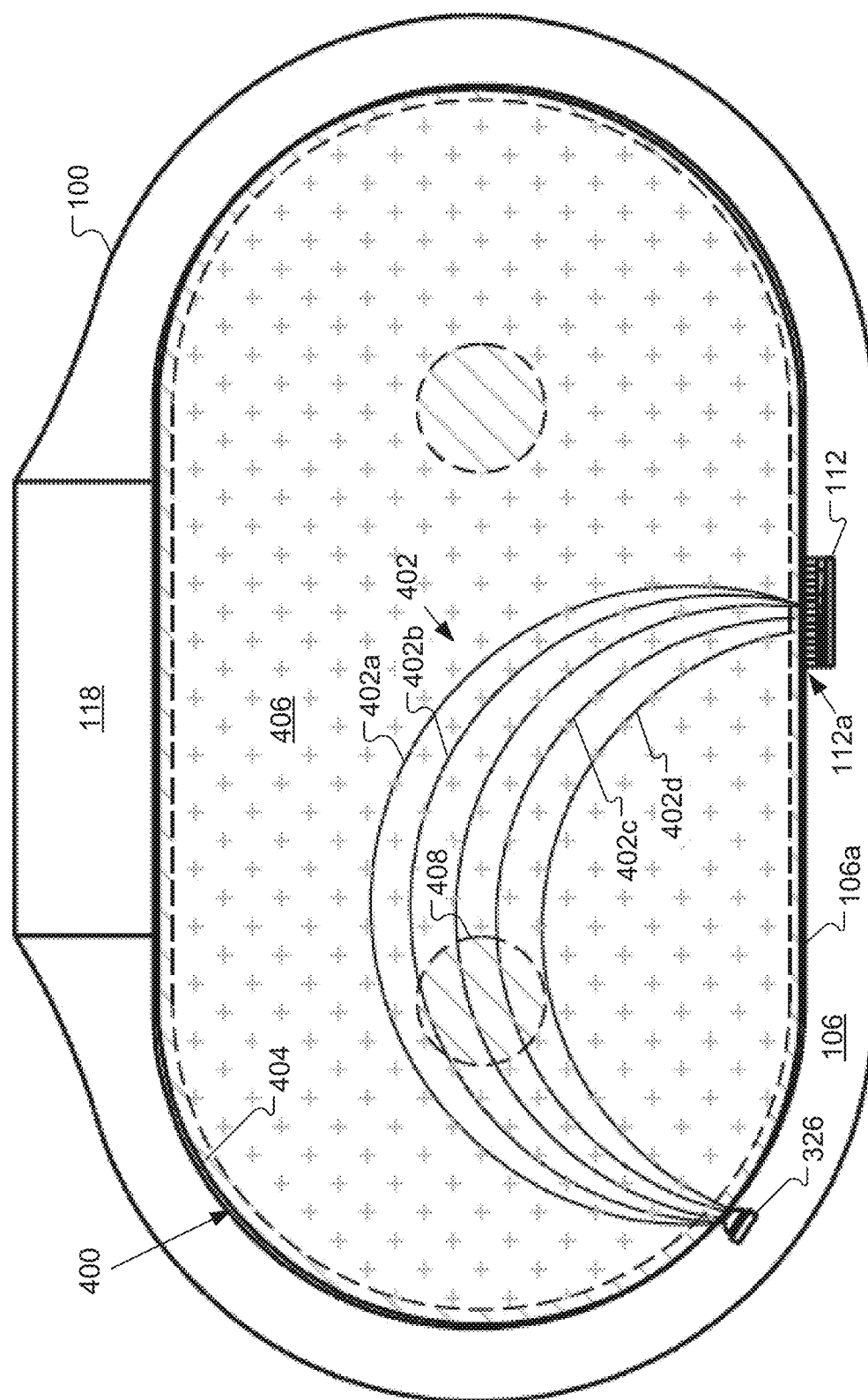
FIG. 4 illustrates a view of a wearable device around a body part with a light source emitting light through the body part to a sensor, according to an embodiment.

FIG. 4 illustrates a view of the wearable device 100 around a body part 400 of the user with the light source 326 emitting light 402 through the body part 400 to the first sensor 112, according to an embodiment. Some of the features in FIG. 4 are the same as or similar to some of the features in FIGS. 1-3H as noted by same reference numbers, unless expressly described otherwise. The body part 400 may include a dermal layer 404, a subdermal layer 406, and a muscular-walled tube 408. In an embodiment, the body part 400 may include a wrist of the user. The muscular-walled tube 408 may include a vein or an artery of the user. The wearable device 100 may include the band 106 which may wrap around the body part 400. The light source 112 may be positioned within the band 106 to face the body part 400 when the band 106 is wrapped around the body part 400. The first sensor 112 may include a miniaturized spectrometer. The first sensor 112 may be disposed within the band 106 to face the body part 400 as the band 106 is wrapped around the body part 400.

In an embodiment, the light source 326 may be at least partially exposed from the band 106. For example, an illuminating portion of the light source may be exposed from the band 106 such that the illuminating portion of the light source 326 protrudes from the band 106 or is set within the band 106, forming a discontinuity in an inside surface 106a of the band 106. In another example, the illuminating portion of the light source 326 may be flush with the inside surface 106a of the band 106 to form a continuous surface with the inside surface 106a. In an embodiment, the first sensor 112 may be at least partially exposed from the band 106. For example, a surface 112a of the first sensor 112 may be flush with the inside surface 106a of the band 106 such that the surface 112a of the first sensor 112 and the inside surface 106a of the band 106 form a continuous surface. In another example, the first sensor 112 may protrude from the band 106. The band may encompass a portion of the first sensor 112, and a portion of the first sensor 112 may extend from the band 106. In yet another example, the first sensor 112 may be set within the band 106, forming a cavity in the band 106 over the first sensor 112. The cavity in the band 106 may form a discontinuity in the inside surface 106a of the band 106.

In an embodiment, the light source 326 may emit the light 402 omnidirectionally or partially omnidirectionally. For example, the light source 326 may emit the light 402 omnidirectionally beyond the inside surface 106a of the band 106. In another embodiment, the light may be channeled and/or directed in a direction and/or within a range of directions corresponding to polar and/or azimuthal ranges. For example, the light 402 may be emitted in a 360 degree polar range and a 180 degree azimuthal range. The polar range may vary from 1 degree to 360 degrees. The azimuthal range may vary from 1 degree to 300 degrees. In an embodiment, the light 402 may be a ray of unidirectional light. The light 402 as initially emitted from the light source 326 may include a spectrum of wavelengths. The light 402 may be monochromatic or poly chromatic. The light 402 may be emitted from the light source 326 at a specific, selected, and/or known intensity level, where the intensity level may be known to a processing device disposed in the housing 118 and electrically coupled to the light source 326 and/or the first sensor 112. For example, the intensity level of the light 402 may be stored in transitory and/or non-transitory memory and/or into the processing device (such as in a cache of the processing device), or the intensity level of the light 402 may be measured and communicated to the processing device when the light 402 is emitted from the light source 326.

The light 402 may be reflected as it passes through the body part 400 so that it strikes the first sensor 112. As described earlier, the light source 326 may emit the light 402 omnidirectionally. The light 402 may include light rays 402a-d. The light rays 402a-d may follow different paths through the body part 400, and in an embodiment the light rays 402a-d may each be reflected towards the first sensor 112. As the light rays 402a-d are emitted from the light source 326, each light ray 402a-d may have a same and/or similar light profile as each other light ray 402a-d. The light profile may include the wavelength of the light 402, the intensity of the light 402, and/or the phase of the light 402. As the light rays 402a-d pass through the body part 400, the light profile for each light ray 402a-d may change differently from each other light ray 402a-d. Accordingly, each light ray 402a-d may have a different light profile from each other light ray 402a-d as it impinges on (i.e. strikes) the first sensor.

As the light 402 travels through the body part 400, the light 402 may reflect off a variety of tissues and/or other constituents within the body part 400. The light 402 may follow a non-linear path through the body part 400 from the light source 326 to the first sensor 112. In an embodiment, the path the light 402 follows may go through the dermal layer 404, the subdermal layer 406, and/or the muscular-walled tube 408. As the light 402 passes through the body part 400, constituents and/or tissues of the body part 400 may absorb and/or reflect various wavelengths of the light 402. For example, the muscular-walled tube 408 may include a vein or an artery. The vein or the artery may carry blood within the vein or artery. The blood may include various constituents, including red blood cells, white blood cells, water, platelets, glucose, mineral ions, hormones, proteins, and so forth. The various constituents of the blood may strongly absorb, transmit, and/or reflect light in different ways. For example, red blood cells may strongly absorb wavelengths ranging from 400 nanometers (nm) to 450 nm. Blood glucose may strongly reflect and/or transmit wavelengths ranging from 725 nm to 775 nm, from 1050 nm to 1100 nm, and/or from 1550 nm to 1700 nm.

Each wavelength may reflect a blend of constituents. Each constituent of blood may have a unique absorbance corresponding to a single wavelength. A resulting intensity of a wavelength passing through the vein or the artery may be the result of the combined effects of each of the constituent's absorbance coefficients and the respective concentrations of the constituents. The Beer-Lambert Law may be one way of concretely quantifying this effect. Quantifying the relative amount of the various blood constituents may be accomplished by determining relative intensities of several wavelengths and determining which combination of each of the constituents would give the net result. The quantification may be accomplished by a multivariate regression analysis and/or other machine learning algorithm based on an iterative optimization problem to reduce error from a training set.

The first sensor 112 may collimate the light rays 402a-d such that the light 402 striking the first sensor surface 112a at a roughly normal angle may pass into the first sensor 112. For example, light striking the first sensor surface 112a at an angle ranging from 60 degrees to 90 degrees, from 70 degrees to 90 degrees, from 75 degrees to 90 degrees, from 80 degrees to 90 degrees, and/or from 85 degrees to 90 degrees may pass into the first sensor 112. The first sensor 112 may filter the light rays 402a-d and may detect one or more features of the light profile of to each light ray 402a-d. The detected features may be communicated to the processing device. The processing device may perform one or more of various calculations and/or functions using and/or based on a comparison and/or analysis of the light profile of the light 402 as emitted from the light source 326 and light profiles of the light rays 402a-d detected by the first sensor 112.

In one embodiment, the wearable device 100 may include a flexible band such as the band 106, the user interface 104, the processing device 102, the light source 326, the miniaturized spectrometer such as the first sensor 112, and/or the electrical trace 108. The flexible band may be configured to extend at least partially around a wrist of a user, the wrist including the dermal layer 404 and the muscular-walled tube 408 within the wrist adjacent to a section of the dermal layer 404 along an underside of the wrist. The user interface 104 may be coupled to the flexible band. The processing device 102 may be coupled the flexible band. The light source 326 may be embedded in the flexible band. The light source 326 may be configured to press against the dermal layer 404 by the flexible band as the user wears the flexible band and emit light into the underside of the wrist as the user wears the flexible band. The miniaturized spectrometer may be integrated into the flexible band and positioned in the flexible band to: press against the dermal layer 404 along the underside of the wrist as the user wears the flexible band; and receive the light from the light source 326 through the underside of the wrist or the muscular-walled tube as the user wears the flexible band. The miniaturized spectrometer may include a collimator, an optical filter, and an optical sensor. The collimator may include a microtube, the microtube including a wall defining a through-channel, and the wall including a carbon nanotube forest. The carbon nanotube forest may include a bundle of carbon nanotubes aligned approximately parallel with each other. The optical filter may be configured to have a passband corresponding to a wavelength of light providing an indication of a condition or constituent of the wrist, the dermal layer 404, or the muscular-walled tube 408. The optical sensor or processing device 102 may be configured to: identify the wavelength of light; and measure an intensity of the wavelength of light. The collimator, the optical filter, or the optical sensor may be stacked together. The electrical trace 108 may be integrated into the flexible band and electrically interconnect the processing device 102, the user interface 104, the light source 326, or the optical sensor.

In an example of the embodiment, a borosilicate glass may be stacked with the collimator, the optical filter, or the optical sensor, where the borosilicate glass is aligned flush with the inside surface 106a of the flexible band, the inside surface 106a designed to face the wrist of the user as the user wears the flexible band.

In one example, identifying the wavelength may include correlating a position on the optical sensor where the light strikes the optical sensor with a segment of the optical filter aligned with the position on the optical sensor. The segment of the optical filter may include a passband for the wavelength.

In another example, the collimator may be positioned in the stack to press against the wrist as the user wears the flexible band, where the collimator is positioned, as the user wears the flexible band, to collimate the light to enable the light to strike a portion of the optical sensor corresponding to a portion of the filter through which the light passed. Or, the filter may be positioned in the stack to press against the wrist as the user wears the flexible band to enable filtered light to be collimated and passed to the portion of the optical sensor corresponding to the portion of the filter through which the light passed.

In an example, the processing device 102 may be configured to determine a constituent of the muscular-walled tube 408 based on the intensity of the wavelength.

In an example, the inward-facing surface 112a of the miniaturized spectrometer may be flush with the inside surface 106a of the flexible band. The inward-facing surface 112a of the miniaturized spectrometer may be positioned in the flexible band to be pressed against the wrist of the user as the user wears the flexible band to prevent outside light from outside the wrist from entering the miniaturized spectrometer or reaching the optical sensor as the user wears the flexible band. The inward-facing surface 112a may be configured to receive the light into the miniaturized spectrometer through the wrist as the user wears the flexible band. The inside surface 106a of the flexible band may face the wrist as the user wears the flexible band.

In another example, the light source 326 and the miniaturized spectrometer may be positioned in the flexible band relative to each other to prevent light noise from being detected by the miniaturized spectrometer, where the light noise includes external light entering the miniaturized spectrometer from outside the wrist. The light source 326 and the miniaturized spectrometer are spaced from each other in the flexible band to prevent light emitted by the light source traveling outside the wrist from being detected by the miniaturized spectrometer as the user wears the flexible band. The light source 326 may be recessed in the flexible band to prevent light emitted by the light source from traveling outside the wrist as the user wears the flexible band.

In another example, the user interface 104 may be coupled to the band 106 to be positioned on a top side of the wrist opposite the light source or the miniaturized spectrometer as the user wears the flexible band. The user interface may be coupled to the flexible band in a position to orient the user to align the light source 326 or the miniaturized spectrometer with the muscular-walled tube 408 as the user wears the flexible band.

In an embodiment, the wearable device 100 may include the band 106 and the miniaturized spectrometer. The band 106 may be configured to extend at least partially around the body part 400 of a user, the body part 400 including the dermal layer 404 and a subdermal feature within the body part 400. The light source 326 may be embedded in the band 106, where the light source 326 may be configured to emit light into the body part 400 as the user wears the band 106. The miniaturized spectrometer may be integrated into the band, and may include a collimator, an optical filter, and an optical sensor. The collimator may collimate the light, and may include a plurality of microtubes, where the microtubes include carbon nanotube walls defining a plurality of through-channels. The optical filter may filter the light and may be configured to have a plurality of passbands corresponding to constituent wavelengths of the light. The optical sensor may be configured to detect the intensities of the constituent wavelengths and communicate the intensities to the processing device. The miniaturized spectrometer may be configured to: collimate the light; filter the light into the relevant constituent wavelengths, where the relevant constituent wavelengths are reflected by or transmitted through the body part 400, the dermal layer 404, or the subdermal feature as the user wears the band; and detect the intensities of the constituent wavelengths.

In one example of the embodiment, the light source 326 may include a light-emitting portion flush with the inside surface 106a of the band 106. The inside surface 106a of the band 106 may face the body part 400 as the user wears the band. The receiving surface 112a of the miniaturized spectrometer may be flush with the inside surface 106a of the band 106. The receiving surface 112s may be configured to receive the light into the miniaturized spectrometer through the body part 400 as the user wears the band 106. The inside surface 106a of the band may face the body part 400 as the user wears the band 106.

In another example, the wearable device 100 may include the user interface 104, where the user interface 104 may be coupled to the band 106 to be adjacent to a side of the body part 400 opposite the light source 326 or the miniaturized spectrometer as the user wears the band 106. The wearable device 100 may include the processing device 102 configured to identify, as the user wears the band 106, a quantity of a constituent of the subdermal feature based on the intensities of the constituent wavelengths.

In one example, the light source 326 and the miniaturized spectrometer may be spaced from each other in the band 106 to prevent light emitted by the light source 326 and traveling outside the body part 400 from being detected by the miniaturized spectrometer as the user wears the band 106. The band 106 may be configured to press the light source 326 and the miniaturized spectrometer into the wrist, and/or the light source 326 and the miniaturized spectrometer may be recessed within the band 106.

In one embodiment, the wearable device 100 may include the band 106, the light source 326, the collimator, and/or the optical sensor, where the collimator, optical sensor, or the optical filter are arranged together to form a stack embedded in the band. The band 106 may be configured to extend at least partially around the body part 400 of the user, the body part 400 including an internal feature within the body part 400. The light source 326 may be embedded in the band, where the light source 326 may be configured to emit light into the body part 400 as the user wears the band 106. The collimator and the optical sensor may be stacked together. The optical sensor may be positioned in the stack to detect light passing through the body part 400 as the user wears the band. The collimator may be positioned in the stack to be between the optical sensor and the body part 400 as the user wears the band 106. The optical filter may be positioned in the band 106 adjacent to the light source 326. The optical filter may be positioned in the band 106 to be between the light source 326 and the body part 400 as the user wears the band 106.

In one example of the embodiment, the light source 326 may include a light-emitting portion flush with the inside surface 106a of the band 106. The inside surface 106a of the band may face the body part 400 as the user wears the band 400. The receiving surface 112a of the miniaturized spectrometer may be flush with the inside surface 106a of the band 106. The receiving surface 112a may be configured to receive the light into the miniaturized spectrometer through the body part 400 as the user wears the band 106. The inside surface 106a of the band 106 may face the body part 400 as the user wears the band 106.

Figure 5A:
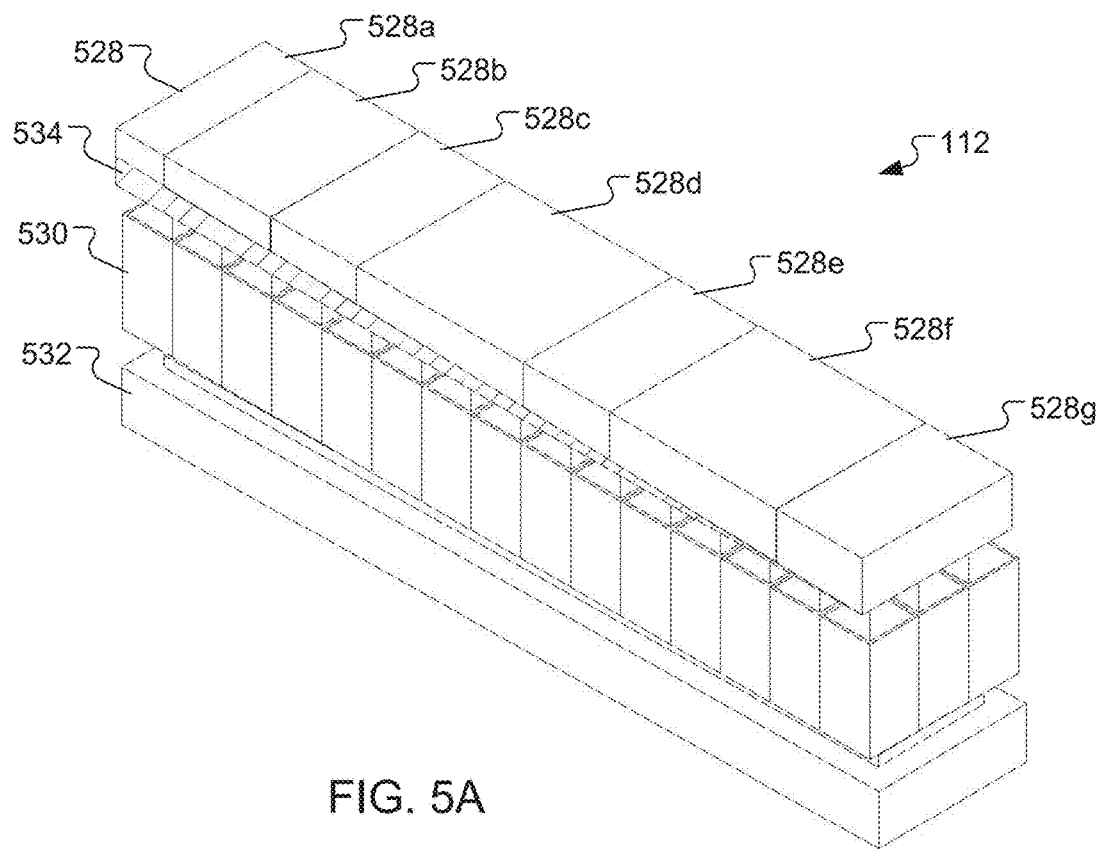
FIG. 5A illustrates a perspective view of a first sensor, according to an embodiment.

FIG. 5A illustrates a side perspective exploded view of the first sensor 112, according to an embodiment. Some of the features in FIG. 5A are the same as or similar to some of the features in FIGS. 1-4 as noted by same reference numbers, unless expressly described otherwise. In one embodiment, the first sensor 112 may include a miniaturized spectrometer. The first sensor 112 may include a filter 528, a collimator 530, and an optical sensor 532. In one embodiment, the filter 528 may be an optical filter, such as a variable filter, a linear variable filter, an absorptive filter, a dichroic filter, a monochromatic filter, an infrared filter, an ultraviolet filter, a neutral density filter, a longpass filter, a band-pass filter, a shortpass filter, a guided-mode resonance filter, a metal mesh filter, a polarizer filter, an arc welding filter, a wedge filter, and so forth. In another embodiment, the filter may be a Fabry-Perot Etalon filter. In yet another embodiment, the filter 528 may include colored glass.

In an embodiment, the filter 528 may allow light of a particular wavelength and/or range of wavelengths to pass through the filter 528 while attenuating other wavelengths of light. The filter 528 may accomplish this by attenuating a significantly higher portion of the intensity of other wavelengths. For example, the filter 528 may attenuate 90% of the intensity of wavelengths up to 550 nm, the filter 528 may attenuate 100% of the intensity of wavelengths equal to or greater than 750 nm, and the filter 528 may attenuate the intensity of wavelengths between 550 nm and 750 nm according to a curve with a peak at 700 nm.

In an embodiment, the filter 528 may allow a user to select which wavelengths of light may be detected by the optical sensor 532. The filter 528 may include a variable filter such as a linear variable filter which may have a spatially variable response to impinging light. The filter 528 may include a first region 528a corresponding to a first range of wavelength, a second region 528b corresponding to a second range of wavelengths, a third region 528c corresponding to a third range of wavelengths, a fourth region 528d corresponding to a fourth range of wavelengths, a fifth region 528e corresponding to a fifth range of wavelengths, a sixth region 528f corresponding to a sixth range of wavelengths, and a seventh region 528g corresponding to a seventh range of wavelengths. Each corresponding range of wavelengths may include a wavelength and/or range of wavelengths that, at a position within the corresponding region, are passed through at a maximum intensity greater than an intensity for which any other wavelength passes through the filter 528 at the same position.

A linear variable filter may allow for selecting which wavelengths strike the optical sensor 532 at a specific position on the optical sensor 532. This may allow a processing device to, in turn, distinguish the relative intensities of wavelengths reflected from a tissue to determine which wavelengths are most strongly reflected from the tissue relative to an initial intensity of those wavelengths as emitted from a light source. The processing device may determine, based on the reflected wavelengths, one or more parameters, constituents, and/or conditions of the tissue. For example, light having a first wavelength may strike a first region of the optical sensor 532 corresponding to the first region 528a of the filter 528. The first wavelength may correspond to a constituent of a user's blood. The optical sensor 532 may communicate the intensity of the first wavelength to the processing device. The processing device may process the first wavelength based on an initial intensity of the wavelength, an expected attenuation of the wavelength, and/or other attenuation factors to determine an amount of the constituent in the user's blood. Different constituents of the user's blood may correspond different wavelengths and/or different transmitted intensities of the same wavelengths. The filter 528 may pass those wavelengths corresponding to the blood constituents to different positions on the optical sensor 532. The optical sensor 532 may pass the intensities of the corresponding wavelengths to the processing device, and the processing device may determine an amount of each blood constituent based on the intensity of each corresponding wavelength.

In an embodiment, in the first region 528a, wavelengths ranging from 400 nm to 450 nm may pass through the filter 528 with an average of up to 50% of an impinging intensity for light impinging on the first region 528a of the filter 528. In the first region 528a, wavelengths less than 400 nm and greater than 450 nm may be attenuated to 0% of the impinging intensity. In the second region 528b, wavelengths ranging from 450 nm to 500 nm may pass through the filter 528 with an average of up to 50% of the impinging intensity, whereas wavelengths less than 450 nm and greater than 500 nm may be attenuated to 0% of the impinging intensity. The pattern may continue for each of the third region 528c, the fourth region 528d, the fifth region 528e, the sixth region 528f, and/or the seventh region 528g. In an embodiment, a position within each region along a length of the filter 528 may correspond to a unique wavelength having the maximum pass-through intensity. For example, within the first region 528a, light having a wavelength of 400 nm may pass through the filter 528 with 50% of the impinging intensity at a first position, whereas light having a wavelength of 405 nm may be attenuated to 0% of the impinging intensity at the first position. At a second position within the first region 528a, the 405 nm light may pass through the filter with 50% of the impinging intensity, whereas the 400 nm light may be attenuated to 0% of the impinging intensity at the second position.

In an embodiment, the linear variable filter may include a gradient along which wavelengths filtered by the filter 528 may vary. The gradient may contribute to an increased width of a transmission curve of the filter 528. The gradient may, for example, be 0.035 nm per micron. One or more of the microtubes of the collimator 530 may have a width of a through-channel of the at least one microtube that may be 100 microns. Accordingly, the filter 528 may allow a 35 nm range of wavelengths passing through the collimator to also pass through the filter 528. A full width half maximum (FWHM) passband of the filter 528 corresponding to the one or more microtubes may range from 1 percent to 2 percent of a wavelength of peak transmission. Depending on the wavelength of peak transmission, a passband of the filter 528 corresponding to the one or more microtubes may have an apparent FWHM passband that is 1.5 times to 3 times wider than an actual FWHM passband of the filter 528 at a location of the at least one microtube. Amplification of the apparent FWHM passband may be minimized by reducing a width of the microtube or by quantizing within the microtube in software.

In an embodiment, the linear variable filter may have a gradient that is large compared to the width of the microtube such that a single microtube may correspond to a relatively wide passband. Quantizing within the microtube may include, in one embodiment, treating light entering the microtube in software as having the same center wavelength and reporting the intensity of the center wavelength as a combined result of the intensities of all the wavelengths corresponding to the microtube. In another embodiment, quantizing within the microtube may include having an optical sensor 532 with a photodiode array. The elements, i.e. pixels, of the array may be sized relative to the microtube such that a plurality of the elements may fit within the microtube. The elements may be assigned different wavelengths corresponding to the elements' positions relative to the filter and/or the microtube.

In one embodiment, a physiological constituent of interest may be glucose. The glucose may be blood glucose. The blood glucose may have a unique spectral profile for wavelengths ranging from 700 nm to 2500 nm, which may be referred to as a general band for glucose. The spectral profile may be characterized by each wavelength within the general band for glucose having a transmission percentage. The spectral profile may be a combination of the transmission percentages for each wavelength within the general band for glucose. In an embodiment, narrower bands within the general band for glucose may be identified for which the blood glucose may have unique spectral profiles. The narrower bands may include a band ranging from 700 nm to 1176 nm, a band ranging from 1333 nm to 1818 nm, and/or a band ranging from 2000 nm to 2500 nm.

In another embodiment, the physiological constituent of interest may be blood oxygen saturation (O2sat). The O2sat may have a unique spectral profile for wavelengths ranging from 400 nm to 2500 nm, which may be referred to as a general band for O2sat. Narrower bands within the general band for O2sat may be identified for which the O2sat may have unique spectral profiles. The narrower bands may include a band ranging from 600 nm to 900 nm and from 1300 nm to 1800 nm. In embodiments tailored to measure O2sat, the filter 528 may include graphene, which may have a tunable passband ranging from 400 nm to 1800 nm.

In a specific embodiment, the filter 528 may include a linear variable filter having a passband ranging from 908 nm to 1676 nm. The slope of the gradient may be 125 nm/mm +/− 2.5 nm/mm. A half power bandwidth of the linear variable filter may be less than 1% of a center wavelength of the linear variable filter. Transmission of wavelengths within the passband may average to greater than or equal to 50 percent, whereas transmission of out-of-band wavelengths may average tor less than or equal to 0.01 percent for wavelengths ranging from 190 nm to 2500 nm. The linear variable filter may include a thin film of indium gallium arsenide deposited on an optical borosilicate-crown glass substrate. The linear variable filter may have a surface quality of 60 to 40, and edge chips may be less than or equal to 0.25 mm.

In an embodiment, the filter 528 may include an absorptive filter. An absorptive filter may be formed to have distinct cutoff edges between regions of the absorptive filter corresponding to different wavelength ranges. Furthermore, an absorptive filter may be manufactured of a durable and/or flexible material. In an embodiment, the filter 528 may include a three-dimensional structural interference filter. The structural interference filter may have a surface shape and/or an internal grain boundary shape which may reflect some wavelengths of light outside a passband of the filter 528 while transmitting others within the passband of the filter 528. In an embodiment, the filter 528 may include a dichroic filter, which may also be referred to as an interference filter. The dichroic filter may be variable. The dichroic filter may allow for very precise selection of wavelengths to be passed through the filter 528. For example, the dichroic filter may have a transmission profile with a narrow peak, such as a full width half max (FWHM) wavelength range of 50 nm, 40 nm, 30 nm, 25 nm, 20 nm, 10 nm, 5 nm, and/or 1 nm. The dichroic filter may be implemented in embodiments where the filter 528 is incorporated into a sensor for measuring sensitive phenomena. The sensitive phenomena may include various physiological parameters, conditions, and/or constituents for which small-percentage changes, such as less than or equal to a 50 percent change, results in dramatically different outcomes. For example, the sensitive phenomenon may include a blood acidity level. A healthy blood acidity may include a pH of 7.4. A blood pH less than or equal to 6.8 or greater than or equal to 7.8 may result in irreversible cell damage. In another example, the sensitive phenomenon may include bone density.

In an embodiment, the filter 528 may include a grism. In an embodiment, the filter 528 may include a prism coupled to a diffraction grating. As used herein, the grism or the coupled prism and diffraction grating may be referred to as the grism. In various embodiments, the prism may include a dispersion prism and/or a prismatic sheet, such as a Fresnel prism. In various embodiments, the diffraction grating may include a ruled grating, a holographic grating, a transmission grating, a reflective grating, a blazed holographic grating, a concave grating, an aberration corrected concave grating, a constant deviation monochromator concave grating, a Rowland type concave grating, a blazed holographic concave grating, a sinusoidal holographic grating, a sinusoidal ruled grating, a pulse compression grating, and so forth. In an embodiment, the diffraction grating may include a volume phase holographic (VPH) grating, which may have a high transmission percentage of impinging light relative to other types of diffraction gratings. In an embodiment, the diffraction grating may diffract impinging light along one dimension.

In an embodiment, the diffraction grating may have a varying line spacing. For example, the line spacing of the diffraction grating may increase and/or decrease along a length and/or width of the diffraction grating. In an embodiment, the lines of the diffraction grating may be aligned parallel to the width of the diffraction grating and/or perpendicular to the length of the diffraction grating. The line spacing may be uniform along the width of the diffraction grating and may vary along the length of the diffraction grating. In one embodiment, the line spacing may be uniform along the length of the diffraction grating and may vary along the width of the diffraction grating. In another embodiment, the line spacing may vary along the length of the diffraction grating and may vary along the width of the diffraction grating. In an embodiment, a blaze angle of the diffraction grating may vary along the diffraction grating. The blaze angle may be uniform along the width of the diffraction grating and may vary along the length of the diffraction grating. The blaze angle may be uniform along the length of the diffraction grating and may vary along the width of the diffraction grating. The blaze angle may vary along the length of the diffraction grating and may vary along the width of the diffraction grating. In an embodiment, varying the line spacing and/or the blaze angle may allow for spatial filtering of light by filtering different wavelengths of light at different sections the filter 528.

A spatially varied diffraction grating (i.e. varying line spacing and/or different blaze angle as described above) may allow for precise selection of wavelengths to be filtered by the filter 528. The spatially varied diffraction grating may be formed to filter a variety of ranges of wavelengths. The spatially varied diffraction grating may be formed with discontinuities between the ranges of wavelengths. In an embodiment, the filter 528 may include the spatially varied diffraction grating. The filter 528 may include a discontinuity between the first region 528 and the second region 528b. The first region 528a may filter out wavelengths outside a range of wavelengths from 400 nm to 450 nm. The second region 528b may filter out wavelengths outside a range of wavelengths ranging from 700 nm to 800 nm.

In an embodiment, the grism may be disposed between the collimator 530 and the optical sensor 532. Light passed through the collimator 530 may strike the grism within a range of angles of incidence where a median of the range may be a normal incidence. The diffraction grating may separate various constituent wavelengths of the light incident on the diffraction grating such that light leaving the diffraction grating at a normal angle may include all the wavelengths of the incident light, and the separated constituent wavelengths of the impinging light may leave the diffraction grating at non-normal angles. The prism may realign the separated constituent wavelengths so that the separated constituent wavelengths may pass from the prism normal to a surface of the optical sensor 532. In an embodiment, the collimator 530 may be disposed between the grism and the optical sensor 532. The collimator 530 may absorb and/or otherwise eliminate unseparated light passing from the grism. For example, the collimator 530 may include CNTs. The CNTs may have an average reflectance of less than or equal to 10 percent, less than or equal to 5 percent, less than or equal to 2 percent, less than or equal to 1 percent, less than or equal to 0.5 percent, and/or less than or equal to 0.2 percent. Accordingly, the CNTs may strongly absorb light striking the CNTs, making the collimator very "black."

In one embodiment, the collimator 530 may include a device that restricts beam(s) of particles or waves passing into the first sensor 112, such as light in visible and/or non-visible wavelengths, to specific directions of motion, angles, or ranges of angles to become more aligned in a specific direction as the beam(s) travels through the first sensor 112. The collimator 530 may restrict a spatial cross section of the beam(s). In an embodiment, the collimator 530 may restrict the beam(s) along one dimension and/or along two dimensions.

The filter 528 may have a length ranging from 5 mm to 9 mm, from 6 mm to 9 mm, or from 7 mm to 9 mm. In an embodiment, the filter 528 may have a length of 7 mm, 7.35 mm, 7.5 mm, or 7.7 mm. The filter 528 may have a width ranging from 0.5 mm to 2 mm, from 0.75 mm to 1.75 mm, or from 1 mm to 1.5 mm. In an embodiment, the filter 528 may have a width of 1.15 mm, 1.35 mm, or 1.5 mm. The filter 528 ay have a thickness ranging from 0.5 mm to 3 mm, from 0.75 mm to 2.5 mm, or from 1 mm to 2 mm. In an embodiment, the filter may have a thickness of 1.25 mm, 1.5 mm, or 1.75 mm.

The collimator 530 may be formed in one or more of a variety of ways. In various embodiments, the collimator 530 may be formed of one or more microtubes. In an embodiment, the collimator 530 may include a plurality of microtubes, wherein each microtube is defined by one or more walls encircling a through-channel. A microtube of the plurality of microtubes may have a width ranging from 10 microns to 150 microns, and/or a height ranging from 30 microns to 500 microns. For example, the microtube may have a height equal to less than a thickness of 4 pages of printer paper, and a width equal to less than a thickness of 1 page of printer paper. The microtubes may be prepared separately and joined together, such as by a binder, or the microtubes may be prepared together. For example, the walls of the microtubes may be formed of CNTs. A catalyst layer may be patterned on a substrate forming an impression of the plurality of microtubes, and the CNTs may be grown on the catalyst layer, forming the walls encircling the through-channels to form the microtubes. In another embodiment, the collimator 530 may include a volume of material through which through-channels and/or apertures are formed. The volume of material may, for example, include a photoresist material. The through-channels and/or apertures may be etched through the photoresist material, such as by photolithography or plasma etching.

The collimator 530 may be positioned against the filter 528 and/or the optical sensor. For example, the collimator 530 may be disposed between the filter 528 and the optical sensor 532 as illustrated in FIG. 5A, or the filter may be disposed between the collimator 530 and the optical sensor 532 as illustrated in FIG. 5C. In an embodiment, one or more of the walls forming one or more of the microtubes of the collimator 530 may be aligned normal to a surface of the filter 528 and/or a surface of the optical sensor 532. In an embodiment such as is shown in FIG. 5A, light may pass through the filter 528 and the collimator 530 may allow light within a range of normal incidence passing from the filter 528 to impinge on the optical sensor 532. In an embodiment such as is shown in FIG. 5C, the collimator 530 may allow light to impinge on the filter 528 within a range of normal incidence. In an alternative embodiment, the collimator wall may be aligned at a non-normal angle relative to the surface of the filter 528 and/or the surface of the optical sensor 532. The angle may correspond to an angle of separated light leaving the filter 528. For example, the filter 528 may include a diffraction grating. Light may impinge on the diffraction grating at a normal angle. Separated light may leave the diffraction grating at a non-normal angle. The angle at which the wall of the collimator 530 is aligned to the filter 528 and/or the optical sensor may match the angle corresponding to a first order of separated light leaving the diffraction grating, i.e. a diffraction maxima function equal to one, where the function is equal to an inter-grating spacing times the sine of a blaze angle divided by a wavelength of the light impinging on the diffraction grating.

The collimator 530 may have a length ranging from 5 mm to 9 mm, from 6 mm to 9 mm, or from 7 mm to 9 mm. In an embodiment, the collimator 530 may have a length of 7 mm, 7.35 mm, 7.5 mm, or 7.7 mm. The collimator 530 may have a width ranging from 0.5 mm to 2 mm, from 0.75 mm to 1.75 mm, or from 1 mm to 1.5 mm. In an embodiment, the collimator 530 may have a width of 1.15 mm, 1.35 mm, or 1.5 mm. The collimator may have a thickness ranging from 10 microns to 300 microns, from 20 microns to 250 microns, or from 25 microns to 200 microns. In various embodiments, the substrate on which the collimator is grown may be incorporated with the collimator into the first sensor 112. For example, the collimator may be grown on a borosilicate glass. The collimator substrate may have the same length and width dimensions as the collimator. The collimator substrate length and width dimensions may exceed the collimator dimensions by up to 2 mm, up to 1.5 mm, up to 1 mm, up to 0.5 mm, up to 0.25 mm, up to 0.1 mm, or up to 0.05 mm. The collimator substrate may have a thickness ranging from 0.1 mm to 1.5 mm, from 0.25 mm to 1.25 mm, or from 0.5 mm to 1 mm.

The optical sensor 532 may be operable to convert light rays into electronic signals. For example, the optical sensor 532 may measure a physical quantity of light at a defined wavelength or wavelength range and translate the measurement into a form that is readable by a processing device. The optical sensor 532 may include a semiconductor. The semiconductor may have one or more bandgaps corresponding to the defined wavelength and/or wavelength range. The semiconductor may be arranged into an array, such as an array of pixels, corresponding to regions of the filter 528 such as the first region 528a, the second region 528b, and so forth. In various embodiments, the semiconductor may include an alloy of indium, gallium, phosphorus, and/or arsenic. In one embodiment, the semiconductor may include an alloy of indium arsenide, gallium arsenide, indium phosphide, and/or gallium phosphide. In one embodiment, the semiconductor may include lead(II) sulfide. In yet another embodiment the semiconductor may include one or more sheets of graphene. The semiconductor may be incorporated into a diode such as a photodiode. In another example, the optical sensor 532 may be a temperature sensor, a velocity liquid level sensor, a pressure sensor, a displacement (position) sensor, a vibration sensor, a chemical sensor, a force radiation sensor, a pH-value sensor, a strain sensor, an acoustic field sensor, an electric field sensor, a photoconductive sensor, a photodiode sensor, a through-beam sensor, a retro-reflective sensor, a diffuse reflection sensor, and so forth.

The optical sensor 532 may include a segment such as a pixel. In an embodiment, the optical sensor 532 may include a plurality of the segment, such as a plurality of pixels. The sensor segment may be aligned with a region of the filter 528 such as the first region 528a, the second region 528b, and so forth. The segment may have an identifier such that the processing device may associate the segment with the region of the filter. The identifier may enable the processing device to determine a wavelength of light detected by the segment of the optical sensor 532. For example, in one embodiment, the optical sensor may include a first sensor segment aligned with the first filter region 528a, a second sensor segment aligned with the second filter region 528b, and so forth. The first sensor segment may be identified by the processing device as detecting a wavelength and/or range of wavelengths that may pass unfiltered through the first filter region 528a. For example, wavelengths ranging from 400 nm to 449 nm may pass unfiltered through the first filter region 528a. The unfiltered light may strike the first sensor segment, and the first sensor segment may, in response generate an electrical signal that may be transmitted to the processing device. The processing device may identify the electrical signal as being transmitted by the first sensor segment and may identify that signals transmitted by the first sensor segment may be generated by light having a wavelength ranging from 400 nm to 449 nm.

The optical sensor 532 may have a length ranging from 10 mm to 20 mm, from 12 mm to 18 mm, or from 14 mm to 16 mm. In an embodiment the optical sensor 532 may have a length of 13.5 mm. The optical sensor 532 may have a width ranging from 1 mm o 10 mm, from 2 mm to 8 mm, or from 4 mm to 6 mm. In an embodiment, the optical sensor 532 may have a width of 5.2 mm. The optical sensor 532 may have a thickness ranging from 0.5 mm to 5 mm, from 1 mm to 3 mm, or from 1.5 mm to 2.5 mm. In an embodiment, the optical sensor 532 may have a thickness of 2 mm. The optical sensor 532 may include a photosensitive area and a non-photosensitive area. The photosensitive area may be smaller than the non-photosensitive area. The photosensitive area may have a length ranging from 5 mm to 9 mm, from 6 mm to 9 mm, or from 7 mm to 9 mm. In an embodiment, the photosensitive area may have a length of 7 mm, 7.35 mm, 7.5 mm, or 7.7 mm. The photosensitive area may have a width ranging from 0.5 mm to 2 mm, from 0.75 mm to 1.75 mm, or from 1 mm to 1.5 mm. In an embodiment, the photosensitive area may have a width of 1.15 mm, 1.35 mm, or 1.5 mm.

In an embodiment, regions of the filter 528, such as the linear variable filter, may be correlated to regions of the optical sensor 532, such as pixels on the optical sensor, by exposing the optical sensor 532 to a monochromatic and/or narrowband light source via the filter 528. The monochromatic light may strike the optical sensor 532 at a position corresponding to a location on the filter 528 through which the light is transmitted. A gradient and/or slope of the filter 528 may be used to extrapolate from the position on the optical sensor 532 the monochromatic light strikes which wavelengths will strike which pixels. For example, the monochromatic light may have a wavelength of 700 nm. The monochromatic light may pass through the filter 528 and strike a first row of pixels. The filter 528 may have a gradient of 125 nm/mm. A second row of pixels one mm from the first row will be assigned a wavelength band centered on 825 nm. A third row of pixels one mm from the second row will be assigned a wavelength band centered on 950 nm, and so forth. In one embodiment, the gradient and/or slope may be determined by exposing the filter 528 and the optical sensor 532 to different monochromatic light sources and identifying where on the optical sensor 532 the monochromatic light sources strike, then calculating the gradient based on the spacing between the positions and the difference in wavelength of the monochromatic light sources.

A calibration file for the optical sensor 532 may be set based on which pixel and/or set of pixels has the highest intensity. The calibration file for the optical sensor 532 may be set based on a curve fit to the intensities detected at a plurality of pixels. The curve may be compared to a calculated shape of the curve and the difference may be included in the calibration file to account for noise encountered during calibration.

In various embodiments, correlation of the filter 528 to the optical sensor 532 may be done during manufacturing and/or testing of the first sensor 112. Correlation may be done after the first sensor 112 is incorporated into the wearable device 100. The wearable device 100 may be placed around a calibration material. The calibration material may be transparent and may reflect and/or transflect light towards the first sensor 112. The light source 326 may be optically isolated from the first sensor 112 so that a substantial portion of light detected by the first sensor 112 is light reflected and/or transflected through the calibration material. The isolation may reduce and/or eliminate noise from light passing directly from the light source 326 to the first sensor 112. The calibration material may be selected to minimally absorb light. In an embodiment, the calibration material transmits approximately all light relevant to the correlation.

In various embodiments, correlation may be done during a user setup stage after an end user of the wearable device 100 obtains the wearable device 100. The wearable device 100 may include a calibration light source. The calibration light source may be positioned directly across the wearable device 100 from the first sensor 112 as the wearable device 100 is shaped in a shape corresponding to a shape of the wearable device 100 as the wearable device 100 is being worn by the user. The wearable device 100 may be shaped into the as-worn shape off of the user such that an unimpeded, direct path is formed between the calibration light source and the first light sensor 112. The calibration light may emit light directly towards the first sensor 112 and the filter 528 and the optical sensor 532 may be correlated as described herein.

In one embodiment, the wearable device 100 may include a fiberoptic path within and/or on the wearable device 100 between the light source 326 and the first sensor 112. Correlation of the filter 528 to the optical sensor 532 may include optically isolating the light source 326 from the first sensor 112 such that substantially all light emitted from the light source 326 is blocked from the first sensor 112 except light transmitted via the fiberoptic path. The light transmitted via the optical path may strike the optical sensor 532 via the filter 528. The optical sensor 532 and the filter 528 may be correlated as described herein while the wearable device 100 is being worn by the user.

In one embodiment, the filter 528 may be integrated with the optical sensor 532. For example, the optical sensor 532 may detect a discrete wavelength and/or a narrow band of wavelengths. The optical sensor 532 may include a photodiode having a large surface area, such as up to a same surface area as the first sensor 112. The discrete optical sensor 532 may have an enhances signal to noise ratio to more accurately quantify a physiological constituent when compared with a smaller and/or broader band embodiment of the optical sensor 532. In an embodiment, the narrow band, large surface area optical sensor 532 may be used to calibrate the first sensor 112.

In one embodiment, the filter 528, the collimator 530, and the optical sensor 532 may be stacked together to form the first sensor 112. In one example, the filter 528, the collimator 530, and the optical sensor 532 may be integrated together in a single sensor. In another example, the filter 528, the collimator 530, and the optical sensor 532 may be interconnected together. In one example, the filter 528, the collimator 530, and the optical sensor 532 may be stacked vertically on top of each other. In another embodiment, the filter 528 may be wedge shaped where one end of the filter 528 has a relatively thick end that tapers to a thinner edge. In one embodiment, the collimator 530 and the optical sensor 532 may have relatively flat top surfaces and/or bottom surfaces. When the filter is a wedge shape, a filling material 534 may be attached or affixed to the collimator 530 and/or the optical sensor 532 so that the filter 528 may rest or attach flush or level to the collimator 530 and/or the optical sensor 532. In one example, the filling material 534 may be an optically transparent material (such as clear glass or a clear plastic), an optically translucent material (such as polyurethane, colored or frosted glass, colored or frosted plastic, and so forth), or other material that does not interfere with defined wavelengths of light. In another example, the filling materials 534 may be attached or affixed to the collimator 530 and/or the optical sensor 532 by an adhesive, by welding, by friction, by a pressure fit, and so forth.

In a specific embodiment of the first sensor 112, the filter 528 and the collimator 530 may be stacked on the photoreactive area of the optical sensor 532. The optical sensor 532 may have a length of 13.5 mm, a width of 5.2 mm, and a thickness of 2 mm. The photoreactive area of the optical sensor 532 may have a length of 8 mm and a width of 1 mm. The filter 528 and the collimator 530 may have a length of 8 mm and a width of 1 mm. The filter 528 may have a thickness of 1.5 mm. The collimator 530 may have a thickness of 0.1 mm. Accordingly, the first sensor 112 may have a length of 13.5 mm, a width of 5.2 mm, and a thickness of 3.1 mm. In another specific embodiment, the collimator 530 may include the collimator substrate, and the collimator substrate may have a thickness of 0.5 mm. Accordingly, the collimator may have a thickness of 0.6 mm, and the first sensor 112 may have an overall thickness of 3.6 mm.

In one embodiment, a light source positioned at surface of a body part of an individual that is adjacent to a region of the body part where a muscular-walled tube is closest to an outer surface of the body part. The light source may transmit light within a wavelength range through the body part at a defined intensity and a defined depth to a second location along the surface of the body part. In another embodiment, the collimator 530 may be positioned at the second location along the surface of the body part. The collimator may receive a portion of the light. The collimator 530 may include a first microtube comprising a carbon nanotube tubular structure having a thickness between 1 micron and 10 microns and a height between 50 microns and 1000 microns. The first microtube may absorb a first sub-portion of the portion of the light that enters a tubular portion of the first microtube at a first range of angles and provide a channel for a second sub-portion of the portion of the light that enters the tubular portion of the first microtube at a second range of angles to pass through the first microtube. The collimator 530 may include the filter 528 attached to the collimator 530 or the optical sensor 532. The filter 528 may be aligned with the first microtube of the collimator 530 to filter out a defined wavelength or a defined wavelength range of the second sub-portion of the portion of the light. The collimator 530 may include a filling material 534 attached to the collimator or the filter 528 such that the filter 528 attaches level to the collimator 530 or the optical sensor 532. The filling material 534 may be an optically transparent material. The optical sensor 532 may attach to the collimator 530 or the filter 528. The optical sensor 532 may measure an intensity of the second sub-portion of the light that passes through the first microtube and the filter 528.

In one example, the collimator 530 may include an array of microtubes that includes the first microtube. In another example, the filter 528 may be aligned with the array of microtubes to filter out different wavelengths of second sub-portion of the portion of the light at different locations of the filter 528. The optical sensor 532 may measure an intensity of the different wavelengths of second sub-portion of the portion of the light. In another example, the collimator 530 may include a second microtube. A first portion of the filter 528 is aligned with the first microtube to filter out a first wavelength of second sub-portion of the portion of the light. A second portion of filter 528 is aligned with the second microtube to filter out a second wavelength of second sub-portion of the portion of the light. In another example, the optical sensor may measure the intensity of the first wavelength of second sub-portion of the portion of the light that passes through the first microtube and/or measure the intensity of the second wavelength of second sub-portion of the portion of the light that passes through the second microtube.

The carbon nanotube tubular structure may include: a first wall that includes a first set of carbon nanotubes infiltrated with carbon, a second wall comprising a second set of carbon nanotubes infiltrated with carbon, a third wall comprising a third set of carbon nanotubes infiltrated with carbon, and a fourth wall comprising a fourth set of carbon nanotubes infiltrated with carbon, wherein the first wall, the second wall, the third wall, and the fourth wall form a square tubular structure. The collimator 530 has a length between 5 mm and 9 mm and a width between 0.5 mm and 2 mm. In another example, the carbon nanotube tubular structure may include a cylindrical wall comprising carbon nanotubes infiltrated with carbon. In another example, the carbon nanotube tubular structure may include a carbon-infiltrated carbon nanotube forest. The carbon-infiltrated carbon nanotube forest may include a bundle of aligned carbon nanotubes. In another example, the filter 528 may be a continuous gradient with spectral properties that vary continuously along one dimension or plane of the filter 528 to filter out light rays of different wavelengths based on where the light rays strike along the surface of the filter 528.

In another example, the light transmitted from the light source passes directly from the light source to the collimator 530 or passes indirectly through a substance in the body part and be reflected towards the collimator 530. In another example, the carbon nanotube tubular structure may include carbon nanotube material to absorb the portion of the light with an average reflectance of less than or equal to 10 percent. In another example, the optical sensor 532 has a length ranging from 10 mm to 20 mm, a width ranging from 1 mm to 10 mm, a thickness ranging from 0.5 mm to 5 mm. In another example, the optical sensor 532 may include a photosensitive area and a non-photosensitive area. The photosensitive area may have a length ranging from 5 mm to 9 mm and a width ranging from 0.5 mm to 2 mm.

In another embodiment, the light source may be positioned at a first location along a surface of a body part of an individual that is adjacent to a region of the body part where a muscular-walled tube is closest to an outer surface of the body part. The light source may transmit light to a second location along the surface of the body part. The collimator 530 may be positioned at the second location along the surface of the body part. The collimator 530 may receive a portion of the light. The collimator 530 may include a first microtube comprising a first carbon nanotube tubular structure. The first microtube may absorb a first sub-portion of the portion of the light that enters a tubular portion of the first microtube at a first angle and/or provide a channel for a second sub-portion of the portion of the light that enters the tubular portion of the first microtube at a second angle to pass through the first microtube. The filter 528 may be aligned with the first microtube of the collimator 530 to filter out light at a defined wavelength or wavelength range of the second sub-portion of the portion of the light. The optical sensor 532 may be aligned with the collimator 530 or the filter 528. The optical sensor 532 may measure an intensity of the second sub-portion of the light that passes through the first microtube and the filter 528. In one example, the first carbon nanotube tubular structure may have a length between 5 mm and 9 mm and a width between 0.5 mm and 2 mm. In another example, filling material 534 attaches to the collimator 530 or the filter 528 such that the filter 528 attaches level to the collimator 530 or the optical sensor 532.

The collimator 530 may include a second microtube comprising a second carbon nanotube tubular structure. The second microtube may absorb a third sub-portion of the portion of the light that enters a tubular portion of the second microtube at a third angle and/or provide a second channel for a fourth sub-portion of the portion of the light that enters the tubular portion of the second microtube at a fourth angle to pass through the second microtube.

In another embodiment, the light source positioned at a first location along a surface of a body part of an individual. The light source may transmit light to a second location along the surface of the body part. The collimator 530 positioned at the second location along the surface of the body part. The collimator 530 may include a microtube a tubular structure. The microtube may absorb a first sub-portion of the portion of the light that enters a tubular portion of the microtube at a first angle and/or provide a channel for a second sub-portion of the portion of the light that enters the tubular portion of the microtube at a second angle to pass through the microtube. The filter 528 may be aligned with the microtube of the collimator 530 to filter out light at a defined wavelength or wavelength range of the second sub-portion of the portion of the light. The optical sensor 532 may be aligned with the collimator 530. The optical sensor 532 may measure an intensity of the second sub-portion of the light that passes through the microtube and the filter 528. The first location may be adjacent to a region of the body part where a muscular-walled tube is closest to an outer surface of the body part. In one example, the microtube may be a carbon nanotube structure. In another example, the light source may include a first illuminator and a second illuminator. The filter 528 may include a first sub-filter that is attached to the first illuminator and a second sub-filter that is attached to the second illuminator.

Figure 5B:
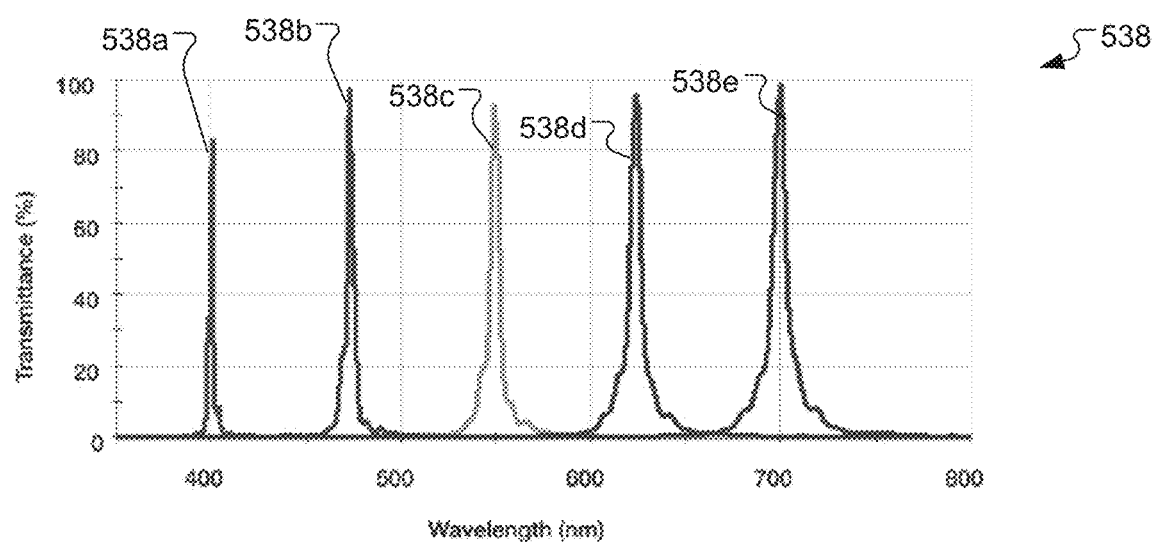
FIG. 5B illustrates a transmission profile of a filter which may be incorporated into the first sensor, according to an embodiment.
Figure 5C:
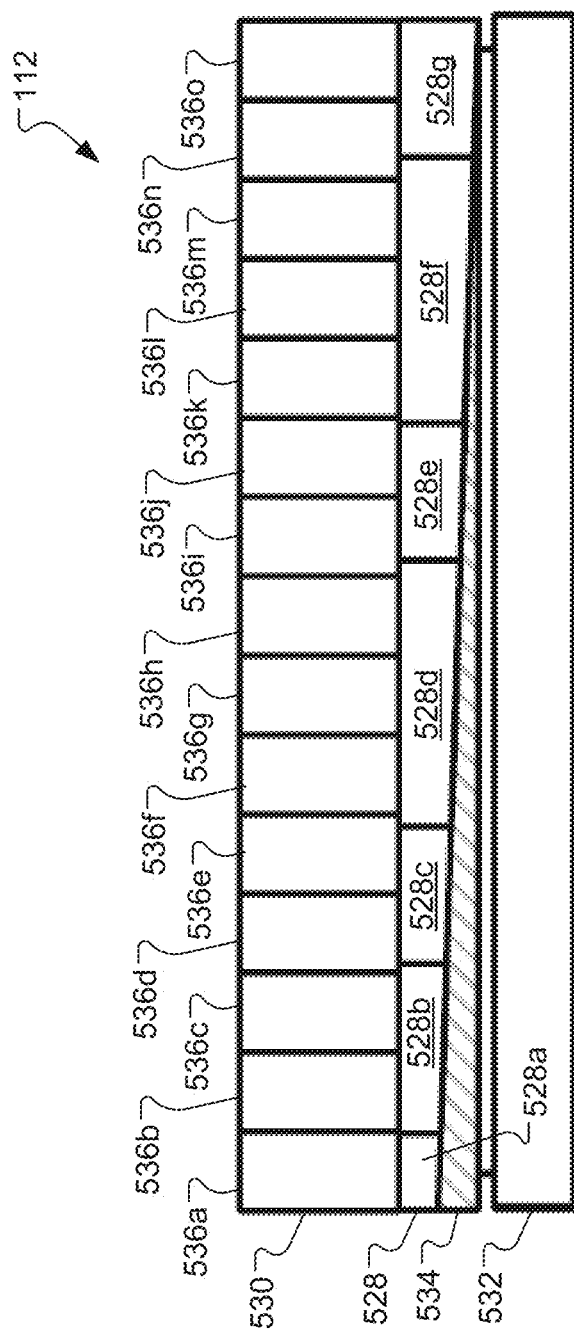
FIG. 5C illustrates a side view of the first sensor, according to an embodiment.

FIG. 5B is a graph 538 of transmission profiles 538*a-e* of the filter 528, according to an embodiment. Some of the features in FIG. 5B are the same as or similar to some of the features in FIGS. 1-5A as noted by same reference numbers, unless expressly described otherwise. The transmission profiles 538*a-e* may correspond to the filter regions 528*a-e*. For example: the transmission profile 538*a* may represent a range of wavelengths and corresponding intensities of the wavelengths which may pass through the first filter region 528*a;* the transmission profile 538*b* may represent a range of wavelengths and corresponding intensities of the wavelengths which may pass through the second filter region 528*b;* and so forth. In various embodiments, a passband corresponding to a particular region may be sharp and/or narrow. For example, the first filter region 528*a* may have a passband that may peak between 400 nm and 405 nm, and a may have a FWHM band that may range from 395 nm to 410 nm. The filter 528 having at least one region with a sharp and/or narrow passband. The sharp and/or narrow passband may correspond to a feature, such as a physiological condition, physiological parameter, and/or physiological constituent, that may be indicated by reflection of a narrow range of wavelengths, such as a range of 20 nm, 15 nm, 10 nm, 5 nm, 1 nm, and so forth.

FIG. 5C illustrates a side view of the first sensor 112, according to an embodiment. Some of the features in FIG. 5C are the same as or similar to some of the features in FIGS. 1-5B as noted by same reference numbers, unless expressly described otherwise. The order that the filter 528, the collimator 530, and the optical sensor 532 is not intended to be limiting. In one example, as shown in FIG. 5A, the filter 528 may be stacked on top, the collimator 530 may be stacked in the middle, and the optical sensor 532 may be stacked on the bottom. In another example, as shown in FIG. 5C, the collimator 530 may be stacked on top, the filter 528 may be stacked in the middle, and the optical sensor 532 may be stacked on the bottom.

As discussed above, the collimator 530 may be a device that restricts beam(s) of particles or waves passing into the sensor to specific directions of motion, angles, or ranges of angles to become more aligned in a specific direction. To restrict the beam(s), the collimator 530 may include one or more microtubes 536a-o that may extend from a top surface of the collimator 530 to a bottom surface of the collimator 530. The microtubes 536a-o may have various shapes, sizes, materials, or configurations to restrict the beam(s).

In various embodiments, one or more of the microtubes 536a-o may be aligned over one or more of the filter regions 528a-g. The microtube 536a may be aligned over the filter region 528a. The microtubes 536b-c may be aligned over the filter region 528b. The microtube 536d may be aligned over the filter regions 528b-c. The region 536e may be aligned over the filter regions 528c-d. The microtubes 536f-h may be aligned over the filter region 528d. The microtube 536i may be aligned over the filter regions 528d-e. The microtube 536j may be aligned over the filter region 528e. The microtubes 536k-m may be aligned over the filter region 528f. The microtube 536n may be aligned over the filter regions 528f-g. The microtube 536o may be aligned over the filter region 528g. Accordingly, light passing through one of the microtubes 536 may pass through more than one region of the filter 528.

Figure 5D:
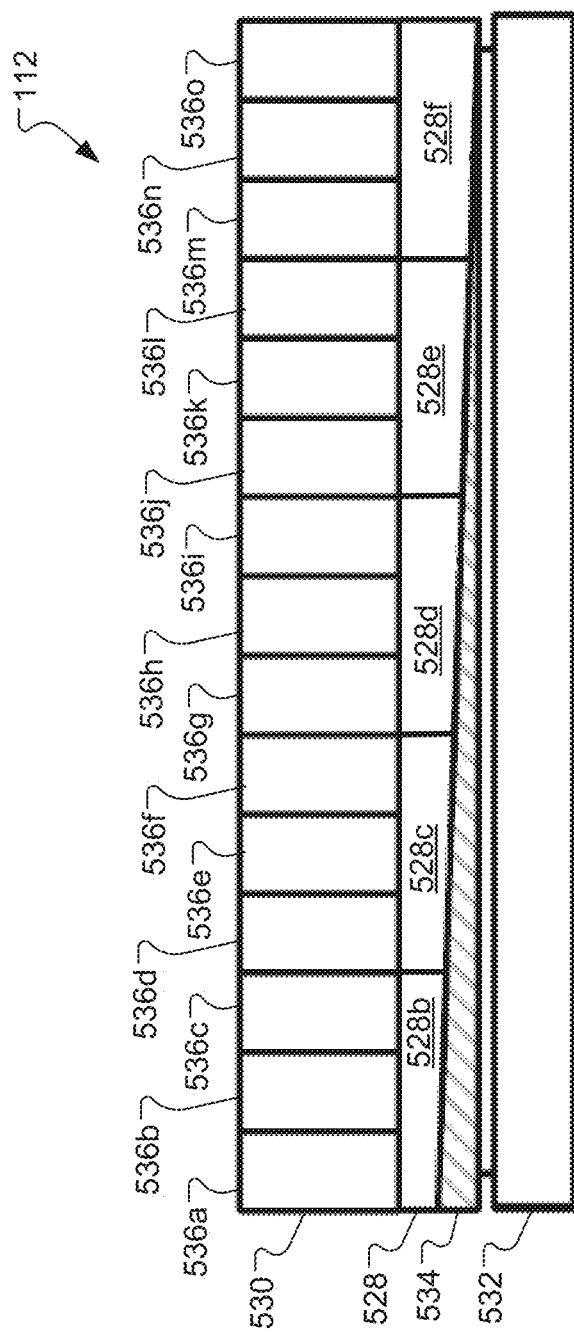
FIG. 5D illustrates an embodiment of the first sensor with the microtubes aligned directly with filter regions, according to an embodiment.

FIG. 5D illustrates an embodiment of the first sensor 112 with the microtubes 536a-o aligned directly with filter regions 528b-f, according to an embodiment. Some of the features in FIG. 5D are the same as or similar to some of the features in FIGS. 1-5C as noted by same reference numbers, unless expressly described otherwise. The microtubes 536a-c may be aligned over the filter region 528b. The microtubes 536d-f may be aligned over the filter region 528c. A wall between the microtube 526c and the microtube 536d may be aligned with a boundary between the filter region 528b and the filter region 528c. The microtubes 536g-i may be aligned over the filter region 528d. A wall between the microtube 526f and the microtube 536g may be aligned with a boundary between the filter region 528c and the filter region 528d. The microtubes 536j-l may be aligned over the filter region 528e. A wall between the microtube 526i and the microtube 536j may be aligned with a boundary between the filter region 528d and the filter region 528e. The microtubes 536m-o may be aligned over the filter region 528f. A wall between the microtube 526l and the microtube 536m may be aligned with a boundary between the filter region 528e and the filter region 528f.

The optical sensor 532 may include a plurality of pixels. One or more of the pixels may be assigned, in software, a particular wavelength corresponding to a section of the filter 528 over the corresponding pixel and through which light may pass before striking the corresponding pixel. In an embodiment, a shape and/or alignment of the pixels may not match a shape of the contour line of filter 528. For example, the contour line may be curved or non-perpendicular relative to the shape of the filter 528, and the pixels may be arranged rectangularly. The shape of the gradient of the filter 528 may be determined by comparing shifts in peak transmission intensities for neighboring rows of pixels running perpendicular to the contour lines of the filter 528. The shifts may be noted in software and the pixels may be reassigned to correspond to wavelengths according to the noted shift.

In various embodiments, walls separating and/or defining the microtubes 536a-o may be aligned with boundaries between the pixels. In various other embodiments, at least some of the walls separating and/or defining the microtubes 536a-o may be aligned over at least some of the pixels. This may produce an aliasing effect, which may significantly reduce an intensity of light detected by the optical sensor 532. The aliasing effect may be reduced by placing the collimator 530 at a sufficient distance from the optical sensor 532. Light from neighboring microtubes may bleed to areas beneath each other, reducing a shadow formed on the pixels by the walls between the microtubes 536a-o. For example, light passing through microtube 536a at an angle may strike a pixel beneath microtube 536b. The separation distance between the collimator 530 and the optical sensor 532 may be formed by the filter 528.

Figure 6A:
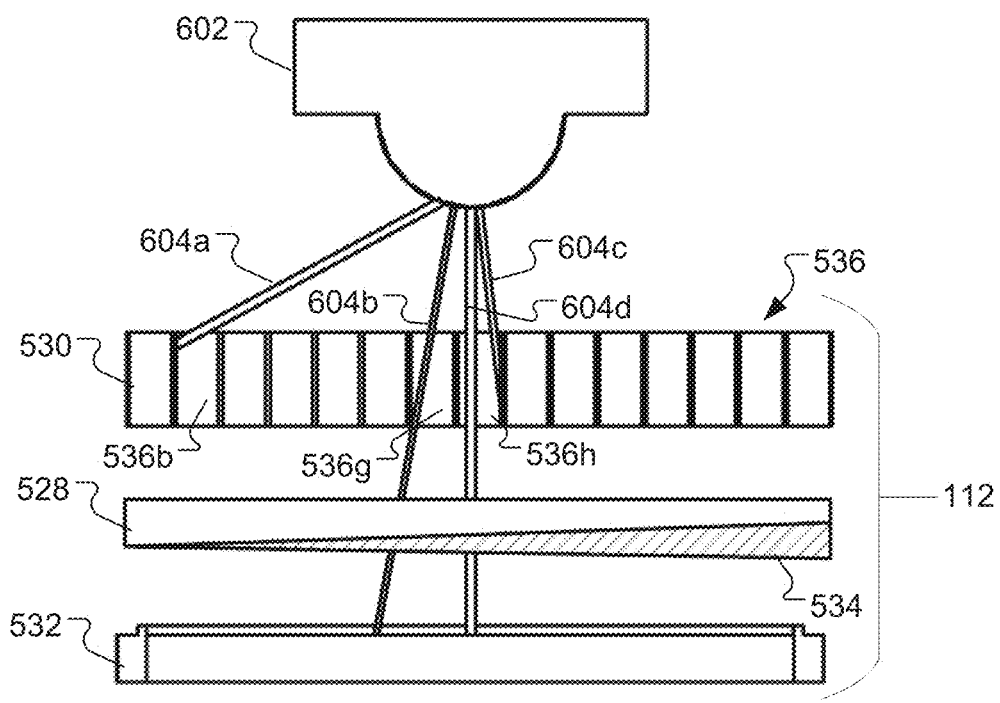
FIG. 6A illustrates a cross-sectional view of a light source emitting light rays into a first sensor, according to an embodiment.

FIG. 6A illustrates a cross-sectional view of a light source 602 emitting light rays 604a-d into the first sensor 112, according to an embodiment. Some of the features in FIG. 6A are the same as or similar to some of the features in FIGS. 1-5D as noted by same reference numbers, unless expressly described otherwise. In one embodiment, the light source 602 may emit light, such as light rays 604a-d. In one example, the light source 602 may emit the light rays 604a-d toward the first sensor 112. In one embodiment, the light source 602 may emit the light rays 604a-d directly at the first sensor 112. In another embodiment, the light source 602 may emit the light rays 604a-d at an object and one or more of light rays 604a-d may reflect off the object towards the first sensor 112.

The light source 602 may emit the light rays 604a-d at different angles such that the light rays 604a, 604b, 604c, and/or 604d may directly or indirectly encounter and/or pass into the first sensor 112 at different angles. In one example, light ray 604a may encounter microtube 536b of the collimator 530 at a first angle, where the light ray 604a encounters a sidewall of the microtube 536b such that the light ray 604a is absorbed by the sidewall. In another example, light ray 604b may encounter microtube 536g of the collimator 530 at a second angle, where the light ray 604b does not encounter a sidewall of the microtube 536g and travels through the microtube 536g to the filter 528. In another example, light ray 604c may encounter microtube 536h of the collimator 530 at a third angle, where the light ray 604c does not encounter a sidewall of the microtube 536h and travels through the microtube 536h to the filter 528. In another example, light ray 604d may encounter microtube 536h of the collimator 530 at a fourth angle, where the light ray 604d encounters a sidewall of the microtube 536h such that the light ray 604d is absorbed by the sidewall.

In another embodiment, whether a light ray passes through one of the microtubes 536 of the collimator 530 may be based on an angle that the light ray enters the microtube 536 and a distance the light ray is from a sidewall of the microtube 536 as the light ray enters the microtube 536. For example, light ray 604a may enter microtube 536b at a relatively steep angle such that the light ray 604a strikes the side wall of microtube 536b. The steep angle may exceed, for example, 15 degrees. In another example, the light ray 604d may enter the microtube 536h at a relatively gradual angle (such as an angle of less than 15 degrees) but the light ray 604d may enter the microtube 536h below a threshold distance from the sidewall of the microtube 536h such that the light ray 604d is absorbed by the sidewall. In another example, light ray 604b may enter microtube 536g and/or light ray 604c may enter microtube 536h below the threshold angle and/or above the threshold distance from the sidewalls of microtubes 536g and 536h such that the light rays 604b and 604c may not strike a sidewall of the microtubes 536g and 536h and may pass through the microtubes 536g and 536h to the filter 528. The number of light rays emitted from the light source 602, the number of light rays received at the collimator, the angle of the light rays, the size and/or shape of the collimator 530 and/or the microtubes 536, and/or the wavelength or intensity of the light rays are not intended to be limiting and may vary.

In another embodiment, to absorb the light rays that strike or impact a sidewall of a microtube 536, the collimator 530 or at least a portion of the collimator 530 (such as the sidewalls of the collimator 530) may include material that may absorb the light rays. In one embodiment, the material of the collimator 530 or a portion of the collimator 530 that absorbs the light rays may include carbon, CNTs, tungsten, nickel, UV-opaque plastic, UV-opaque photoresists, and so forth.

When the light rays 604b and 604c pass through the microtubes 536g and 536h of the collimator, the light rays 604b and 604c may then pass through the filter 528 and/or the fill material, the filter 528 may filter out specific wavelengths of light and/or ranges of wavelengths at different areas of the filter 528. In another example, the filter 528 may be a linear variable filter or a continuously variable filter whose spectral properties vary continuously along one dimension or plane of the filter 528 to filter out light rays of different wavelengths depending on where the light rays strike along the surface of the filter 528. Once the filter 528 filters out unwanted or non-desirable wavelengths of light, the remaining light rays at the wanted or desired wavelengths may be received at the optical sensor 532. The light sensor may then measure the light intensity, the luminous intensity, or the pixel levels of the light rays received at the optical sensor 532. The optical sensor 532 may send data indicative of the measurements by the optical sensor 532 to a processing device for the processing device to analyze and determine various information. The various information may be information associated with the light rays, information associated with an object the light rays are reflected off of, information about the light source 602, and so forth.

Figure 6B:
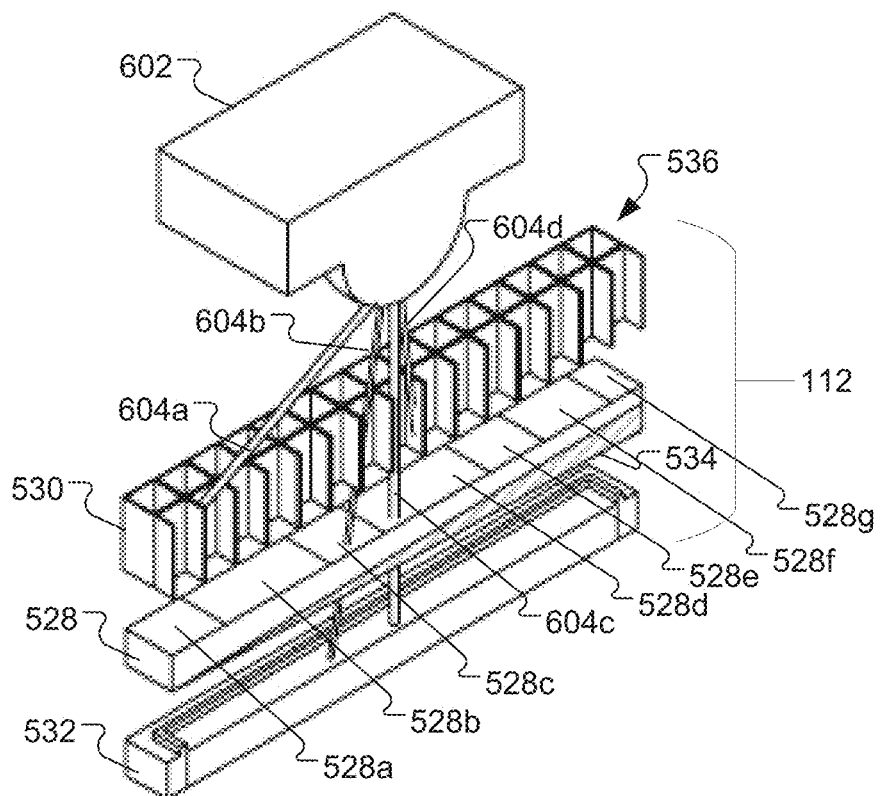
FIG. 6B illustrates a perspective cross-sectional view of the light source emitting the light rays into the first sensor, according to an embodiment.

FIG. 6B illustrates a perspective cross-sectional view of the light source 602 emitting the light rays 604a-d into the first sensor 112, according to an embodiment. Some of the features in FIG. 6B are the same as or similar to some of the features in FIGS. 1-6A as noted by same reference numbers, unless expressly described otherwise. As discussed above, the light source 602 may emit light rays 604a-d that may be absorbed by the sidewalls of the microtubes 536 or pass through the microtubes 536 of the collimator 530. In one embodiment, the light rays 604b and 604c may pass through the microtubes 536g and 536h of the collimator 530. As further discussed above, the filter 528 may be a linear variable filter, a continuously variable filter, a filter with different bandpass filters that may filter out different wavelengths of light at different locations along the surface of the filter 528. For example, the filter 528 may include the first region 528a, the second region 528b, the third region 528c, the fourth region 528d, the fifth region 528e, the sixth region 528f, and the seventh region 528g for filtering different wavelengths of light or different wavelength ranges of light.

Figure 6C:
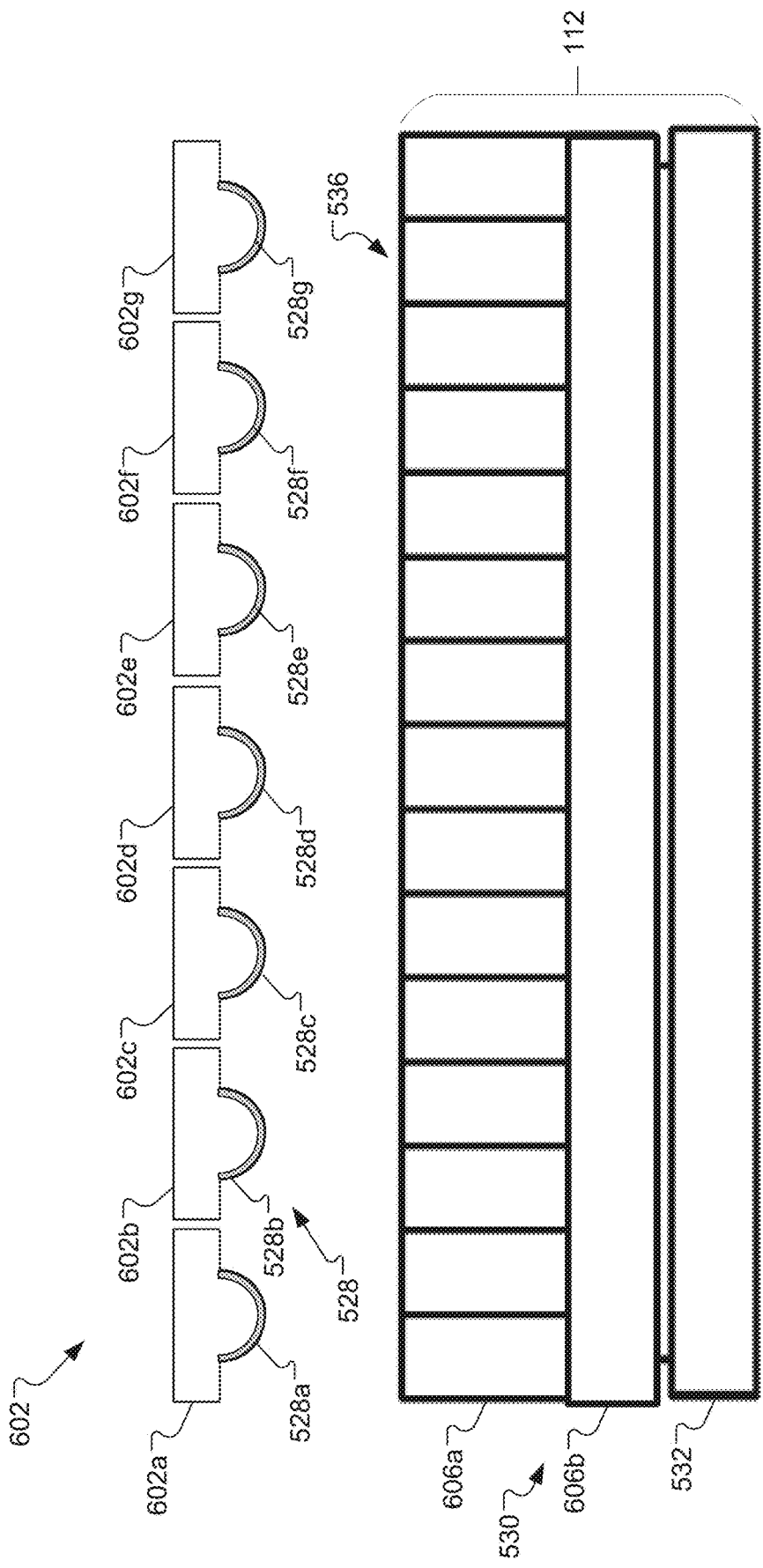
FIG. 6C illustrates a plurality of the light source positioned adjacent to regions of a filter, according to an embodiment.

FIG. 6C illustrates a plurality of light sources 602a-g positioned adjacent to the filter regions 528a-g, according to an embodiment. Some of the features in FIG. 6C are the same as or similar to some of the features in FIGS. 1-6B as noted by same reference numbers, unless expressly described otherwise. In an embodiment, the light source 602 may include a plurality of illuminators 602a-g. The filter 528 may be disposed adjacent to the illuminators 602a-g. In an embodiment, one or more of the filter regions 528a-g may be disposed adjacent to one or more of the illuminators 602a-g. For example, the filter region 528a may be disposed adjacent to the illuminator 602a; the filter region 528b may be disposed adjacent to the illuminator 602b; and so forth. In one embodiment, the filter regions 528a-g may be integrated with the illuminators 602a-g. In one embodiment, one or more of the illuminators 602a-g may be a broadband and/or a narrow band light source.

In one embodiment, one or more of the filter regions 528a-g may be a broadband and/or a narrow band light source. For example, the illuminators 602a-g may include a broadband light source emitting wavelengths ranging from 700 nm to 2500 nm, the filter region 528a may have a passband ranging from 700 nm to 1000 nm, the filter region 528b may have a narrow passband ranging from 950 nm to 1250 nm, the filter region 528c may have a narrow passband ranging from 1200 nm to 1500 nm, the filter region 528d may have a narrow passband ranging from 1450 nm to 1750 nm, the filter region 528e may have a narrow passband ranging from 1700 nm to 2000 nm, the filter region 528f may have a narrow passband ranging from 1950 nm to 2250 nm, and/or the filter region 528g may have a narrow passband ranging from 2200 nm the 2500 nm. In another example, the illuminators 602a-g may include a first light source emitting wavelengths ranging from 700 nm to 1300 nm, a second light source emitting wavelengths ranging from 1300 nm to 1900 nm, and/or a third light source emitting wavelengths ranging from 1900 nm to 2500 nm. The illuminators 602a-g may include a plurality of one or more of the broadband light sources. For example, the illuminators 602a-b may include the first light source, the illuminators 602c-d may include the second light source, and/or the illuminators 602e-g may include the third light source. The filter regions 528a-g may include the passband embodiments. The filter regions 528a-b may be disposed adjacent to the illuminators 602a-b; the filter regions 528c-d may be disposed adjacent to the illuminators 602c-d, and/or the filter regions 528e-g may be disposed adjacent to the illuminators 602e-g. The foregoing wavelengths are provided as examples only, and are not intended to be limiting on the light sources and/or filters which may be incorporated as described herein.

In an embodiment including multiple illuminators that emit different ranges of wavelengths, the optical sensor 532 may act as a time division multiplexer. The processing device electronically coupled to the illuminators 602a-g may pulse the illuminators 602a-g at different times, such as pulsing the illuminator 602a at a first time, the illuminator 602b at a second time, and so forth. The optical sensor 532 may communicate intensities of light to the processing device. To determine wavelengths detected by the optical sensor 532, the processing device may correlate the intensities communicated by the optical sensor 532 and the time the optical sensor 532 transmits signals with the times the illuminators 602a-g were pulsed. The time may be an absolute time, such as a calendar time, or a relative time.

In an embodiment, the wearable device 100 may include a flexible band such as the band 106, the light source 326, the optical filter 528, the optical sensor 532, and the collimator 530. The flexible band may be designed to flex into a curvilinear shape, and may have a shape, size, and flexibility designed for attaching the flexible band to a wrist of a user. The wrist may include a dermal layer along an underside of the wrist and a blood vessel within the wrist adjacent to the dermal layer along the underside of the wrist. The light source 326 may be embedded in the flexible band. The light source 326 may emit light to interrogate the wrist, the dermal layer, or the blood vessel. The light may include a constituent wavelength, where the constituent wavelength provides an indication of a state, condition, or constituent of the blood vessel or material in the blood vessel by reflection from or transmission through the blood vessel or the material in the blood vessel. The light source 326 may be positioned in the flexible band to emit, as the user wears the flexible band, the light towards the wrist. The optical filter 528 may be integrated into the flexible band, and oriented in the flexible band to isolate the constituent wavelength. The optical filter 528 may have a passband to isolate the constituent wavelength from other wavelengths of the light. The optical sensor 532 may be integrated into the flexible band and positioned in the flexible band to receive the constituent wavelength. The optical sensor 532 may be is positioned in the flexible band to receive, as the user wears the band, the constituent wavelength through the wrist, the dermal layer, the blood vessel, or the material in the blood vessel. The collimator 530 may be integrated into the flexible band and may include: a glass substrate 606a substantially transparent to the constituent wavelength; a patterned thin film layer of iron patterned on the glass substrate and adhered to the glass substrate; and a carbon nanotube grid structure 606b coupled to the glass substrate 606a. The patterned thin film layer of iron may form a basis for the carbon nanotube grid structure 606b. The carbon nanotube grid structure 606b may be grown on the patterned thin film layer of iron. The collimator 530 may be positioned in the flexible band to collimate the light before the light is received by the optical sensor 532.

In an example of the embodiment, the carbon nanotube grid structure 606b may be grown upwards from a first surface of the glass substrate 606a. The glass substrate 606a may be integrated into the flexible band such that the first surface and the carbon nanotube grid structure 606b are embedded within the band and a second surface of the glass substrate 606a opposite the first surface is flush with an inside surface of the flexible band, such as the inside surface 106a of the band 106. The glass substrate 606a may form a hermetic seal with the flexible band, sealing the carbon nanotube grid structure 606b, the optical filter 528, or the optical sensor 532 within the flexible band.

In another example, the glass substrate 606 may include borosilicate glass. The borosilicate glass may be scratch resistant to protect the collimator 530, the optical filter 528, and/or the optical sensor 532, and to minimize interference with the light by scratches to the glass substrate 606. The carbon nanotube grid structure 606b may include: a wall having a height ranging from 30 microns to 500 microns; and/or a through-channel having a width ranging from 10 microns to 150 microns. The collimator 530 and the optical filter 528 may be stacked together in the flexible band. The carbon nanotube grid structure 606b may be positioned between the glass substrate 606a and the optical filter. The collimator 530 and the optical sensor 532 may be stacked together in the flexible band. The carbon nanotube grid structure 606b may be positioned between the glass substrate 606a and the optical sensor 532.

In another example, the collimator 530 may include an adhesive adhering the carbon nanotube grid structure 606b to the glass substrate 606a. The adhesive may be transparent to the constituent wavelength, and/or the adhesive may couples the carbon nanotube grid structure 606b to the glass substrate 606a. The adhesive may be patterned to match a pattern of the carbon nanotube grid structure 606b on the glass substrate 606a. In another example, the glass substrate 606a may include a patterned etch. A pattern of the patterned etch may match the carbon nanotube grid structure 606b. The carbon nanotube grid structure 606b may be positioned in the patterned etch in the glass substrate 606a. In another example, the glass substrate 606a may include a thickness ranging from 300 microns to 3 millimeters.

In another example, the optical filter 528 may include a thin film linear variable filter. The thin film linear variable filter may be deposited on a first side of the glass substrate 606a. The collimator 530 may be is positioned on a second side of the glass substrate 606a opposite the first side of the glass substrate 606a. In another example, the glass substrate 606a may include a dye having the passband to allow the constituent wavelength to pass through the glass substrate 606a unattenuated.

In an embodiment, the wearable device 100 may include the band 106, the light source 326, the optical sensor 532, the optical filter 528, and the glass substrate 606a. The band 106 may have a shape, size, and flexibility designed for attaching the band 106 to a body part of a user. The light source 326 may be embedded in the band 106. The light source 326 may emit light to interrogate the body part, the light comprising a constituent wavelength that provides and indication of a feature of the body part. The light source 326 may be is positioned in the band 106 to emit, as the user wears the band 106, the light towards the body part. The optical sensor 532 may be integrated into the band 106 and positioned in the band 106 to receive the constituent wavelength. The optical sensor 532 may be positioned in the band 106 to receive, as the user wears the band 106, the constituent wavelength through the body part. The glass substrate 606a may be integrated into the band 106 and oriented in the band 106 to receive the light through the body part as the user wears the band 106. The glass substrate 606a may include a grid structure etched into the glass substrate and carbon nanotubes disposed in the grid structure forming walls of the grid structure.

In an example of the embodiment, the etching of the grid structure may form an adhesion surface for the carbon nanotubes, the carbon nanotubes adhered to the grid structure. The carbon nanotubes may be grown upwards from a first surface of the glass substrate 606a relative to a horizontal plan. The glass substrate 606a may be flipped over relative to the horizontal plane and the carbon nanotubes may integrated into the band 106 facing downwards relative to the horizontal plane.

In another example, the optical filter 528 and the glass substrate 606a may be ordered in the band 106 so that the light passes, as the user wears the band 106, from the body part through the optical filter 528 before passing through the grid structure. The light may be filtered into the constituent wavelength before the constituent wavelength is collimated and passed to the optical sensor 532. The glass substrate 606a and the optical filter 528 may be ordered in the band 106 so that the light passes, as the user wears the band 106, from the body part through the grid structure before passing through the optical filter 528. The light may be collimated before being filtered into the constituent wavelength and passing to the optical sensor 532.

In another example, an etch pattern of the grid structure may correlate with a pixel structure of the optical sensor 532. The walls of the grid structure may be aligned with boundaries between individual pixels of the optical sensor 532. The grid structure etched into the glass substrate may have a varying thickness, the walls having a corresponding varying thickness.

In an embodiment, the wearable device 100 may include the band 106, the light source 326, the optical sensor 532, and the glass substrate 606a. The band 106 may have a shape, size, and flexibility designed for attaching the band 106 to a body part of a user. The light source 326 may be embedded in the band 106. The light source 326 may emit light to interrogate the body part, the light including a constituent wavelength that provides an indication of a feature of the body part. The light source 326 may be positioned in the band 106 to emit, as the user wears the band 106, the light towards the body part. The optical sensor 532 may be integrated into the band 106 and positioned in the band 106 to receive the constituent wavelength. The optical sensor 532 may be positioned in the band 106 to receive, as the user wears the band 106, the constituent wavelength through the body part. The glass substrate 606a may be integrated into the band 106 and oriented in the band 106 to receive the light through the body part as the user wears the band 106. The glass substrate 606a may include the optical filter 528 and the carbon nanotube grid structure 606b. The optical filter 528 may isolate the constituent wavelength from the light, where the optical filter 528 has a passband to isolate the constituent wavelength from other wavelengths of the light. The carbon nanotube grid structure 606b may include walls and through-channels, and may be adhered to the glass substrate 606a. The optical filter 528 may be positioned on a first side of the glass substrate 606a and the carbon nanotube grid structure 606b may be positioned on a second side of the glass substrate 606a opposite the first side of the glass substrate 606a.

Figures 7A, 7B, 7C:
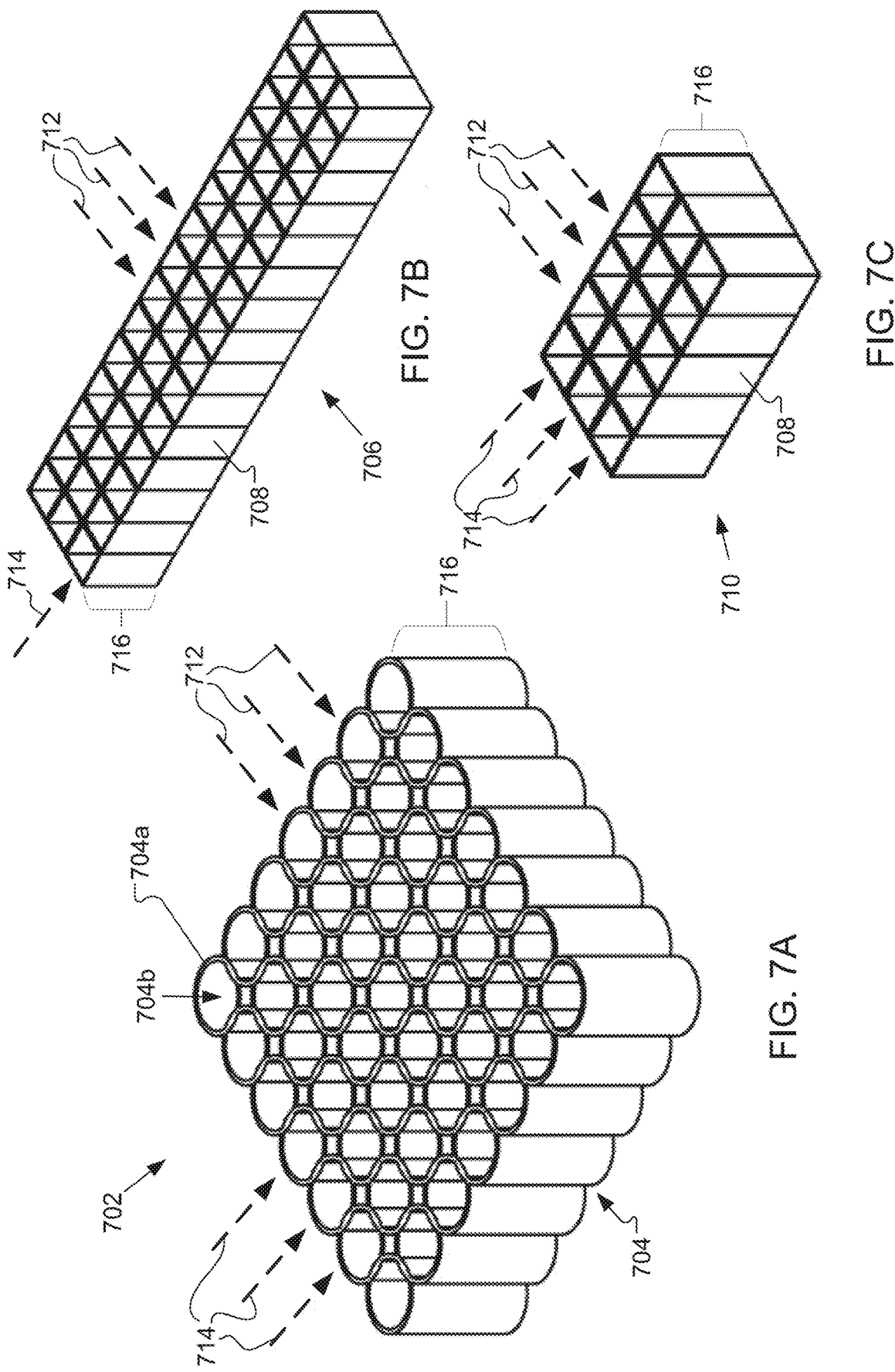
FIG. 7A illustrates an embodiment of a collimator arranged in a first two-dimensional array of cylindrical microtubes, according to an embodiment.
FIG. 7B illustrates an embodiment of a collimator arranged in a second two-dimensional array, including square microtubes, according to an embodiment.
FIG. 7C illustrates an embodiment of a collimator arranged in a third two-dimensional array, including the square microtubes illustrated in FIG. 7B, according to an embodiment.

FIG. 7A illustrates an embodiment of a collimator arranged in a first two-dimensional (2D) array 702, according to an embodiment. Some of the features in FIG. 7A are the same as or similar to some of the features in FIGS. 1-6C as noted by same reference numbers, unless expressly described otherwise. In an embodiment, the collimator may be the collimator 530. The collimator may include a cylindrical microtube 704. The cylindrical microtube 704 may be the same as or similar to the microtubes 536a-o. A plurality of the cylindrical microtube 704 may form the first two-dimensional array 702. The first 2D array 702 may include a rows 712 and/or columns 714. For example, the first 2D array 702 may include 7 rows 712 and/or 7 columns 714. The cylindrical microtube 704 may be circular. A number of the rows 712 may equal a number of the columns 714. The circular cylindrical microtubes 704 may be aligned such that the collimator may be square-shaped. The circular cylindrical microtubes 704 may be aligned such that the collimator may be trapezoid-shaped. One or more of the plurality of cylindrical microtubes 704 may have an ellipsoid cross-sectional shape such that, as a number of the rows 712 equals a number of the columns 714, the collimator may form a rectangle. In various embodiments, the first 2D array 702 may form any of a variety of geometric and/or non-geometric shapes, such as a square, a rectangle, a diamond, a parallelogram, a trapezoid, a polygon, a circle, a geometric pattern, a fractal geometry, and so forth.

A number of cylindrical microtubes 704 in the rows 712 and/or the columns 714 may vary according to the shape of the first 2D array 702. For example, a first row of the rows 712 may have 7 cylindrical microtubes 704, a second row of the rows 712 adjacent to the first row may have 8 cylindrical microtubes 704, a third row of the rows 712 adjacent to the second row may have 6 cylindrical microtubes 704, and so forth. In an embodiment, a first column of the columns 714 may have 100 cylindrical microtubes 704, a second column of the columns 714 adjacent to the first column may have 105 cylindrical microtubes 704, a third column of the columns 714 adjacent to the second column may have 113 cylindrical microtubes 704, and so forth.

In one embodiment, each cylindrical microtube 704 may have similar or the same dimensions. In another embodiment, some cylindrical microtubes 704 may have different dimensions than other cylindrical microtubes 704. For example, some cylindrical microtubes 704 may have a different height than other cylindrical microtubes 704. In another example, some cylindrical microtubes may have different diameters than other cylindrical microtubes 704. In some embodiments, a dimension of the cylindrical microtubes 704 may correspond to a filter region over which the cylindrical microtubes 704 may be disposed. The filter region may have a passband of wavelengths. The dimension of the cylindrical microtubes 704 may correspond to the passband.

In an embodiment, the cylindrical microtube 704 may be defined by a wall 704a encompassing a through-channel 704b. The wall 704a may be formed of one or more nanotubes. In an embodiment, the wall 704a may be formed of a forest of nanotubes. The nanotube may include a CNT. The CNT may be a single-walled CNT (SWCNT), a double-walled CNT (SWCNT), and/or a multi-walled CNT (MWCNT). The nanotube forest may include one or more SWCNTs, DWCNTs, and/or MWCNTs. The nanotubes may be aligned to form the wall 704a. In an embodiment, the nanotubes may be aligned along a length of the wall 704a, a height of the wall 704a (such as may be described and/or illustrated regarding FIG. 11B), and/or a width of the wall 704a. The nanotube forest may be infiltrated with a bolstering material, where "bolster" may refer to a property of a material that increases resistance against an applied force of the material and/or another material with which the material is incorporated. In various embodiments, the bolstering material may include a metal such as gold, silver, platinum, iron, nickel, cobalt, and so forth. In an embodiment, the bolstering material may include carbon. In an embodiment, the bolstering material may include graphene.

In an embodiment, the collimator may be integrated into a sensor, such as the first sensor 112. The sensor may include the collimator and a filter, such as the filter 528. A number and/or arrangement of the plurality of cylindrical microtubes 704 may correspond to a shape of a boundary of the filter. The filter may include one or more boundaries corresponding to a transition within the filter from a one region to another region, which may be referred to as a filter region boundary. For example, the filter 528 includes the first region 528a and the second region 528b. A transition point from the first region 528a to the second region 528b may represent an embodiment of the filter region boundary. Accordingly, the regions of the filter may have a shape, and a shape of the filter region boundary may correspond to one or more of the filter region shapes. The arrangement of the plurality of cylindrical microtubes 704 may, in an embodiment, align a first set of the plurality of cylindrical microtubes 704 over the first filter region and a second set of the plurality of cylindrical microtubes 704 over the second filter region adjacent to the first set of the plurality of cylindrical microtubes 704. A boundary between the first set of the plurality of cylindrical microtubes 704 and the second set of the plurality of cylindrical microtubes 704 may have a shape the same as or similar to the shape of the filter region boundary.

In one embodiment, the filter may have a thickness that varies along a length of the filter, which may be referred to as a gradient of the filter. The filter may include a continuous line running perpendicular to the gradient having a fixed thickness, which may be referred to as a contour line. The filter region may correspond to a segment of the length of the filter with a fixed change in thickness over the segment that corresponds to a range of wavelengths that pass through the filter region. In an embodiment, the filter region boundary may be formed by the contour line between the first region and the second region. The contour line may be straight, curved, linear, non-linear, and so forth. The arrangement of the plurality of cylindrical microtubes 704 may, in an embodiment, align the boundary between the first set of the plurality of cylindrical microtubes 704 and the second set of the plurality of cylindrical microtubes 704 with the contour line.

In an embodiment, alignment of the boundary between the first set of the plurality of cylindrical microtubes 704 and the second set of the plurality of cylindrical microtubes 704 with the contour line may increase precision of measurement. The filter may have limitations to precision from defects and/or limitations in a manufacturing process of the filter. The limitations may include the contour line being jagged, curved, and/or non-linear, and/or the contour-line not being perpendicular with an outside edge of the filter. In various embodiments, decreasing and/or eliminating the defects and or limitations of the filter may be associated with increasing costs of preparing the filter. Aligning the cylindrical microtube 704 boundary with the contour line may allow for similar precision using a low-cost filter as may be achieved using a high-cost filter. If a high-cost filter does not achieve a sufficient precision, aligning the cylindrical microtube 704 boundary with the contour line may allow for increased precision of the miniaturized spectrometer using the high-cost filter. Additionally, aligning the cylindrical microtube 704 boundary with the contour line may improve a precision of the miniaturized spectrometer by segmenting collimated light to specific regions of the filter. Furthermore, in various embodiments, the cylindrical microtubes may be misaligned with the contour line.

In an embodiment, the cylindrical microtube 704 may have a lengthwise shape 716. The lengthwise shape 716 of the cylindrical microtube 704 may define a height of the cylindrical microtube 704. The lengthwise shape 716 may be formed by the wall 704a. The lengthwise shape 716 may be straight, curved, linear, non-linear, and so forth. In an embodiment, the curved and/or non-linear lengthwise shape 716 of the cylindrical microtube 704 may reduce an intensity of light passing through the cylindrical microtube 704, and/or may increase alignment of light rays passing through the cylindrical microtube 704 and therefore the collimation function of the collimator. In an embodiment, the wall 704a may have a uniform or a non-uniform thickness. The non-uniform thickness of the wall 704a may define the lengthwise shape 716.

In another embodiment, the wall 704a may have a surface roughness. The surface roughness may define the lengthwise shape 716. The surface roughness of the wall 704a may be controlled during a preparation process of the wall 704a. For example, in an embodiment including CNTs, the surface roughness of the wall 704a may be directly related to a thickness of a catalyst layer on which the CNTs are grown. In an embodiment, a greater surface roughness of the wall 704a may reduce a reflectivity and/or a reflectance of the wall 704a, thereby increasing the collimation function of the collimator. In an embodiment of the wall 704a including infiltrated CNTs, the reflectivity and/or reflectance of the wall 704a may be reduced by reducing the infiltration. In another embodiment, the wall 704a may be etched, such as by plasma etching, to increase the roughness of the wall 704a and/or reduce the reflectivity and/or reflectance of the wall 704a.

FIG. 7B illustrates an embodiment of the collimator arranged in a second 2D array 706, having a square microtube 708. Some of the features in FIG. 7B are the same as or similar to some of the features in FIGS. 1-7A as noted by same reference numbers, unless expressly described otherwise. The square microtube 708 may be the same as or similar to the microtubes 536a-o. The second 2D array 706 may include a plurality of the square microtube 708. The second 2D array 706 may include the rows 712 and/or the columns 714. For example, the second 2D array 706 may include 15 of the rows 712 and/or 3 of the columns 714.

A length of the second 2D array 706 may be greater than a width of the second 2D array 706, or vice versa. This may be due to the number of rows 712 being greater than the number of columns 714, or vice versa. In an embodiment, the relative dimensions of the second 2D array 706 may correspond to a shape of the sensor into which the collimator may be integrated, and/or a shape of an electronic device into which the collimator and/or the sensor may be integrated. For example, the second 2D array 706 may be integrated into a sensor such as the first sensor 112. The sensor 112 may be integrated into a band of a wearable device, such as the band 106 of the wearable device 100. The band may have a length greater than a width of the band. Accordingly, the relative dimensions of the second 2D array 706 may correspond to the relative dimensions of the band.

In another embodiment, the relative dimensions of the second 2D array 706 may correspond to relative dimensions of a structure the sensor into which the second 2D array 706 is integrated may take measurements from. For example, the sensor may take measurements of light reflected from a segment of a vein and/or an artery. The segment may have a length greater than a diameter of the segment. The second 2D array 706 may have a length the same as or approximately the same as the segment length. The second 2D array 706 may have a width the same as or approximately the same as the segment diameter. In another example, the second 2D array 706 may have a width greater than the segment diameter by up to 100 percent, up to 75 percent, up to 50 percent, up to 40 percent, up to 30 percent, up to 25 percent, up to 20 percent, up to 15 percent, up to 10 percent, and/or up to 5 percent. The larger width of the second 2D array 706 compared to the segment diameter may increase an amount of light captured by the second 2D array 706 that may be reflected from the segment. The sensor may have similar dimensions as the second 2D array 706. In yet another example, the second 2D array 706 may have a width smaller than the segment diameter by up to 5 percent, up to 10 percent, up to 15 percent, up to 20 percent, up to 25 percent, up to 30 percent, up to 40 percent, up to 50 percent, and/or up to 75 percent. The smaller width of the second 2D array 706 compared to the segment diameter may maximize an amount of light the second 2D array 706 captures that may be reflected by the segment compared to an amount of light the second 2D array 706 captures that may be reflected by another structure.

The concepts and/or details of the foregoing discussion regarding the second 2D array 706 may similarly apply to the first 2D array 702 discussed and illustrated regarding FIG. 7A, embodiments of microtubes having different shapes other than circular or square, the collimator 530 described and illustrated herein, and/or the first sensor 112 described and illustrated herein.

FIG. 7C illustrates an embodiment of the collimator arranged in a third 2D array 710, including the square microtube 708 illustrated in FIG. 7B, according to an embodiment. Some of the features in FIG. 7C are the same as or similar to some of the features in FIGS. 1-7B as noted by same reference numbers, unless expressly described otherwise. The third 2D array 710 may include a plurality of the square microtube 708. The third 2D array 710 may include the rows 712 and/or the columns 714. In one embodiment, the third 2D array 710 may include 5 of the rows 712 and/or 3 of the columns 714. The concepts and/or details of the discussion above regarding the second 2D array 706 may similarly apply to the third 2D array 710.

Figure 8:
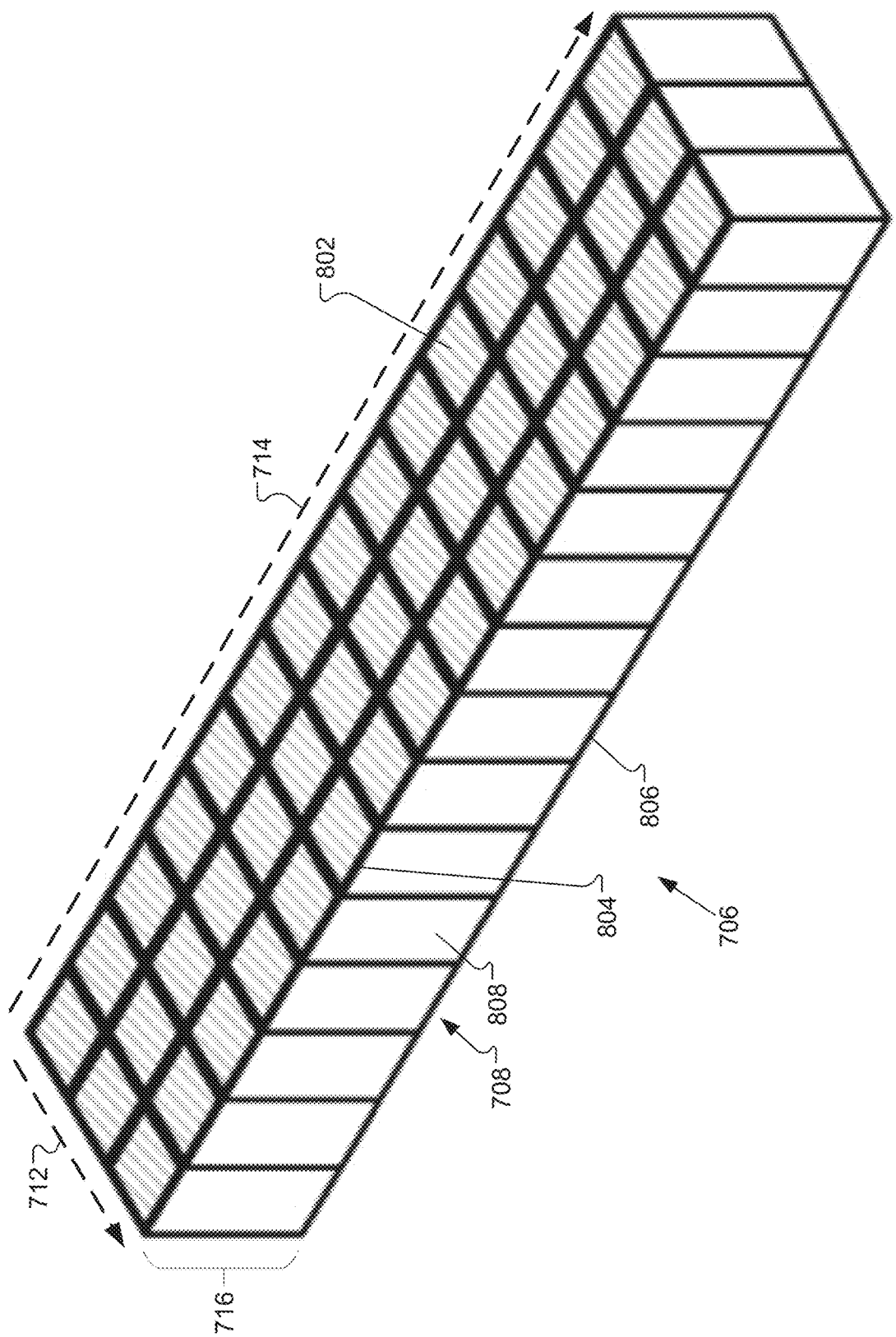
FIG. 8 illustrates an embodiment of the collimator illustrated in FIG. 7B, further including a filler, according to an embodiment.

FIG. 8 illustrates the second 2D array 706 illustrated in FIG. 7B, further including a filler 802, according to an embodiment. Some of the features in FIG. 8 are the same as or similar to some of the features in FIGS. 1-7C as noted by same reference numbers, unless expressly described otherwise. The filler 802 may be disposed within the microtube 708. The filler 802 may fill the microtube 708 such that the filler may be flush with a top edge of the microtube 708. The filler 802 may form a continuous surface with the top edge 804 of the microtube 708. In an embodiment, the filler 802 may form a filler surface over the top edge 804 of the microtube 708. In an embodiment, the filler 802 may for the filler surface over a bottom edge 806 of the microtube 708. In an embodiment, the filler 802 may coat a wall 808 of the microtube 708. In an embodiment, the filler 802 may surround the microtube 708 and/or the second 2D array 706. In an embodiment, the continuous surface and/or the filler surface may be smooth relative to a filter, such as the filter 528, and/or a sensor, such as the optical sensor 532. The filler 802 may enable a smooth interface between the collimator, the filter, and/or the sensor. The smooth interface may minimize scattering of light. Furthermore, the filler 802 may prevent debris from occluding the microtube 708. Additionally, the filler 802 may increase a rigidity of the second 2D array 706 and/or a resistance of the second 2D array 706 to one or more forces that may deform and/or break the second 2D array 706.

In various embodiments, the filler 802 may include a polymer that may be rigid and transparent to wavelengths of light to be detected by the optical sensor. The polymer may have low viscosity in a liquid and/or resin state to prevent damaging the microtubes 708 as the polymer is deposited on the 2D array 706. The filler 802 may be added to the second 2D array 706 by a process corresponding to a type of material of which the filler 802 is made. For example, in an embodiment including the polymer, the second 2D array 706 may be dipped in a volume of molten polymer to coat the second 2D array 706 in the polymer. In an embodiment, the filler 802 may be sprayed and/or spun onto the second 2D array 706. In one embodiment, a liquid resin may be poured over the second 2D array 706. The second 2D array 706 and resin may be placed into a vacuum chamber and the pressure inside the chamber may be reduced until air bubbles form in the resin and seep out of the resin. The 2D array 706 and resin may remain in the vacuum until all air has escaped the 2D array and resin. The pressure inside the chamber may be gradually increased back towards atmospheric pressure to press the resin into the microtubes 708. The resin may then be cured and/or cross-linked by exposer to hear and/or UV light to solidify the resin.

Materials for forming a miniaturized spectrometer, such as the first sensor 112, may be selected to minimize a difference in a refractive index between layers of the miniaturized spectrometer. The layers may include the collimator, the filter, and/or an optical sensor, such as the optical sensor 532. At an interface between the collimator and the filter, refraction of light passing through the layers may occur due to a difference in the respective refractive indices of the layers. The refraction may decrease an intensity of the light as the light impinges on the sensor. An amount of refraction as light transitions across the collimator-filter interface may correspond directly to the difference the respective indices of refraction of the collimator and the filter. Minimizing refraction across the collimator-filter interface may include matching as closely as possible the collimator index of refraction and the filter index of refraction. In various embodiments, the filter may have an index of refraction ranging from 1.4 to 2.0. In various embodiments, the filler 802 of the collimator may have an index of refraction ranging from 1.3 to 1.9. In a specific embodiment, the filter may have an index of refraction of 1.7. A polymeric compound may be selected for the filler 802 having an index of refraction of 1.7. The index of refraction of the filter and/or the polymeric compound may vary for differing wavelengths. Accordingly, materials may be selected for the filter and/or the polymeric compound such that the difference between the filter index of refraction and the polymeric compound index of refraction a selected range of wavelengths may be minimized.

Materials for forming one or more of the layers of the miniaturized spectrometer may be selected based on a reflectivity, respectively, of the materials. Minimizing the reflectivity of the materials may maximize an intensity $I_{trans}$ of impinging light transmitted through various interfaces between the layers and/or other media, such as air or a body tissue. The reflectance of the materials may vary for differing wavelengths. Accordingly, materials may be selected for the filter and/or the filler 802 which may, for wavelengths within a range from 400 nm to 450 nm, for wavelengths within a range from 725 nm to 775 nm, for wavelengths within a range from 1050 nm to 1100 nm, and/or for wavelengths within a range from 1550 nm to 1700 nm, have a reflectance less than or equal to 10%, less than or equal to 5%, and/or less than or equal to 1%.

In various embodiments, the filler 802 may filter light passing through the microtubes 708. For example, light impinging on the filler 802 at a first end of the microtubes 708 may have an initial spectral profile, which may include various wavelengths of various intensities. Light leaving the filler 802 at a second end of the microtubes 708 may have a filtered spectral profile, which may include a wavelength having a peak intensity with other wavelengths having significantly reduced and/or eliminated intensities. The filler 802 may include a dye for filtering the light. The filler 802 may have a surface structure which may induce interference and thereby filter the light. The filler 802 may include a dichroic filter.

The filler 802 may be integrated into embodiments of the collimator 530 having cylindrical microtubes. Inter-tube channels may be formed between the microtubes of the array 702. The inter-tube channels may be filled with the filler 802.

In an embodiment, the collimator 530 may include a first carbon nanotube structure, a second carbon nanotube structure, and the filler 802. The first carbon nanotube structure may include a first microtube that includes a first set of aligned carbon nanotubes infiltrated by carbon and a first through-channel and have a height to through-channel width aspect ratio between 3:1 to 10:1. The first set of aligned carbon nanotubes infiltrated by carbon may be configured to absorb a first portion of light that travels through the first through-channel at a first angle and impinges a side of a first through-channel portion. The first set of aligned carbon nanotubes infiltrated by the carbon may be configured to allow a second portion of the light that enters the first through-channel at a second angle to pass through from a top of the first through-channel to a bottom of the first through-channel. The second carbon nanotube structure may include a second microtube that includes a second set of aligned carbon nanotubes infiltrated by carbon and a second through-channel. The second carbon nanotube structure may have a height to through-channel width aspect ratio between 3:1 to 10:1. The second set of aligned carbon nanotubes infiltrated by carbon may be configured to absorb a third portion of the light that travels through the second through-channel at a third angle and impinges a side of a second through-channel portion. The second set of aligned carbon nanotubes infiltrated by the carbon may be configured to allow a fourth portion of the light that enters the second through-channel at a fourth angle to pass through from a top of the second through-channel to a bottom of the second through-channel. The first microtube and the second microtube may share a common structural portion to form an array of microtubes. The filler 802 may be disposed within the first through-channel or the second through-channel. The filler 802 may fill the first through-channel from a bottom of the first through-channel or the second through-channel to a top of the first through-channel or the second through-channel such that the filler 802 is flush with a bottom surface, i.e. the bottom edge 806, of the first through-channel or the second through-channel and a top surface, i.e. the top edge 804, of the first through-channel or the second through-channel. The filler 802 may be a transparent material to allow light to be transmitted through the first through-channel or the second through-channel without interfering with the light.

In an example of the embodiment, the first angle, the second angle, the third angle, or the fourth angle of the light is relative to a plane extending along the bottom surface of the collimator 530. The first angle or the second angle may correlate directly with the first carbon nanotube structure aspect ratio. The third angle or the fourth angle may correlate directly with the second carbon nanotube structure aspect ratio. The first angle or the third angle may range up to 85 degrees, up to 80 degrees, up to 75 degrees, up to 70 degrees, or up to 60 degrees. The second angle or the fourth angle may range from 85 degrees to 90 degrees, from 80 degrees to 90 degrees, from 75 degrees to 90 degrees, from 70 degrees to 90 degrees, or from 60 degrees to 90 degrees. A degree of the first angle or the second angle may be based a distance a ray of the first portion of light is from a wall of a first carbon nanotube structure.

In another example, the first carbon nanotube structure may include: a first wall comprising a first subset of carbon nanotubes infiltrated with carbon; a second wall comprising a second subset of carbon nanotubes infiltrated with carbon; a third wall comprising a third subset of carbon nanotubes infiltrated with carbon; and a fourth wall comprising a fourth subset of carbon nanotubes infiltrated with carbon. A thickness of the first wall may be different than a thickness of the second wall.

In another example, the collimator 530 may have a length between 5 mm and 9 mm and a width between 0.5 mm and 2 mm. The array of microtubes may include a plurality of microtubes, including the first microtube and the second microtube, that share common structural portions to form the square or rectangular array of microtubes 706. The first carbon nanotube structure may include a cylindrical wall of the first set of aligned carbon nanotubes forming a cylindrical microtube.

In another example, the carbon nanotube structure may include carbon nanotube material to absorb the first portion of the light with an average reflectance of less than or equal to 10 percent.

In an embodiment, the collimator 530 may include a carbon nanotube structure, and the filler 802. The carbon nanotube structure may include a microtube that includes a set of aligned carbon nanotubes infiltrated by carbon and a through-channel. The set of aligned carbon nanotubes infiltrated by carbon may be configured to absorb a first portion of light that travels through the through-channel at a first angle and impinges a side of a through-channel portion. The set of aligned carbon nanotubes infiltrated by the carbon may be configured to allow a second portion of light that enters the through-channel at a second angle to pass through from a top of the through-channel to a bottom of the through-channel. The filler 802 may be disposed within the through-channel. The filler 802 may fill the through-channel from a bottom of the through-channel to a top of the through-channel such that the filler 802 is flush with the bottom surface of the through-channel and the top surface of the through-channel. The filler 802 may be a transparent material to allow light to be transmitted through the through-channel without interfering with the light.

In an example of the embodiment, the filler 802 may be a polymer with a relatively low viscosity such that a resin of the polymer is configured to be deposited in the through-channel without damaging the microtube. The filler 802 may reinforce the microtube to increase a rigidity of the carbon nanotube structure. The filler 802 may have an index of refraction ranging from 1.3 to 1.9 based on a wavelength of light traveling through the through-channel.

In another example, the set of aligned carbon nanotubes infiltrated by carbon may form the wall 808 with a thickness ranging from 1 micron to 50 microns and the height 7016 ranging from 50 microns to 1000 microns.

In another example, the infiltration of the carbon into the set of aligned carbon nanotubes may create a roughness along a surface of the microtube. The roughness may be defined by lengthwise shape of the surface of the microtube. The surface roughness of the microtube may reduce a reflectivity of the surface of the microtube.

In an embodiment, the collimator 530 may include a carbon nanotube structure having a microtube that includes a set of aligned carbon nanotubes infiltrated by carbon and a through-channel. The carbon nanotube structure may have a defined height to through-channel width aspect ratio. The defined height to through-channel width aspect ratio may be based on a defined collimation to diffraction ratio. As the defined height to through-channel width aspect ratio increases light, collimation by the collimator may increase and diffraction by the collimator may decrease. The set of aligned carbon nanotubes infiltrated by carbon may be configured to absorb a first portion of light that travels through the through-channel at a first angle and impinges a side of a first through-channel portion. The set of aligned carbon nanotubes infiltrated by the carbon may be configured to allow a second portion of the light that enters the through-channel at a second angle to pass through from a top of the through-channel to a bottom of the through-channel.

In an example of the embodiment, the defined height to through-channel width aspect ratio may range from 3:1 to 10:1. The defined height to through-channel width aspect ratio may be 5:1. The set of aligned carbon nanotubes infiltrated by carbon may form the wall 808 with a thickness ranging from 1 micron to 50 microns and a height ranging from 50 microns to 1000 microns.

FIG. 9A illustrates a ray diagram 900 of light 902 passing through a microtube 904 and one or more layers of a miniaturized spectrometer such as the first sensor 112, according to an embodiment. Some of the features in FIG. 9A are the same as or similar to some of the features in FIGS. 1-8 as noted by same reference numbers, unless expressly described otherwise. The layers may include the collimator 530 and/or the filter 528. The microtube 904 may include a wall 906 and a through-channel 908. The wall 906 may have a thickness 906a and a height 906b. The thickness 906a may range from 1 micron to 50 microns, from 1 micron to 20 microns, from 1 micron to 10 microns, and/or from 4 microns to 5 microns. The height 906b may range from 50 microns to 1000 microns, from 100 microns to 900 microns, from 200 microns to 800 microns, from 300 microns to 700 microns, from 400 microns to 600 microns, from 450 microns to 550 microns, and/or from 225 microns to 275 microns. In a specific embodiment the height 906b may be 250 microns. The through-channel 908 may include a width 908a. The width may range from 10 microns to 300 microns, from 25 microns to 75 microns, from 40 microns to 60 microns, from 45 microns to 55 microns, from 50 microns to 250 microns, from 100 microns to 200 microns, and/or from 125 microns to 175 microns. In a specific embodiment, the through-channel width 908a may be 50 microns. The collimator 530 may include the filler 802.

In an embodiment, the wall thickness 906a, the wall height 906b, or the through-channel width 908a may form an aspect ratio of the microtube 904. The aspect ratio may, for example, include a ratio of the height 906b to the through-channel width 908a. The ratio may range from 1:6 to 100:1, from 1:2.5 to 20:1, from 1:1 to 16:1, and/or from 2:1 to 10:1. In an embodiment, the aspect ratio may be 5:1. In general, as the through-channel width 908a decreases, diffraction effects become more pronounced. However, as the aspect ratio increases, collimation increases. Accordingly, a balance may be struck between increasing collimation and decreasing diffraction. An aspect ratio which optimizes this balance may be approximately 3:1, 4:1, 5:1, 6:1, 7:1, 8:1, 9:1, and/or 10:1. In one embodiment, the optimal aspect ratio may be 5:1.

The dimensions of the collimator 530 may allow for incorporation of a spectrometer into a wearable device. A conventional spectrometer may have dimensions at least ranging upwards from multiple centimeters cubed. The size of a conventional spectrometer makes it impractical to integrate into a wearable, such as a wristband, headband, arm band, and so forth. In contrast, the collimator 530 may have overall dimensions ranging less than a centimeter in length and less than or equal to 500 microns thick (i.e. less than a thickness of 5 pieces of printer paper). When combined with an optical sensor such as the optical sensor 532 and a filter such as the filter 528, the elements may form a sensor, such as the first sensor 112, having a thickness of less than or equal to 4 mm, less than or equal to 3.5 mm, and/or less than or equal to 3 mm.

The light 902 may impinge on the collimator 530 with an angle of incidence $\theta_{incident}$. The filler 802 may refract the light 902 to an angle $\theta_{filler}$. The light 902 may pass through the through-channel 908 and may impinge on the filter 528 at the angle $\theta_{filler}$. The filter 528 may refract the light 902 to an angle $\theta_{filter}$. The angle $\theta_{incident}$, the angle $\theta_{filler}$, and/or the angle $\theta_{filter}$ may be determined according to Snell's Law, where the angle $\theta_{incident}$ may correspond to an index of refraction $n_{incident}$, the angle $\theta_{filler}$ may correspond to an index of refraction $n_{filler}$, and/or the angle $\theta_{filter}$ may correspond to an index of refraction $n_{filter}$. The index of refraction $n_{filler}$ may correspond to the material of the filler 802. The index of refraction $n_{filter}$ may correspond to the material of the filter 528. The index of refraction $n_{incident}$ may correspond to a material adjacent to the collimator 530. In an embodiment, the material adjacent to the collimator 530 may include air. In an embodiment, the material adjacent to the collimator 530 may include a polymer such as a flexible polymer. The flexible polymer may have a high transmissivity of the light 902, such as ranging from 80% to 100% transmissivity of the light 902. The flexible polymer may be a portion of a band, such as the band 106 of the wearable device 100. In an embodiment, the material adjacent to the collimator 530 may include a biological tissue. The tissue may be an epidermis, a dermis, a fatty tissue, a muscular tissue, a connective tissue, a bone, and so forth.

FIG. 9B illustrates a ray diagram 920 showing a shadow effect of the collimator 530 on light passing through the miniaturized spectrometer, according to an embodiment. Some of the features in FIG. 9B are the same as or similar to some of the features in FIGS. 1-9A as noted by same reference numbers, unless expressly described otherwise. In an embodiment, the light 902 may enter the collimator 530 at a normal angle of incidence. For light 902 entering the collimator 530 at the normal angle of incidence where the angle $\theta_{incident}$ and/or the angle $\theta_{filler}$ may be equal to zero, a transmission efficiency $I_{normal}$ of the collimator 530 may be proportional to the square of the through-channel width 908a divided by a square of the through-channel width 908a less the thickness 906a of the microtube wall 906. In embodiments where the collimator 530 includes a plurality of the microtube 904, the transmission efficiency of the collimator 530 may be a mean, median, and/or mode of the transmission efficiency of various of the plurality of microtubes 904.

In an embodiment, the light 902 may enter the collimator 530 at a non-normal angle of incidence, which may create a shadow 910. The shadow 910 may be a region adjacent to the microtube wall 906 through which no light passes for a given $\theta_{incident}$ because light that would otherwise pass through the shadowed region is blocked by the microtube wall 906. The non-normal angle of incidence and resulting shadow 910 may reduce transmission efficiency of the collimator 530. Accordingly, the shadowed transmission efficiency $I_{shadow}$ of the collimator 530 may be zero when the shadow 910 is greater than the through-channel width 908a, and/or may be proportional to the through-channel width 908a less a length of the shadow 910, the result divided by the through-channel width 908a. Using Snell's Law, the shadowed transmission efficiency of the collimator 530 may be determined using $\theta_{incident}$, the height 906b, and/or the refractive index $n_{filler}$ of the filler. As $\theta_{incident}$ increases, the transmission efficiency of the collimator 530 may reduce to zero.

In an embodiment, the filter 528 may have a thickness that is a fraction of the wall height 906b. For example, the filter 528 may include a thin film deposited on a substrate. The substrate may include a glass substrate, the substrate may include the collimator filler, and/or the substrate may include a photoreactive surface of the optical sensor 532. The filter thickness may be less than or equal to one tenth of the wall height. For example, the filter may have a thickness ranging from 10 nm to 100 nm. Accordingly, a shadow on the optical sensor 532 due to additional travel of the light through the filter 528 may be negligible relative to the shadow 910 on the filter 528 when calculating a transmission efficiency for the filter. In another embodiment, the filter 528 may have a thickness relative to the wall height that may render the difference between the shadow on the optical sensor and the shadow 910 non-negligible due to the filter 528 thickness. For example, the filter thickness may be greater than one tenth of the wall height. A reduction in the transmission efficiency of the filter 528 due to enhancement of the shadow created by the wall 906b may be determined similar to $I_{shadow}$.

In various embodiments, the reduction in transmission efficiency of the filter 528 due to enhancement of the shadow created by the wall 906b may be negated by a thick filter 528. Light which may have passed from a neighboring microtube may strike an area of the optical sensor 532 which may have otherwise been shadowed by the wall 906b. This may occur when the filter 528 is sufficiently thick to allow the light to travel far enough to bleed over from one microtube to the neighboring microtube.

FIG. 10A illustrates a ray diagram that correlates a gap 1002a between the collimator 530 and the optical sensor 532 with a region on the optical sensor 532 the light 902 will strike, according to an embodiment. Some of the features in FIG. 10A are the same as or similar to some of the features in FIGS. 1-9B as noted by same reference numbers, unless expressly described otherwise. A first segment 1008a of the optical sensor 532 aligned with the microtube 904 may be identified by a processing device coupled to the optical sensor 532 as detecting wavelengths within a range corresponding to a range of unfiltered light 902 that may pass through the microtube 904. The collimator 530 may be separated from the optical sensor 532 by a distance 1002. For example, the filter 528 may be disposed between the collimator 530 and the optical sensor 532, and the distance 1002 may include a thickness of the filter 528. In another example, the filler 802 may surround the microtube 904, and a portion of the filler 802 may be disposed between the microtube 904 and the optical sensor 532. The distance 1002 may include a thickness of the filler 802 disposed between the microtube 904 and the optical sensor 532.

A material disposed between the microtube 904 and the optical sensor 532 may have a refractive index $n_{gap}$, where "gap" may generically refer to any material disposed between the collimator 530 and the optical sensor 532. The refractive index may be the same as or different than the index of refraction $n_{filler}$. In various embodiments, light 902 having a non-normal incidence on the filler 802 may pass into the material disposed between the microtube 904 and the optical sensor 532 at an angle $\theta_{gap}$, which may correspond to the index of refraction $n_{gap}$. In an embodiment where $n_{gap}$ is equal to $n_{filler}$, the angle $\theta_{gap}$ may be equal to the angle $\theta_{filler}$. In an embodiment where $n_{gap}$ is less than $n_{filler}$, the angle $\theta_{gap}$ may be greater than the angle $\theta_{filler}$. In an embodiment where $n_{gap}$ is greater than $n_{filler}$, the angle $\theta_{gap}$ may be less than the angle $\theta_{filler}$.

The light 902 may pass through the microtube 904 from a top edge of the wall 906 to a bottom edge 1006 of the wall 906. In various embodiments, $n_{gap}$ may be less than $n_{filler}$. The light 902 may be refracted as it passes from the filler 802 towards a second sensor segment 1008b. In an embodiment having a first length of the distance 1002, the light 902 may strike the first sensor segment 1008a. In an embodiment having a second length of the distance 1002, the second length being greater than the first length, the light 902 may strike the second sensor segment 1008b. This may cause the processing device to identify the light 902 as having a wavelength and/or range of wavelengths associated with the second sensor segment 1008b, whereas the light 902 may actually have a wavelength and/or range of wavelengths associated with the first sensor segment 1008a. In various embodiments, $n_{gap}$ may be equal to $n_{filler}$. In an embodiment having the first length of the distance 1002, the light 902 may strike the first sensor segment 1008a. In an embodiment having the second length of the distance 1002, the light 902 may strike the second sensor segment 1008b. In various embodiments, $n_{gap}$ may be greater than $n_{filler}$. The light 902 may be refracted as it passes from the filler 802 towards the first sensor segment 1008b. The light 902 may strike the first sensor segment 1008a in an embodiment having the first length of the distance 1002 and in an embodiment having the second length of the distance 1002.

FIG. 10B illustrates a ray diagram 1020 that correlates the gap 1002a between the filter 528 and the sensor 532 with the region on the sensor 532 the light 902 may impinge, according to an embodiment. Some of the features in FIG. 10B are the same as or similar to some of the features in FIGS. 1-10A as noted by same reference numbers, unless expressly described otherwise. A first segment 1008a of the optical sensor 532 aligned with the first filter region 528a may be identified by a processing device coupled to the optical sensor 532 as detecting wavelengths within a range corresponding to a range of unfiltered light 902 that may pass through the first filter region 528a. The filter 528 may be separated from the optical sensor 532 by a distance 1002. For example, the collimator 530 may be disposed between the filter 528 and the optical sensor 532, and the distance 1002 may include a thickness of the collimator 530. In another example, the filter 528 may be an interference filter which may include a filtering surface 1004a and a filter substrate 1004b. The filtering surface 1004a may include a thin film that may transmit a wavelength or range of wavelengths while reflecting other wavelengths. The filter substrate 1004b may be transparent to the transmitted wavelength or range of wavelengths and the other wavelengths. The filtering surface 1004a may be deposited and/or adhered to the filter substrate 1004b. The filter substrate 1004b may provide a rigid support structure for the filtering surface 1004a, as the filter substrate 1004b may have a thickness many tens or hundreds of times a thickness of the filtering surface 1004a.

The distance 1002 between the filtering surface 1004a and the optical sensor 532 may determine whether the light 902 having non-normal incidence on the filter 528 and passing though the first filter region 528a may strike the first sensor segment 1008a or the second sensor segment 1008b. For a fixed angle of incidence on the filter $\theta_{incident}$ and fixed refractive indices $n_{filter}$ and $n_{gap}$ (where "gap" may refer to any material and/or space disposed between the filter surface 1004a and the optical sensor 532), the light 902 may strike the first sensor segment 1008a for a first value of the distance 1002 and may strike the second sensor segment 1008b for a second value of the distance 1002. A maximum value for the distance 1002 between the filter surface 1004a and the optical sensor 532 where the light 902 of fixed non-normal incidence may pass through the first filter region 528a and strike the first sensor segment 1008a may be $d_{max}$. A maximum value for $\theta_{incident}$ may be determined by various dimensions of the collimator 530, such as the height 906b of the microtube wall 906 and/or the width 908a of the through-channel 908. $d_{max}$ may vary with the maximum value for $\theta_{incident}$ and with varying values of $n_{filter}$ and $n_{gap}$.

In various embodiments, the processing device may correlate the first sensor segment 1008a with the first filter region 528a and the second sensor segment 1008b with the second filter region 528b. To ensure that light passing through the filter surface 1004a strikes the correct sensor segment, $d_{max}$ may be minimized. In one embodiment, the filter surface 1004a may be placed against the optical sensor 532. In another embodiment, the filter surface 1004 may be integrated with the optical sensor 532. For example, the optical sensor 532 may include a photodiode, and the filter surface 1004a may be deposited on the photodiode. In such an embodiment, the filter surface 1004 may be a narrowband filter and/or a discrete wavelength filter. In one embodiment, the collimator 530 may be positioned between the filter 528 and the optical sensor 532 and the filter surface 1004a may be placed against the collimator 530 facing the optical sensor 532. The collimator 530 may function to ensure that rays of the light 902 passing through the first filter region of 528a strike the first sensor segment 1008a and may absorb and/or reflect rays of the light 902 passing through the first filter region 528a that may have a trajectory to strike the second sensor segment 1008b.

FIG. 10C illustrates an orientation and structure of the collimator 530 relative to the optical sensor 532 that may reduce and/or eliminate crossing of light to a neighboring sensor segment, according to an embodiment. Some of the features in FIG. 10C are the same as or similar to some of the features in FIGS. 1-10B as noted by same reference numbers, unless expressly described otherwise. Where FIGS. 10A-B may illustrate side-view diagrams, FIG. 10C may illustrate a top-view schematic. In an embodiment, a filter, such as the filter 528 described regarding FIGS. 10A-B, may be disposed between the collimator 520 and the optical sensor 532. The filter may have a constant filtering function in a direction 1010 and may have a changing filtering function in a direction 1012. The constant filtering function may filter light along an indicated direction in a constant manner. For example, the filter may have the same passband at each point on the filter along the indicated direction corresponding to the constant filter function. The changing filtering function may filter light along an indicated direction in a changing manner. For example, the filter may have a different passband at each point on the filer along the indicated direction corresponding to the changing filter function. The thickness of the wall 906 may be greater for wall 906 aligned with the direction 1010 than for walls 906 aligned with the direction 1012.

In various embodiments, varying the thickness of the wall 906 may have similar effects to varying the distance 1002 described and/or illustrated regarding FIGS. 10A-B. Increasing the thickness of the wall 906 may reduce the width of the through-channel relative to a width of the first sensor segment 1008a. The reduced through-channel width may compensate for $n_{gap}$ (where "gap" may refer to material positioned between the collimator 530 and the optical sensor 532) being less than $n_{filler}$, and/or for the distance between collimator 530. Light, such as the light 902 described regarding FIGS. 10A-B, may be refracted towards the second sensor segment 1008b, but because the through-channel width is narrower due to the increased thickness of the wall 906, the light may strike the first sensor segment 1008a. In various embodiments, the thickness of the wall 906 may directly correspond to the distance between the collimator 530 and the optical sensor 532 to ensure light passing through the microtube 904 having a greatest angle $\theta_{filler}$ that may pass through the microtube 904 may strike the first sensor segment 1008a.

Figure 11B:
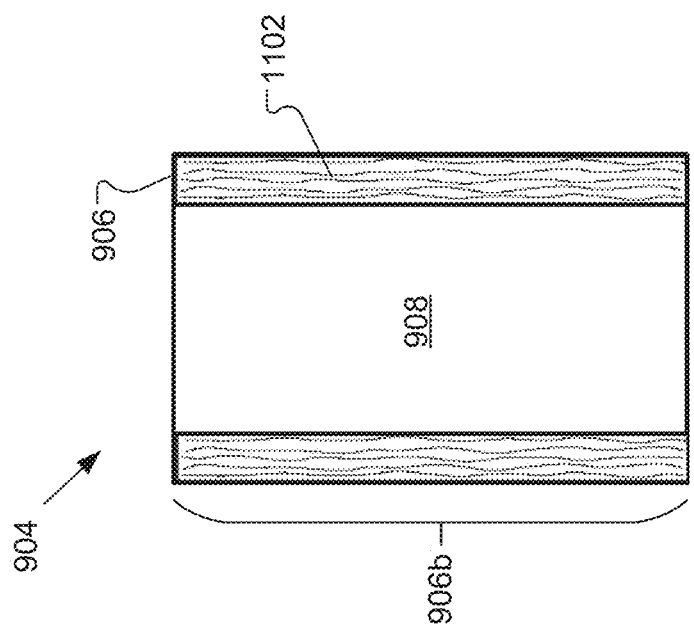
FIG. 11B illustrates a side view of a cross-section of a wall of a collimator, showing an internal structure of the wall, according to an embodiment.
Figure 11A:
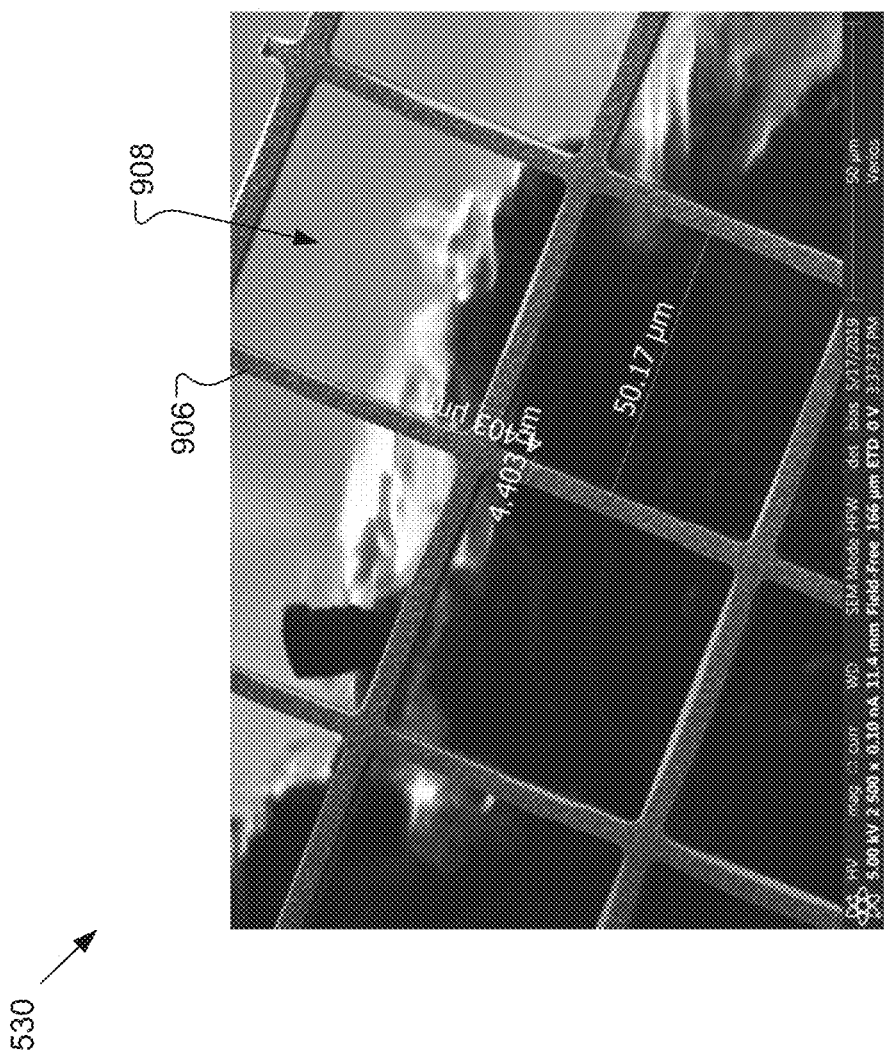
FIG. 11A is a picture of a section of a collimator, according to an embodiment.

FIG. 11A is a picture of a section of the collimator 530, according to an embodiment. Some of the features in FIG. 11A are the same as or similar to some of the features in FIGS. 1-10C as noted by same reference numbers, unless expressly described otherwise. The collimator 530 includes the wall 906 formed around the through-channel 908 to form a microtube. The wall may have a thickness ranging from 4 microns to 5 microns. The through-channel 908 may have a width ranging from 50 microns to 51 microns.

FIG. 11B illustrates a side view of a cross-section of the wall 906 of the microtube 904, showing an internal structure of the wall 906, according to an embodiment. Some of the features in FIG. 11B are the same as or similar to some of the features in FIGS. 1-11A as noted by same reference numbers, unless expressly described otherwise. The wall 906 may define the through-channel 908 of the microtube 904. The wall 906 may be formed of a nanotube forest 1102. The nanotube forest 1102 may be grown along the height 906b of the wall 906. The nanotube forest 1102 may have a density which may be measured as a ratio of a volume in the nanotube forest 1102 occupied by nanotubes to a volume of space in the nanotube forest 1102 between the nanotubes. In an embodiment, the ratio may be less than or equal to 1 percent. The ratio may be controlled by varying a particle size of a catalyst used to grow the nanotube forest 1102. A bolstering material may be infiltrated into the space between the nanotubes, such as the bolstering material described regarding FIG. 7A. The bolstering material may, in an embodiment, fill the space between the nanotubes. In an embodiment, the space between the nanotubes may include the bolstering material and voids. The voids may be devoid of material, or the voids may include gas molecules. In various embodiments, after infiltration, 80 percent to 90 percent of the volume in the nanotube forest may be occupied by the bolstering material.

Figure 11C:
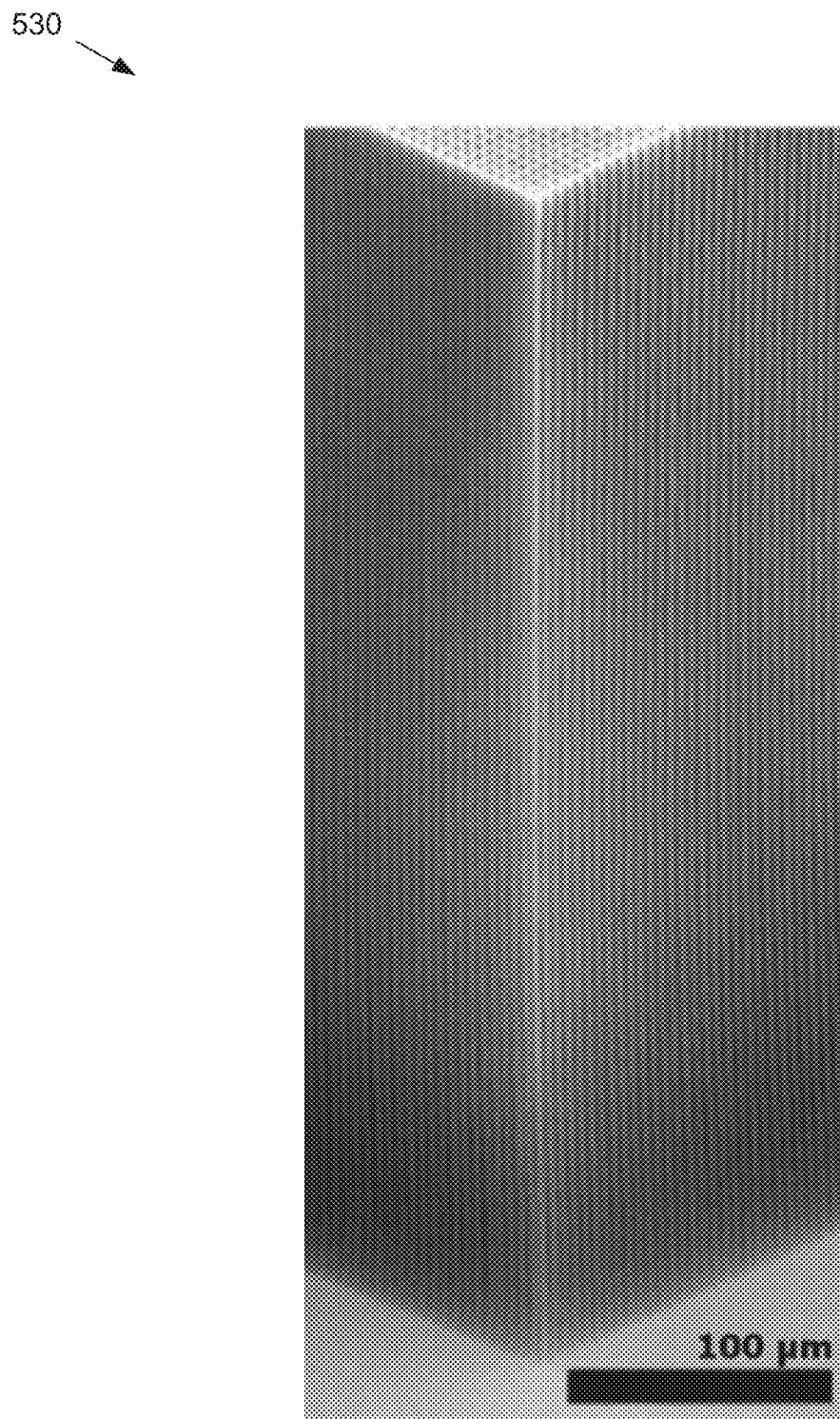
FIG. 11C illustrates a picture from a perspective view of the collimator 530, according to an embodiment.

FIG. 11C illustrates a picture from a perspective view of the collimator 530, according to an embodiment. Some of the features in FIG. 11C are the same as or similar to some of the features in FIGS. 1-11B as noted by same reference numbers, unless expressly described otherwise. In a specific embodiment, the collimator 530 may have a height of approximately 425 microns and a through-channel width of approximately 10 microns. Accordingly, the aspect ratio may be 42.5:1.

Figure 12B:
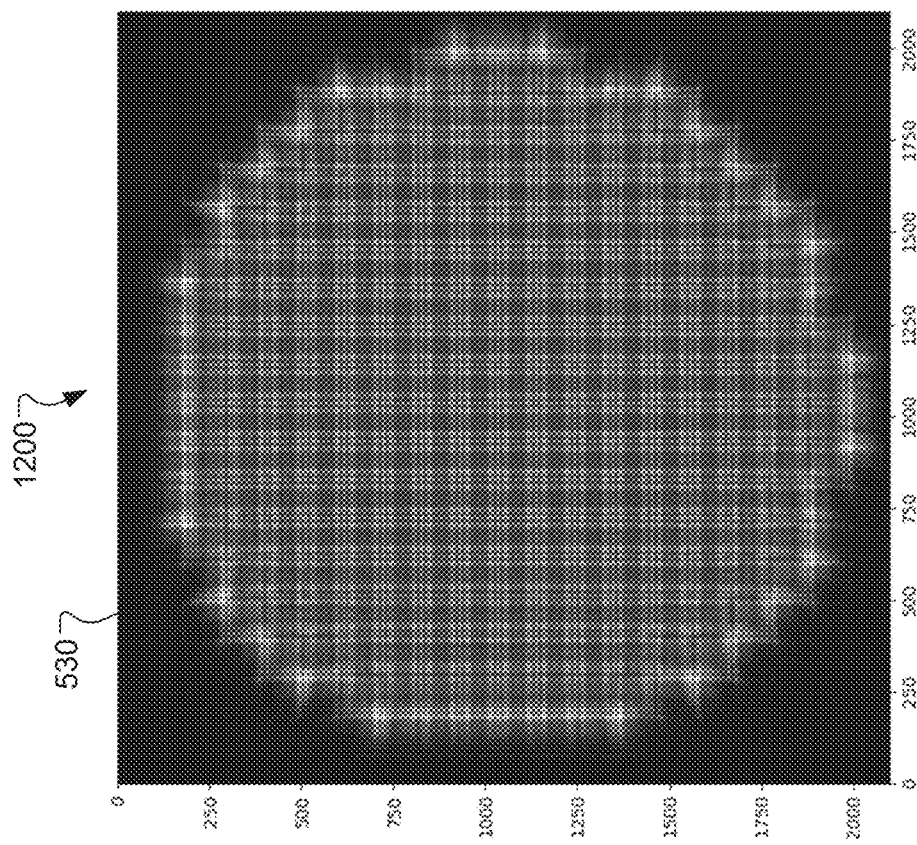
FIG. 12B is a picture of a diffraction pattern of light collimated by a collimator at 10 mm from the collimator, according to an embodiment.
Figure 12A:
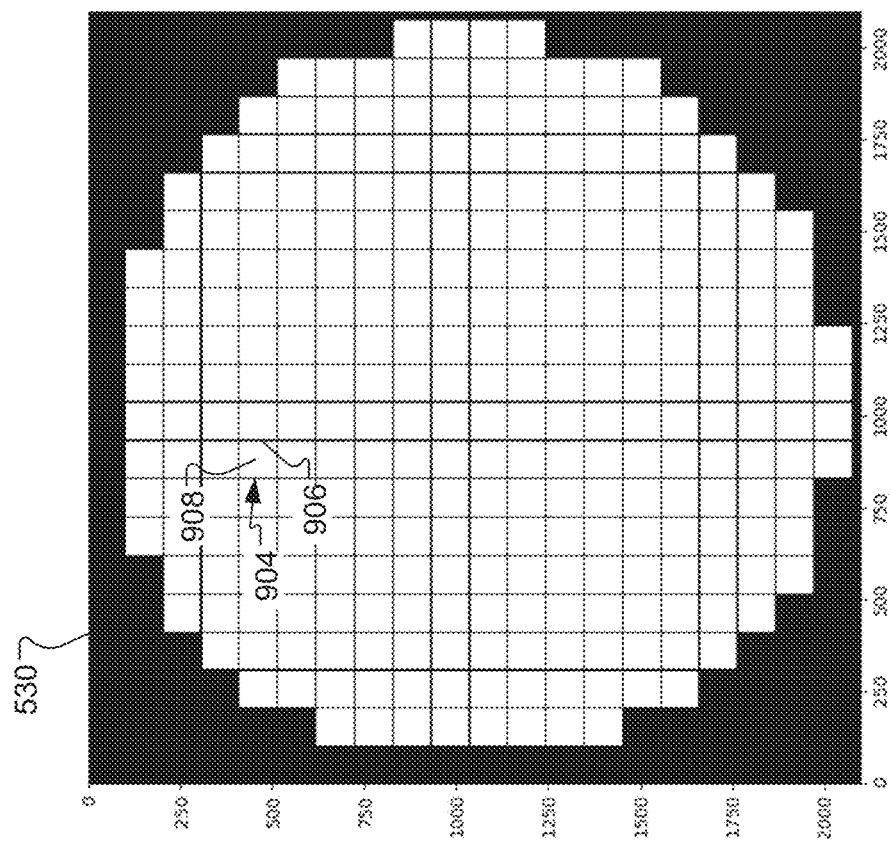
FIG. 12A is a top-side picture of the collimator showing the wall and the through-channel of the microtube, according to an embodiment.

FIG. 12A is a top-side picture of the collimator 530 showing the wall 906 and the through-channel 908 of the microtube 904, according to an embodiment. Some of the features in FIG. 12A are the same as or similar to some of the features in FIGS. 1-11C as noted by same reference numbers, unless expressly described otherwise. The collimator 530 may include a plurality of the microtube 904. The wall 906 of the microtube 904 may have a thickness ranging from 3 microns to 5 microns. In an embodiment, the wall 906 may have a thickness of 4 microns. The through-channel 908 of the microtube 904 may have a width ranging from 90 microns to 110 microns. In an embodiment, the through-channel 908 may have a width of 100 microns.

FIG. 12B is a picture of a diffraction pattern 1200 of light collimated by the collimator 530 at 10 mm from the collimator 530, according to an embodiment. Some of the features in FIG. 12B are the same as or similar to some of the features in FIGS. 1-12A as noted by same reference numbers, unless expressly described otherwise. As the light passes from one of the plurality of the microtubes 904, a wave pattern of the light may spread spatially to a region adjacent to an opening of a neighboring microtube 904. As a width of the through-channel decreases relative to a wavelength of the light passing through the through-channel 908, diffraction of the light as it leaves the through-channel 908 may affect an intensity of the light measured at the optical sensor. Diffraction may, in some embodiments, result in a significant amount of the intensity of the light being diffracted to an area outside a region directly beneath the collimator 530. However, in some embodiments, the through-channel width may be tuned to maximize collimation and minimize diffraction. In various embodiments the tuning may relate to the aspect ratio of the microtube 904 and/or the wavelengths of light being collimated. A higher aspect ratio may result in better collimation, whereas a larger through-channel width 908 may minimize diffraction. In one embodiment, for a through-channel width of 100 microns, diffraction of 700 nm-wavelength light may result in over 95% of the intensity of the light falling beneath the collimator 530.

Figure 13:
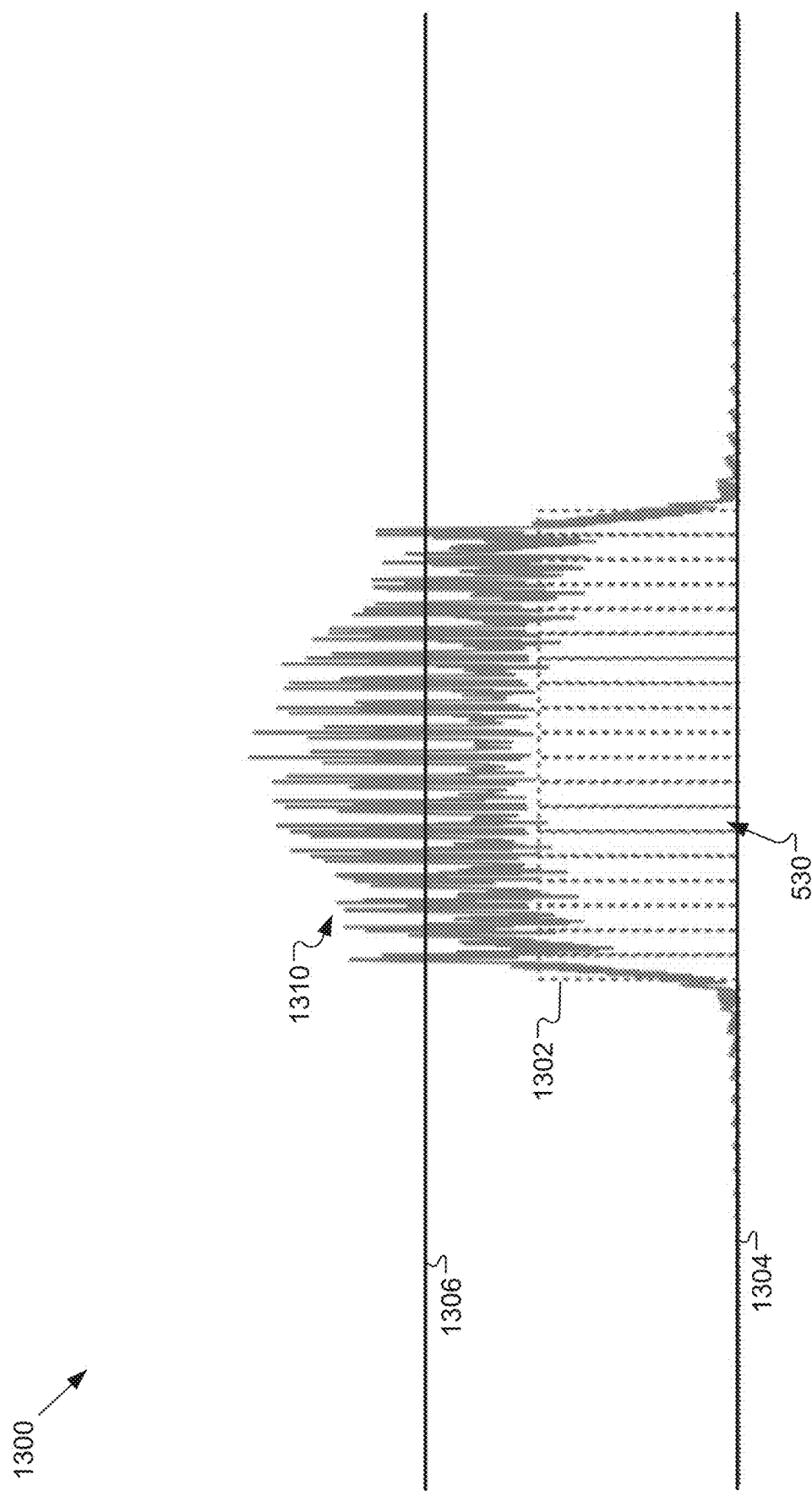
FIG. 13 shows a graph 1300 illustrating an intensity profile of the diffraction pattern 1200 illustrated in FIG. 12B

FIG. 13 shows a graph 1300 illustrating an intensity profile of the diffraction pattern 1200 illustrated in FIG. 12B. Some of the features in FIG. 13 are the same as or similar to some of the features in FIGS. 1-12B as noted by same reference numbers, unless expressly described otherwise. The dashed lines 1302 may illustrate positions of through-channels of the collimator 530. The collimator 530 may have a through-channel width of 100 microns. At line 1304 the intensity of the light is null, and at line 1306 the intensity of the light is 100% of the intensity of the light as the light passes out of the collimator 530. Peaks and valleys of a curve 1310 indicate higher intensity and lower intensity, respectively, at a corresponding location beneath the collimator 530. Accordingly, some areas have greater intensity than the intensity of the light as it passed out of the collimator 530, whereas other areas have less intensity than the intensity of the light as it passed from the collimator 530. A sum of the intensities at each point under the collimator 530 may be, in an embodiment, approximately 95% of the intensity of the light is it passed from the collimator 530. The curve 1310 indicates that, in an embodiment, diffraction does not result in significant attenuation of the light beneath the collimator for a 100 micron through-channel width.

Figure 14A:
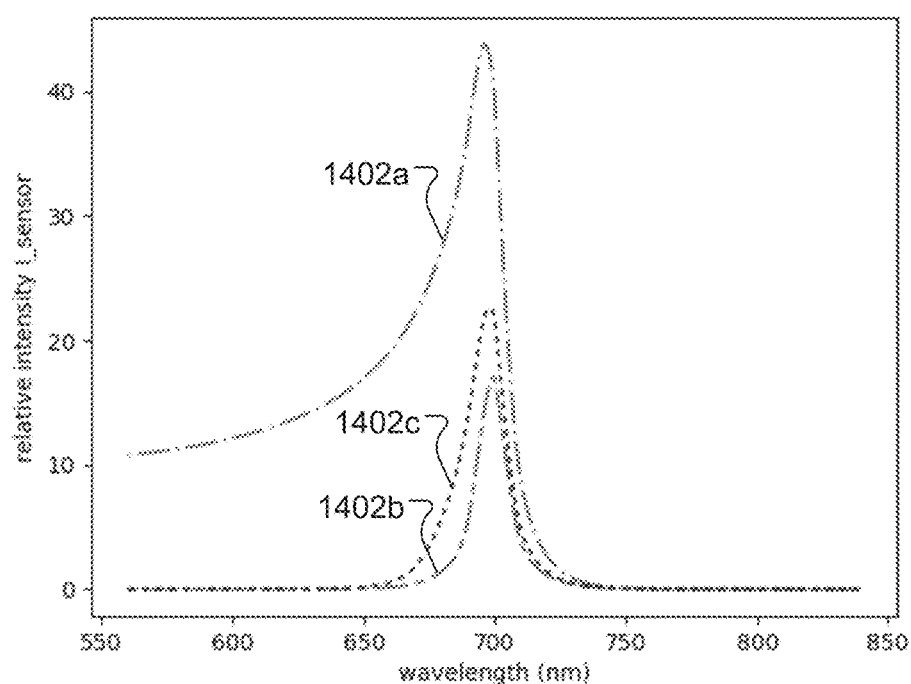
FIG. 14A shows a graph illustrating transmission curves corresponding to various refractive indices for collimated and uncollimated light, according to an embodiment.

FIG. 14A shows a graph 1402 illustrating transmission curves 1402a-c corresponding to various refractive indices for collimated and uncollimated light, according to an embodiment. Some of the features in FIG. 14A are the same as or similar to some of the features in FIGS. 1-13 as noted by same reference numbers, unless expressly described otherwise. The transmission curves 1402a-c may correspond to broadband light having wavelengths ranging from 560 nm to 840 nm passed through a filter, such as the filter 528. The filter may be a bandpass filter, such as a Fabry-Perot etalon filter. The filter may be a 700 nm bandpass filter. The broadband light may be incident on a collimator at various angles $\theta_{incident}$ ranging from −60 degrees (°) from normal to 60° from normal. The collimator may, for example, include the collimator 530 described and illustrated regarding other FIGs. herein.

In an embodiment, the transmission curves 1402a-c may be modeled according to a numerical relationship $I_{filter}$ between an effective wavelength $\lambda_{eff}$ of light passing through the filter and a wavelength $\lambda_0$ of peak transmission through the filter. The $I_{filter}$ may be modeled as $$I_{filter} = 0.6 \exp\left(-\frac{|\lambda_{eff} - \lambda_0|}{2(0.003\lambda_0)^2}\right) + 0.3\exp\left(-\frac{|\lambda_{eff} - \lambda_0|}{2(0.02\lambda_0)^2}\right).$$

In an embodiment, $\lambda_{eff}$ may be an effective wavelength of light passing through the filter based on the angle $\theta_{incident}$ at which the light is incident on the collimator. For example, the filter may be a Fabry-Perot filter. The mechanism of the filter may be destructive interference. A first wave that may experience a same and/or similar phase transition as a second wave may have a similar attenuation by the filter as the second wave. Accordingly, the $\lambda_{eff}$ may be modeled as $$\lambda_{eff} = \frac{\lambda_{incident}}{\cos\left(\arcsin\left(\frac{\sin\theta_{incident}}{n_{filter}}\right)\right)},$$

where $\lambda_{incident}$ may be a wavelength of the light incident on the filter. As the angle $\theta_{incident}$ increases, $\lambda_{eff}$ may decrease so that a longer wavelength may be filtered by the filter as if the wavelength were shorter.

For example, the filter may have a passband with a 700 nm peak and a FWHM band ranging from 675 nm to 725 nm for broadband light striking the filter at a normal $\theta_{incident}$. A shape of a curve modeling the passband for normally-incident broadband light may be symmetric about the peak. However, for non-normally-incident broadband light, a shape of the curve such as the transmission curve 1402a may be asymmetric about a peak of the transmission curve 1402a. The asymmetry may be due to an increase in an apparent intensity of lower-wavelength light due to the effects on non-normal incidence. The apparent intensity may be an intensity of the wavelength after the light passes through the filter and may be different than an intensity of the wavelength before the light passes through the filter. Accordingly, wavelengths larger than the peak-transmission wavelength may have a lower apparent intensity. The peak-transmission wavelength may have a lower apparent intensity. A wavelength shorter than the peak-transmission wavelength may appear to be the peak-transmission wavelength. The peak-transmission wavelength may have a higher apparent intensity. Wavelengths smaller than the peak-transmission wavelength may have a higher apparent intensity. For example, a FWHM band of the transmission curve 1402a may range from 665 nm to 705 nm, and the apparent peak-transmission wavelength of the transmission curve 1402a may be 695 nm.

The asymmetry and/or shift of the transmission curve 1402a for non-normally-incident light may indicate that the filter may transmit a higher total intensity of light than an intensity of the light that corresponds to the filter passband. This may cause a sensor, such as the optical sensor 532, communicate an incorrect intensity of the light to a processing device, which may in turn incorrectly interpret the communicated intensity. For example, the processing device may interpret the communicated intensity to correspond to an incorrect physiological condition, physiological parameter, and/or physiological constituent. In various embodiments, the processing device may compensate for the asymmetry and/or shift of the transmission curve 1402a. For example, the processing device may store information regarding the intensity and/or a spectral profile of the light before the light passes through the filter. The processing device may, based on the intensity and/or spectral profile of the light before the light passes through the filter, adjust an intensity communicated to the processing device by the optical sensor. However, in various embodiments, it may be impractical, inconvenient, and/or unlikely to have information regarding the light before the light passes through the filter, such as when the light passes through another material and an intensity of at least one wavelength of the light is attenuated. For example, the light may pass through a tissue of a body part before passing through the filter.

In an embodiment, the collimator may reduce and/or eliminate the asymmetry and/or shift of the transmission curve 1402a, as may be illustrated by the transmission curve 1402b and/or the transmission curve 1402c. The transmission curve 1402b may correspond to collimated light, where the collimator includes a filler, such as the filler 802, having a refractive index $n_{filler}$ equal to 1. The transmission curve 1402b may correspond to collimated light, where the collimator includes the filler having a refractive index $n_{filler}$ equal to 2. A wall of the collimator, such as the wall 906, may have a height, such as the height 906a, equal to 250 microns, and/or may have a thickness, such as the thickness 906b, equal to 5 microns. A through-channel formed by the wall, such as the through-channel 908, may have a width, such as the width 908a, equal to 50 microns.

A difference between the transmission curve 1402b and the transmission curve 1402c may correspond to a difference between $n_{filler}$ for the transmission curve 1402b and $n_{filler}$ for the transmission curve 1402c. As $n_{filler}$ increases, a percentage of the light reflected at surfaces of the filler (i.e. at interfaces between the collimator and the filter, the optical sensor, open air, a surface against which the collimator is placed, and so forth) also increases. Conversely, as $n_{filler}$ increases, $\theta_{filler}$ for non-normal light may decrease. The decreasing $\theta_{filler}$ may have an effect similar to widening the microtube through-channel. Because $\theta_{filler}$ decreases, less light may be reflected and/or absorbed by the microtube walls, and more light may be transmitted through the through-channel. The difference between the transmission curve 1402b and the transmission curve 1402c may indicate that the effect of the decreasing $\theta_{filler}$ may weigh more heavily in the difference than the effect of the increasing reflection. Accordingly, as $n_{filler}$ increases, the collimator may transmit more light. In various embodiments, $n_{filler}$ may range from 1.3 to 1.7.

The collimator may limit the angle $\theta_{incident}$ to a smaller range of angles, which may in turn limit a maximum path length of light transmitted through the filter. The collimator may reduce an average of the path lengths of the light transmitted through the filter by absorbing and/or reflecting away from the filter and/or the optical sensor light rays having an angle $\theta_{incident}$ larger than an arctangent of a ratio of the wall height to the through-channel width. The reduced range of the angle $\theta_{incident}$ may narrow a range of the effective wavelengths $\lambda_{eff}$. The reduced range of $\lambda_{eff}$ may narrow the transmission curve and/or may render the transmission curve more symmetrical compared to the transmission curve 1402a, as may be illustrated by the transmission curve 1402b and the transmission curve 1402c.

In various embodiments, the filter, the collimator, and/or the optical sensor may be integrated into a miniaturized spectrometer. Factors such as shadowing, an amount of light transmitted through the filter, and/or reflection of light at layer interfaces may affect an intensity of the light detected by the optical sensor $I_{sensor}$. Additionally, various layers and/or materials of the collimator and/or the filter may absorb some energy of the light as the light is transmitted through the collimator and/or the filter. Accordingly, $I_{sensor}$ may be modeled as a product of $I_{filter}$, $I_{normal}$, $I_{shadow}$, and/or $I_{trans}$.

Factors such as $I_{filter}$, $I_{normal}$, $I_{shadow}$, and/or $I_{trans}$ may be stored to be accessible by the processing device, and the processing device may use the factors in processing light intensities communicated by the optical sensor to the processing device. For example, a broadband light source may emit the light towards a body part of a user of a wearable device, such as the wearable device 100. The light may pass into the body part. Various wavelengths of the light may be reflected, refracted, and/or absorbed by one or more constituents of the body part. Features of light leaving the body part, such as the intensity and/or the spectral profile of the light, may correspond to one or more physiological conditions, physiological parameters, and/or physiological constituents of the user. The light may pass from the body part to the miniaturized spectrometer. The collimator may collimate the light. The filter may filter the light. The optical sensor may generate a signal corresponding to an intensity of the collimated and/or filtered light impinging on the optical sensor. The signal may be transmitted to the processing device. The processing device may determine an intensity of the light impinging on the optical sensor based on the signal. The processing device may determine a spectral profile of the light impinging on the optical sensor based on the signal.

The processing device may access information about the light emitted from the light source, such as the intensity and/or spectral profile of the light. For example, the information may be communicated from the light source to the processing device, and/or the information may be stored on a memory device electronically coupled to the processing device. The processing device may calculate a maximum possible intensity of the light impinging on the optical sensor based on $I_{sensor}$ and/or the intensity of the light emitted from the light source. The processing device may compare the intensity and/or the spectral profile of the light impinging on the optical sensor to the maximum possible intensity of the light, the intensity of the light emitted from the light source, and/or the spectral profile of the light emitted from the light source. Based on the comparison, the processing device may determine a physiological condition, physiological parameter, and/or a physiological constituent of the user.

Figure 14B:
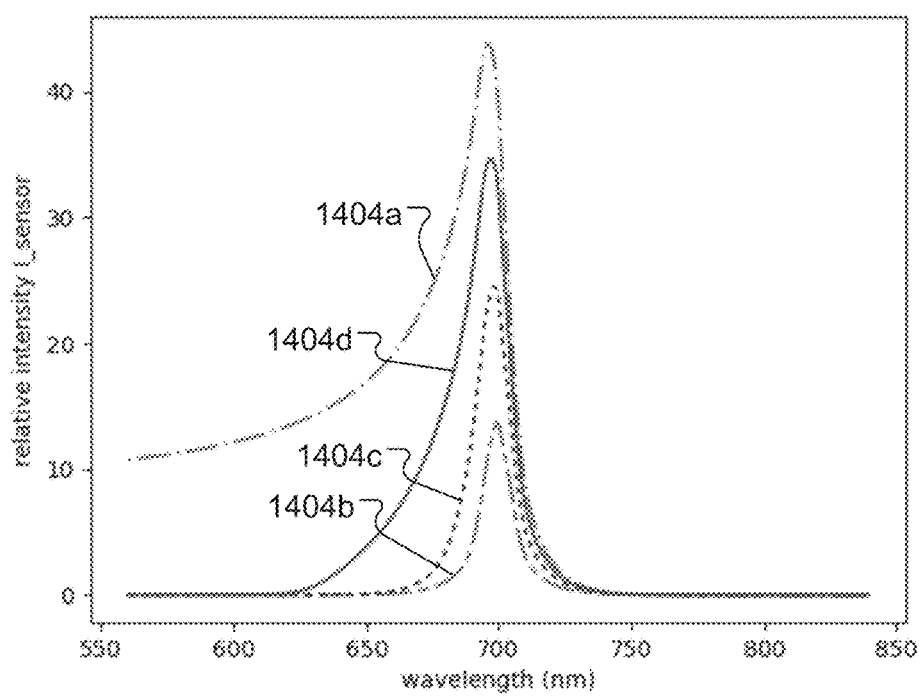
FIG. 14B shows a graph illustrating transmission curves corresponding to various through-channel widths for collimated light, according to an embodiment.

FIG. 14B shows a graph 1404 illustrating transmission curves 1404a-d corresponding to various through-channel widths for collimated and uncollimated light, according to an embodiment. Some of the features in FIG. 14B are the same as or similar to some of the features in FIGS. 1-14A as noted by same reference numbers, unless expressly described otherwise. The transmission curves 1404a-d may correspond to broadband light having wavelengths ranging from 560 nm to 840 nm passed through a filter. In an embodiment, the filter may be the filter 528 described and illustrated herein. The filter may be a bandpass filter. For example, the filter may be a Fabry-Perot etalon filter. The filter may be a 700 nm bandpass filter. The broadband light may be incident on a collimator at various angles $\theta_{incident}$ ranging from −60 degrees (°) from normal to 60° from normal. In an embodiment, the collimator may be the collimator 530 described and illustrated herein.

The transmission curve 1404a may correspond to uncollimated light. The transmission curves 1404b-d may correspond to collimated light. The collimator may include a wall, such as the wall 906, having a height, such as the height 906b, equal to 250 microns. A thickness of the wall, such as the thickness 906a, may be equal to 5 microns. The wall may form a microtube, such as the microtube, having a through-channel, such as the through-channel 908a. The through-channel may be filled with a filler, such as the filler 802. The filler may have an index of refraction $n_{filler}$ equal to 1. The through-channel may have a width, such as the width 908a. The transmission curve 1404b may correspond to a width of the through-channel equal to 40 microns. The transmission curve 1404c may correspond to a width of the through-channel equal to 80 microns. The transmission curve 1404d may correspond to a width of the through-channel equal to 180 microns.

In an embodiment, an aspect ratio of the microtube and/or the collimator may be a ratio of the wall height to the through-channel width. The aspect ratio may correspond to a range of incident angles $\theta_{incident}$ for light that may be transmitted through the collimator. In an embodiment, increasing the aspect ratio of the microtube and/or the collimator may narrow a range of angles $\theta_{incident}$ for which light incident on the collimator may pass through the microtube and/or the collimator. In an embodiment, increasing the aspect ratio of the microtube and/or the collimator may narrow a FWHM band of a transmission curve corresponding to light passing through the collimator and/or microtube. In an embodiment, increasing the aspect ratio of the microtube and/or the collimator may reduce $I_{shadow}$. In another embodiment, decreasing the aspect ratio of the microtube and/or the collimator may broaden the range of angles $\theta_{incident}$ for which light incident on the collimator may pass through the microtube and/or the collimator, and/or may broaden the FWHM band of the transmission curve. However, above a threshold aspect ratio, the transmission curve may become asymmetric similar to the transmission curve 1404a for uncollimated light. The threshold aspect ratio may range from 1 to 10, from 1 to 8 from 2 to 5, and/or from 3 to 4. In one embodiment, the threshold aspect ratio may be 3.125.

In an embodiment, the transmission curve 1404b may have an aspect ratio of 6.250. The transmission curve 1404b may be symmetric about its peak. In an embodiment, the transmission curve 1404c may have an aspect ratio of 3.125. The transmission curve 1404c may be symmetric about its peak. In an embodiment, the transmission curve 1404d may have an aspect ratio of 1.389. The transmission curve 1404d may be asymmetric about its peak. As may be illustrated by a comparison of the transmission curves 1404b-d with the transmission curves 1402b-c, variation of the transmission curves may be more significant as the aspect ratio is varied than as the refractive index $n_{filler}$ is varied.

The transmission curves 1402a-c described and illustrated regarding FIG. 14A and the transmission curves 1404a-d described and illustrated regarding FIG. 14B may illustrate how the collimator may enable measurement by a miniaturized spectrometer. A conventional spectrometer may include a lens and/or mirrors to collimate light. Accordingly, a conventional spectrometer may be too bulky to incorporate into a wearable device. The collimator described herein may allow for compact enough construction of the miniaturized spectrometer to integrate into the wearable device, and more particularly into the band of the wearable device, where space may be more limited than in, for example, a watch head of the wearable device. The transmission curve 1402a and the transmission curve 1404a may illustrate that a miniaturized spectrometer operating without the collimator may have skewed measurements, lower resolution measurements, and/or otherwise incorrect measurements. The transmission curves 1402b-c and the transmission curves 1404b-d may illustrate that a miniaturized spectrometer operating with the collimator may more accurately measure relative wavelength intensities than the miniaturized spectrometer operating without the collimator.

The transmission curves 1402b-c and the transmission curves 140b-d may further demonstrate that dimensions of the collimator may be tuned for a particular application. For example, in one application, high resolution may be preferred over high sensitivity. Accordingly, dimensions producing the transmission curve 1402b and/or the transmission curve 1404b may be preferred over other dimensions. In another application, high sensitivity may be preferred over high resolution. Accordingly, dimensions producing the transmission curve 1402c and/or the transmission curve 1404d may be preferred over other dimensions. In yet another application, a balance between resolution and sensitivity may be optimized. Accordingly, dimensions producing the transmission curve 1404c may be preferred over other dimensions.

Figure 15A:
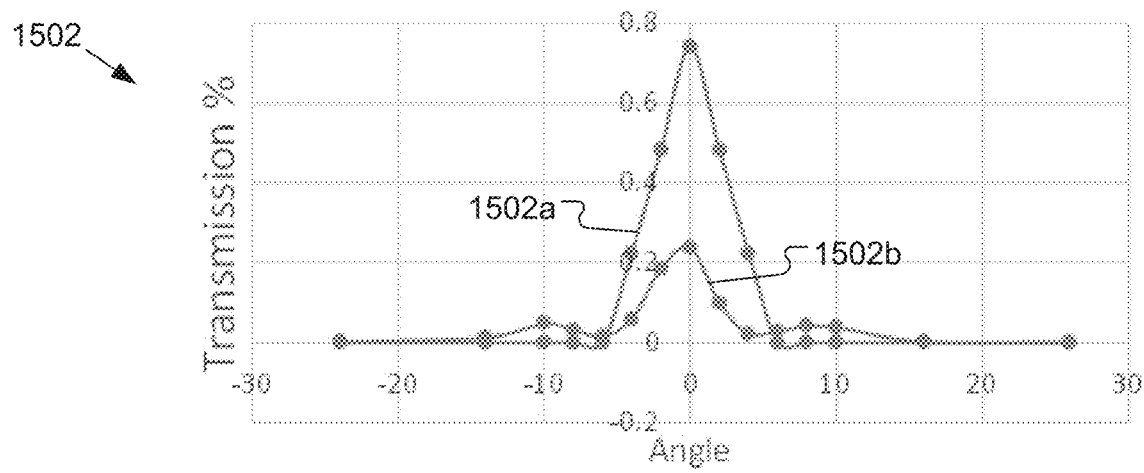
FIG. 15A is a graph illustrating a transmission efficiency of a microtube having a wall with a 250 micrometer (micron) height and a through-channel with a 25-micron width, according to an embodiment.

FIG. 15A is a graph 1502 illustrating a transmission efficiency of a microtube having a wall with a 250 micron height and a through-channel with a 25 micron width, according to an embodiment. Some of the features in FIG. 15A are the same as or similar to some of the features in FIGS. 1-14B as noted by same reference numbers, unless expressly described otherwise. The graph plots transmission percentage of light for a range of angels from −30° to 30°. The graph includes a model-generated curve 1502a and an experimentally generated curve 1502b. The model-generated curve 1502a may have been generated using the model for $I_{sensor}$ described herein. The experimentally generated curve 1504b may include direct measurements taken using embodiments of a light source such as the light source 602, a collimator such as the collimator 530, a filter such as the filter 528, and/or an optical sensor such as the optical sensor 532. The light source 602 may include a tungsten filament bulb. The fliter 528 may include a monochromator selectively set to 1550 nm.

The model-generated curve 1502a may have a peak transmission efficiency ranging from 70 percent to 80 percent for zero-degree incidence. In one embodiment, the model-generated curve 1502a may have a peak transmission efficiency of 74.3% The model-generated curve 1502a may have non-zero transmission ranging from −6° to 6° and may be symmetrical about the peak transmission efficiency. In one embodiment, the model-generated curve 1502a may have non-zero transmission ranging from −5.71° to 5.71°. The experimentally generated curve 1502b may have a global peak transmission efficiency ranging from 20 percent to 30 percent for zero-degree incidence and two local peaks for non-zero-degree incidence. In one embodiment, the experimentally generated curve 1502b may have a global peak transmission efficiency of 23.8 percent. The non-zero-degree incidence local peaks may correspond to diffraction effects of the collimator. The experimentally generated curve 1502b may have a non-zero transmission ranging from −6° to 6° and/or from −4° to 4°. In one embodiment, the experimentally generated curve 1502b may have a non-zero transmission ranging from −5.58° to 4.22°.

Figure 15B:
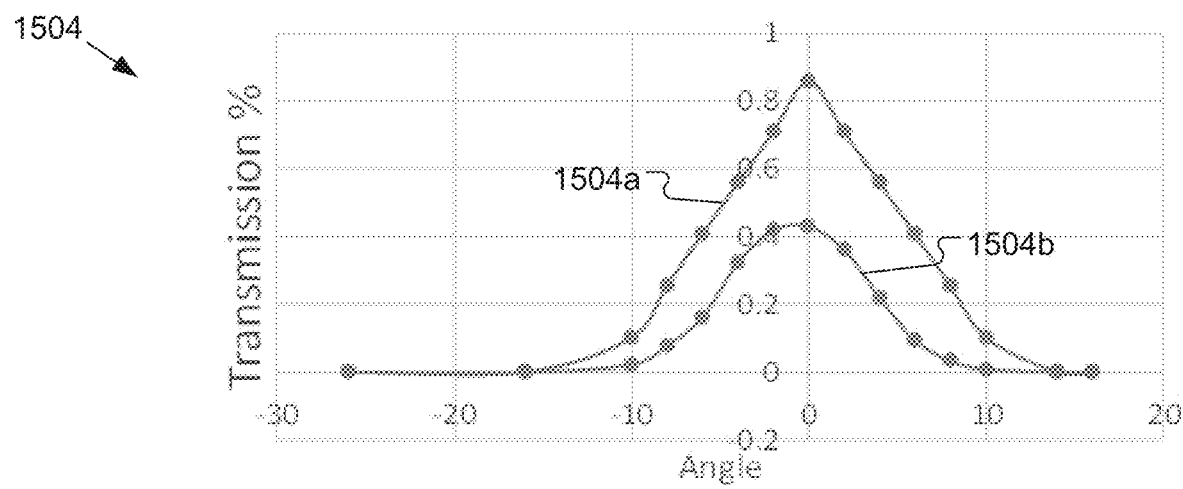
FIG. 15B is a graph illustrating a transmission efficiency of a microtube having a wall with a 250-micron height and a through-channel with a 50 micron width, according to an embodiment.

FIG. 15B is a graph 1504 illustrating a transmission efficiency of a microtube having a wall with a 250 micron height and a through-channel with a 50 micron width, according to an embodiment. Some of the features in FIG. 15B are the same as or similar to some of the features in FIGS. 1-15A as noted by same reference numbers, unless expressly described otherwise. The graph includes a model-generated curve 1504a and an experimentally generated curve 1504b. The model-generated curve 1504a may have been generated using the model for $I_{sensor}$ described herein. The experimentally generated curve 1504b may include direct measurements taken using embodiments of a light source such as the light source 602, a collimator such as the collimator 530, a filter such as the filter 528, and/or an optical sensor such as the optical sensor 532. The model-generated curve 1504a may have a peak transmission efficiency ranging from 80 percent to 90 percent for zero-degree incidence. In one embodiment, the model-generated curve 1504*a* may have a peak transmission efficiency of 85.7 percent. The model-generated curve 1504*a* may have non-zero transmission ranging from −15° to 15° and may be symmetrical about the peak transmission efficiency. In one embodiment, the model-generated curve 1504*a* may have a non-zero transmission ranging from −11.3° to 11.3°. The experimentally generated curve 1504*b* may have a global peak transmission efficiency ranging from 40 percent to 45 percent for zero-degree incidence with no local peaks. In one embodiment, the experimentally generated curve 1504*b* may have a global peak transmission efficiency of 42.9 percent. The experimentally generated curve 1504*b* may have a non-zero transmission ranging from −16° to 16° and/or from −10° to 10°. In one embodiment, the experimentally generated curve 1504*b* may have a non-zero transmission ranging from −10.2° to 9.16°.

Figure 15C:
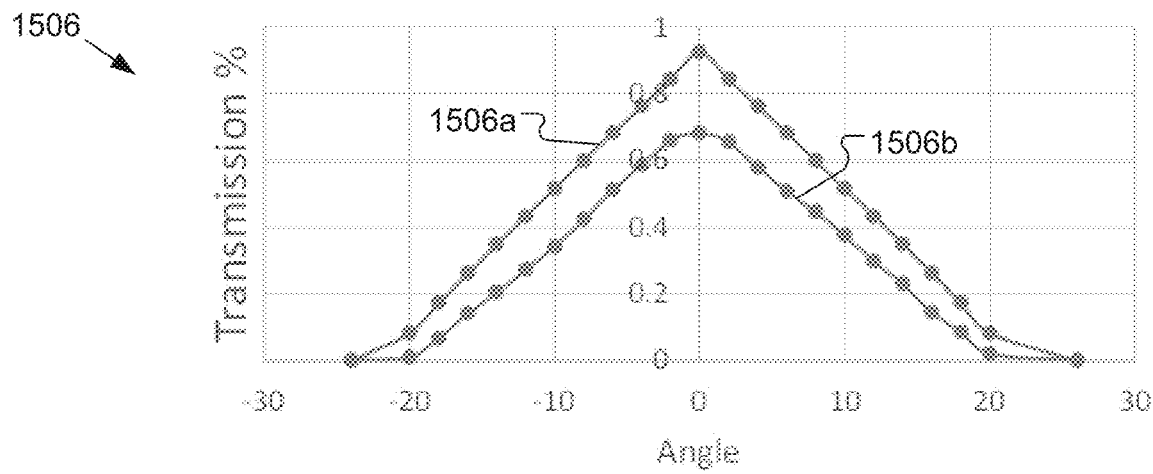
FIG. 15C is a graph illustrating a transmission efficiency of a microtube having a wall with a 250-micron height and a through-channel with a 100 micron width, according to an embodiment.

FIG. 15C is a graph 1506 illustrating a transmission efficiency of a microtube having a wall with a 250 micron height and a through-channel with a 100 micron width, according to an embodiment. Some of the features in FIG. 15C are the same as or similar to some of the features in FIGS. 1-15B as noted by same reference numbers, unless expressly described otherwise. The graph includes a model-generated curve 1506*a* and an experimentally generated curve 1506*b*. The model-generated curve 1506*a* may have been generated using the model for $I_{sensor}$ described herein. The experimentally generated curve 1506*b* may include direct measurements taken using embodiments of a light source such as the light source 602, a collimator such as the collimator 530, a filter such as the filter 528, and/or an optical sensor such as the optical sensor 532. The model-generated curve 1506*a* may have a peak transmission efficiency ranging from 90 percent to 95 percent for zero-degree incidence. In one embodiment, the model-generated curve 1506*a* may have a peak transmission of 92.5 percent. The model-generated curve 1506*a* may have non-zero transmission ranging from −25° to 25° and may be symmetrical about the peak transmission efficiency. In one embodiment, the model-generated curve 1506*a* may have a non-zero transmission ranging from −21.8° to 21.8°. The experimentally generated curve 1506*b* may have a global peak transmission efficiency ranging from 65 percent to 70 percent for zero-degree incidence with no local peaks. In one embodiment, the experimentally generated curve 1506*b* may have a global peak transmission efficiency of 68.2 percent. The experimentally generated curve 1506*b* may have a non-zero transmission ranging from −20° to 20° and/or −24° to 24°. In one embodiment, the experimentally generated curve 1506*b* may have a non-zero transmission ranging from −20° to 20.6°.

A comparison of the graphs 1502, 1504, and/or 1506 may show the model-generated curves match the experimentally generated curves better for wider through-channels. Accordingly, changing the through-channel width may have a different experimental relationship with angle of incidence and/or transmission efficiency than the modeled relationship. Additionally, the graphs 1502, 1504, and/or 1506 show close correlation between model and experiment where transmission reaches 0 percent, which demonstrates the collimator is highly absorptive at the wavelength of interest. Furthermore, a comparison of the difference between the experimental results and the modeled results as microtube with increases shows that diffraction effects play a larger role for smaller microtube widths than for larger microtube widths. The modeled curves 1502*a*, 1504*a*, and 1506*a* do not include diffraction effects as part of the model calculation. However, the experimental curves 1502*b*, 1504*b*, and 1506*b* include reduction in transmission efficiency due to diffraction. Notably, diffraction may play a significantly larger role in reducing transmission efficiency for microtube widths less than 100 microns.

The above description sets forth numerous specific details such as examples of specific systems, components, methods and so forth, in order to provide a good understanding of several implementations. It will be apparent to one skilled in the art, however, that at least some implementations may be practiced without these specific details. In other instances, well-known components or methods are not described in detail or are presented in simple block diagram format in order to avoid unnecessarily obscuring the present implementations. Thus, the specific details set forth above are merely exemplary. Particular implementations may vary from these exemplary details and still be contemplated to be within the scope of the present implementations.

It is to be understood that the above description is intended to be illustrative and not restrictive. Many other implementations will be apparent to those of skill in the art upon reading and understanding the above description. The scope of the present implementations should, therefore, be determined with reference to the appended claims, along with the full scope of equivalents to which such claims are entitled.

The disclosure above encompasses multiple distinct embodiments with independent utility. While these embodiments have been disclosed in a particular form, the specific embodiments disclosed and illustrated above are not to be considered in a limiting sense as numerous variations are possible. The subject matter of the embodiments includes the novel and non-obvious combinations and sub-combinations of the various elements, features, functions and/or properties disclosed above and inherent to those skilled in the art pertaining to such embodiments. Where the disclosure or subsequently filed claims recite "a" element, "a first" element, or any such equivalent term, the disclosure or claims is to be understood to incorporate one or more such elements, neither requiring nor excluding two or more such elements.

Applicant(s) reserves the right to submit claims directed to combinations and sub-combinations of the disclosed embodiments that are believed to be novel and non-obvious. Embodiments embodied in other combinations and sub-combinations of features, functions, elements and/or properties may be claimed through amendment of those claims or presentation of new claims in the present application or in a related application. Such amended or new claims, whether they are directed to the same embodiment or a different embodiment and whether they are different, broader, narrower or equal in scope to the original claims, are to be considered within the subject matter of the embodiments described herein.

The invention claimed is:
1. A collimator, comprising:
a first carbon nanotube structure comprising a first microtube that includes a first set of aligned carbon nanotubes infiltrated by carbon and a first through-channel, the first carbon nanotube structure having a height to through-channel width aspect ratio between 3:1 to 10:1, wherein:
the first set of aligned carbon nanotubes infiltrated by carbon is configured to absorb a first portion of light that travels through the first through-channel at a first angle and impinges a side of a first through-channel portion;

the first set of aligned carbon nanotubes infiltrated by the carbon is configured to allow a second portion of the light that enters the first through-channel at a second angle to pass through from a top of the first through-channel to a bottom of the first through-channel, wherein the first carbon nanotube structure comprises:

a first wall comprising a first subset of carbon nanotubes infiltrated with carbon; and a second wall comprising a second subset of carbon nanotubes infiltrated with carbon, wherein a thickness of the first wall is different than a thickness of the second wall;

a second carbon nanotube structure comprising a second microtube that includes a second set of aligned carbon nanotubes infiltrated by carbon and a second through-channel, the second carbon nanotube structure having a height to through-channel width aspect ratio between 3:1 to 10:1, wherein:

the second set of aligned carbon nanotubes infiltrated by carbon is configured to absorb a third portion of the light that travels through the second through-channel at a third angle and impinges a side of a second through-channel portion;

the second set of aligned carbon nanotubes infiltrated by the carbon is configured to allow a fourth portion of the light that enters the second through-channel at a fourth angle to pass through from a top of the second through-channel to a bottom of the second through-channel; and the first microtube and the second microtube share a common structural portion to form an array of microtubes; and a filler disposed within the first through-channel or the second through-channel, wherein:

the filler fills the first through-channel from a bottom of the first through-channel or the second through-channel to a top of the first through-channel or the second through-channel such that the filler is flush with a bottom surface of the first through-channel or the second through-channel and a top surface of the first through-channel or the second through-channel; and the filler is a transparent material to allow light to be transmitted through the first through-channel or the second through-channel without interfering with the light.

2. The collimator of claim 1, wherein the first angle, the second angle, the third angle, or the fourth angle of the light is relative to a plane extending along the bottom surface of the collimator.

3. The collimator of claim 1, wherein:

the first angle or the second angle correlates directly with the first carbon nanotube structure aspect ratio; or the third angle or the fourth angle correlates directly with the second carbon nanotube structure aspect ratio.

4. The collimator of claim 1, wherein:

the first angle or the third angle ranges up to 85 degrees, up to 80 degrees, up to 75 degrees, up to 70 degrees, or up to 60 degrees; or the second angle or the fourth angle ranges from 85 degrees to 90 degrees, from 80 degrees to 90 degrees, from 75 degrees to 90 degrees, from 70 degrees to 90 degrees, or from 60 degrees to 90 degrees.

5. The collimator of claim 1, wherein a degree of the first angle or the second angle is based a distance a ray of the first portion of light is from a wall of a first carbon nanotube structure.

6. The collimator of claim 1, wherein:

the first wall comprises a first subset of carbon nanotubes infiltrated with carbon, and a second wall comprises a second subset of carbon nanotubes infiltrated with carbon; and the first carbon nanotube structure further comprises:

a third wall comprising a third subset of carbon nanotubes infiltrated with carbon; and a fourth wall comprising a fourth subset of carbon nanotubes infiltrated with carbon.

7. The collimator of claim 1, the collimator has a length between 5 mm and 9 mm and a width between 0.5 mm and 2 mm.

8. The collimator of claim 1, wherein the array of microtubes includes a plurality of microtubes, including the first microtube and the second microtube, that share common structural portions to form a square or rectangular array of microtubes.

9. The collimator of claim 1, wherein the first carbon nanotube structure comprises a cylindrical wall of the first set of aligned carbon nanotubes forming a cylindrical microtube.

10. The collimator of claim 1, wherein the carbon nanotube structure comprises carbon nanotube material to absorb the first portion of the light with an average reflectance of less than or equal to 10 percent.

11. A collimator, comprising:

a carbon nanotube structure comprising a microtube that includes a set of aligned carbon nanotubes infiltrated by carbon and a through-channel, wherein:

the set of aligned carbon nanotubes infiltrated by carbon is configured to absorb a first portion of light that travels through the through-channel at a first angle and impinges a side of a through-channel portion, wherein the set of aligned carbon nanotubes defines a plurality of microtubes, wherein the plurality of microtubes are arranged in an array and includes a plurality of shapes or sizes of the microtubes; and the set of aligned carbon nanotubes infiltrated by the carbon is configured to allow a second portion of the light that enters the through-channel at a second angle to pass through from a top of the through-channel to a bottom of the through-channel;

a filler disposed within the through-channel, wherein:

the filler fills the through-channel from a bottom of the through-channel to a top of the through-channel such that the filler is flush with a bottom surface of the through-channel and a top surface of the through-channel; and the filler is a transparent material to allow light to be transmitted through the through-channel without interfering with the light.

12. The collimator of claim 11, wherein:

the filler is a polymer with a relatively low viscosity such that a resin of the polymer is depositable in the through-channel without damaging the microtube; and the filler reinforces the microtube to increase a rigidity of the carbon nanotube structure.

13. The collimator of claim 11, wherein the filler has an index of refraction ranging from 1.3 to 1.9 based on a wavelength of light traveling through the through-channel.

14. The collimator of claim 11, wherein the set of aligned carbon nanotubes infiltrated by carbon forms a wall structure with a thickness ranging from 1 micron to 50 microns and a height ranging from 50 microns to 1000 microns.

15. The collimator of claim 11, wherein the infiltration of the carbon into the set of aligned carbon nanotubes creates a roughness along a surface of the microtube, wherein: the roughness is defined by lengthwise shape of the surface of the microtube; and the surface roughness of the microtube reduces a reflectivity of the surface of the microtube.

16. A collimator, comprising:
a carbon nanotube structure comprising a microtube that includes a set of aligned carbon nanotubes infiltrated by carbon and a through-channel, the carbon nanotube structure having a defined height to through-channel width aspect ratio, wherein:
the defined height to through-channel width aspect ratio is based on a defined collimation to diffraction ratio, wherein, as the defined height to through-channel width aspect ratio increases, light collimation by the collimator increases and diffraction by the collimator decreases;
the set of aligned carbon nanotubes infiltrated by carbon is configured to absorb a first portion of light that travels through the through-channel at a first angle and impinges a side of a first through-channel portion;
the set of aligned carbon nanotubes infiltrated by the carbon is configured to allow a second portion of the light that enters the through-channel at a second angle to pass through from a top of the through-channel to a bottom of the through-channel, and wherein at least one of the nanotubes includes a bolstering material, configured to increase resistance against an applied force.

17. The collimator of claim 16, wherein the defined height to through-channel width aspect ratio ranges from 3:1 to 10:1.

18. The collimator of claim 16, wherein the defined height to through-channel width aspect ratio is 5:1.

19. The collimator of claim 16, wherein the set of aligned carbon nanotubes infiltrated by carbon forms a wall structure with a thickness ranging from 1 micron to 50 microns and a height ranging from 50 microns to 1000 microns.

* * * * *